US012708554B2

(12) United States Patent
Eisenfrats et al.

(10) Patent No.: US 12,708,554 B2
(45) Date of Patent: Aug. 18, 2026

(54) BIOMATERIAL COMPOSITIONS AND METHODS OF DELIVERY

(71) Applicant: Contraline, Inc., Charlottesville, VA (US)

(72) Inventors: Kevin Eisenfrats, Charlottesville, VA (US); Gregory Grover, Houston, TX (US); Rucha Bhat, Manassas, VA (US); Tyler Chiartas, Charlottesville, VA (US); Nicholas Matsumoto, Charlottesville, VA (US)

(73) Assignee: Contraline, Inc., Charlottesville, VA (US)

(*) Notice: Subject to any disclaimer, the term of this patent is extended or adjusted under 35 U.S.C. 154(b) by 758 days.

(21) Appl. No.: 17/924,091

(22) PCT Filed: May 13, 2021

(86) PCT No.: PCT/US2021/032235
§ 371 (c)(1),
(2) Date: Nov. 8, 2022

(87) PCT Pub. No.: WO2021/231717
PCT Pub. Date: Nov. 18, 2021

(65) Prior Publication Data

US 2023/0190515 A1 Jun. 22, 2023

Related U.S. Application Data

(60) Provisional application No. 63/056,124, filed on Jul. 24, 2020, provisional application No. 63/024,628, filed on May 14, 2020.

(51) Int. Cl.
*A61F 6/22* (2006.01)
*A61F 6/00* (2006.01)
(Continued)

(52) U.S. Cl.
CPC ................ *A61F 6/22* (2013.01); *A61F 6/005* (2013.01); *A61L 31/06* (2013.01); *A61L 31/145* (2013.01);
(Continued)

(58) Field of Classification Search
CPC combination set(s) only.
See application file for complete search history.

(56) References Cited

U.S. PATENT DOCUMENTS 3,223,083 A 12/1965 Cobey
3,716,056 A 2/1973 Brodsky et al.
(Continued)

FOREIGN PATENT DOCUMENTS

CN 101812194 4/2012
CN 203493942 3/2014
(Continued)

OTHER PUBLICATIONS

In situ covalently cross-linked PEG hydrogel for ocular drug delivery, Yu et al., International Journal of Pharmaceutics, 470, (2014), 151-157 (Year: 2014).*
(Continued)

*Primary Examiner* — Peter A Salamon
(74) *Attorney, Agent, or Firm* — Mills IP Law, PLLC

(57) ABSTRACT

Delivery systems, compositions, and methods for forming and delivering biomaterials from two components are described. Specifically, a composition includes a first component and a second component that are each formulated to be crosslinked with the other to form a hydrogel. The first component and the second component are formulated to have an initial storage modulus (initial G') and an initial loss modulus (initial G") when initially combined such that a ratio of the initial G" to the initial G' is between about 5 and about 100. The first component and the second component
(Continued)

are formulated to have a gelation storage modulus (gelation G') and a gelation loss modulus (gelation G") at a gelation time after the first component and the second component are combined such that a ratio of the gelation G" to the gelation G' is less than about 1. The gelation time is less than about 120 seconds.

20 Claims, 22 Drawing Sheets

(51) Int. Cl.
*A61F 6/06* (2006.01)
*A61L 31/06* (2006.01)
*A61L 31/14* (2006.01)
*A61M 5/19* (2006.01)

(52) U.S. Cl.
CPC ............ *A61M 5/19* (2013.01); *A61L 2400/06* (2013.01); *A61M 2210/163* (2013.01)

(56) References Cited

U.S. PATENT DOCUMENTS 4,044,757 A 8/1977 Mcwhorter et al.
4,269,174 A 5/1981 Adair
4,273,109 A 6/1981 Enderby
4,366,919 A 1/1983 Anderson
4,804,691 A 2/1989 English et al.
4,887,605 A 12/1989 Angelsen et al.
4,920,982 A 5/1990 Goldstein
4,967,949 A 11/1990 Sandhaus
4,978,336 A 12/1990 Capozzi et al.
4,979,942 A 12/1990 Wolf et al.
5,065,751 A 11/1991 Wolf
5,208,281 A * 5/1993 Glaser .................. G03F 7/0275 524/202
5,240,997 A 8/1993 Yanai et al.
5,248,311 A 9/1993 Black et al.
5,258,042 A 11/1993 Mehta
5,380,317 A 1/1995 Everett et al.
5,383,896 A 1/1995 Gershony et al.
5,437,660 A 8/1995 Johnson et al.
5,459,173 A * 10/1995 Glaser ................. C08G 75/045 528/217
5,488,075 A 1/1996 Guha
5,575,815 A 11/1996 Slepian et al.
5,607,419 A 3/1997 Amplatz et al.
5,612,052 A 3/1997 Shalaby
5,667,767 A 9/1997 Greff et al.
5,695,740 A 12/1997 Porter
5,702,717 A 12/1997 Cha et al.
5,714,159 A 2/1998 Shalaby
5,749,968 A 5/1998 Melanson et al.
5,797,397 A 8/1998 Rosenberg
5,833,682 A 11/1998 Amplatz et al.
5,866,554 A 2/1999 Shalaby et al.
5,947,893 A 9/1999 Agrawal et al.
5,968,018 A 10/1999 Freeman et al.
5,989,580 A 11/1999 Wallace et al.
6,037,331 A 3/2000 Shalaby et al.
6,066,325 A 5/2000 Wallace et al.
6,096,052 A 8/2000 Callister et al.
6,103,254 A 8/2000 Wallace et al.
6,197,940 B1 3/2001 Klinefelter
6,224,893 B1 5/2001 Langer et al.
6,297,337 B1 10/2001 Marchant et al.
6,328,229 B1 12/2001 Duronio et al.
6,378,524 B1 4/2002 Jones
6,379,373 B1 4/2002 Sawhney et al.
6,394,314 B1 5/2002 Sawhney et al.
6,413,539 B1 7/2002 Shalaby
6,432,116 B1 8/2002 Callister et al.
6,454,762 B1 9/2002 Roesler et al.
6,461,325 B1 10/2002 Delmotte et al.
6,461,569 B1 10/2002 Boudreaux
6,464,663 B1 10/2002 Zinger
6,485,426 B2 11/2002 Sandhu
6,514,534 B1 2/2003 Sawhney
6,514,535 B2 2/2003 Marchant
6,531,111 B1 3/2003 Whalen, II et al.
6,610,033 B1 8/2003 Melanson et al.
6,660,247 B1 12/2003 Gutowska et al.
6,703,047 B2 3/2004 Sawhney et al.
6,719,778 B1 4/2004 Tassel et al.
6,723,090 B2 4/2004 Altshuler et al.
6,723,781 B1 4/2004 Frate et al.
6,756,031 B2 6/2004 Evans et al.
6,802,838 B2 10/2004 Loeb et al.
6,852,099 B2 2/2005 Redl et al.
6,858,219 B2 2/2005 Evans et al.
6,957,747 B2 10/2005 Peeler et al.
6,970,587 B1 11/2005 Rogers
7,022,073 B2 4/2006 Fan et al.
7,073,504 B2 7/2006 Callister et al.
7,135,027 B2 11/2006 Delmotte
7,160,931 B2 1/2007 Cheng et al.
7,252,677 B2 8/2007 Burwell et al.
7,347,850 B2 3/2008 Sawhney
7,396,354 B2 7/2008 Rychnovsky et al.
7,398,780 B2 7/2008 Callister et al.
7,641,075 B2 1/2010 Crews
7,694,683 B2 4/2010 Callister et al.
7,754,212 B2 7/2010 Klinefelter
7,789,891 B2 9/2010 Wallace
7,871,637 B2 1/2011 Qian et al.
7,914,514 B2 3/2011 Calderon
7,914,541 B2 3/2011 Sawhney et al.
7,918,863 B2 4/2011 Nguyen et al.
7,975,697 B2 7/2011 Callister et al.
8,048,086 B2 11/2011 Lee-Sepsick et al.
8,048,101 B2 11/2011 Lee-Sepsick et al.
8,052,669 B2 11/2011 Lee-Sepsick et al.
8,113,205 B2 2/2012 Callister et al.
8,123,693 B2 2/2012 Connor et al.
8,137,304 B2 3/2012 Chavez et al.
8,226,680 B2 7/2012 Wallace
8,235,047 B2 8/2012 Swann et al.
8,257,723 B2 9/2012 Noyes
8,303,981 B2 11/2012 Wallace et al.
8,316,853 B2 11/2012 Lee-Sepsick et al.
8,316,854 B2 11/2012 Lee-Sepsick et al.
8,322,341 B2 12/2012 Koeller
8,324,193 B2 12/2012 Lee-Sepsick et al.
8,336,552 B2 12/2012 Lee-Sepsick et al.
8,343,183 B2 1/2013 D'Alessio et al.
8,343,710 B1 1/2013 Anseth et al.
8,353,892 B2 1/2013 Thompson et al.
8,357,378 B2 1/2013 Wallace et al.
8,360,064 B2 1/2013 Swann et al.
8,389,630 B2 * 3/2013 Tamai .................. C08F 299/00 525/107
8,434,489 B2 5/2013 Gopal et al.
8,440,487 B2 5/2013 Furumura
8,475,532 B2 7/2013 Vresilovic et al.
8,512,729 B2 8/2013 Wallace et al.
8,523,848 B2 9/2013 Fried et al.
8,550,085 B2 10/2013 Callister et al.
8,551,001 B2 10/2013 Connor et al.
8,603,025 B2 12/2013 Pongratz et al.
8,603,080 B1 12/2013 Fried et al.
8,603,511 B2 12/2013 Wallace et al.
8,613,282 B2 12/2013 Nikolchev et al.
8,617,519 B2 12/2013 Binetti et al.
8,689,792 B2 4/2014 Jimenez et al.
8,695,606 B2 4/2014 Lee-Sepsick et al.
8,726,906 B2 5/2014 Lee-Sepsick et al.
8,766,853 B2 7/2014 Furumura et al.
8,801,764 B2 8/2014 Suarez et al.
8,933,784 B2 1/2015 Furumura et al.
8,960,501 B2 2/2015 Pappalardo
8,986,730 B2 3/2015 Sawhney et al.
9,034,053 B2 5/2015 Lee-Sepsick et al.

(56) References Cited

U.S. PATENT DOCUMENTS 9,155,543 B2 10/2015 Walsh et al.
9,180,196 B2 11/2015 Anseth et al.
9,193,816 B2 11/2015 Jiang et al.
9,220,880 B2 12/2015 Lee-Sepsick et al.
9,308,283 B2 4/2016 Campbell et al.
9,445,795 B2 9/2016 Ohri et al.
9,463,004 B2 10/2016 Campbell et al.
9,492,383 B2 * 11/2016 Gravett .............. A61L 24/0015
9,566,365 B2 2/2017 Kaplan et al.
9,586,005 B2 3/2017 Steffen
9,707,319 B2 7/2017 Geppert et al.
9,750,695 B2 9/2017 Richard
9,861,515 B2 1/2018 DePinto et al.
10,046,115 B2 8/2018 Bokelman et al.
10,155,063 B2 12/2018 Herr et al.
10,507,264 B1 12/2019 Lowman et al.
10,576,206 B2 3/2020 Edwards et al.
10,751,124 B2 8/2020 Eisenfrats et al.
11,253,391 B2 2/2022 Grover et al.
11,510,807 B2 11/2022 Grover et al.
2002/0032463 A1 3/2002 Cruise et al.
2002/0051750 A1 5/2002 Schutt et al.
2002/0106328 A1 8/2002 Johnson et al.
2002/0106411 A1 8/2002 Wironen et al.
2002/0173586 A1 11/2002 Jeong et al.
2003/0185758 A1 10/2003 Evans et al.
2003/0199865 A1 10/2003 Knudson et al.
2003/0206864 A1 11/2003 Mangin
2004/0013292 A1 1/2004 Raunig
2004/0062808 A1 4/2004 Langrana et al.
2004/0087930 A1 5/2004 Whalen et al.
2004/0240715 A1 12/2004 Wicker et al.
2004/0267308 A1 12/2004 Bagaoisan et al.
2005/0045183 A1 3/2005 Callister et al.
2005/0142162 A1 6/2005 Hunter et al.
2005/0147599 A1 7/2005 Hunter et al.
2005/0149117 A1 7/2005 Khosravi et al.
2005/0192616 A1 9/2005 Callister et al.
2005/0266086 A1 12/2005 Sawhney
2005/0283098 A1 12/2005 Conston et al.
2005/0288481 A1 12/2005 DesNoyer et al.
2006/0121087 A1 6/2006 Williams et al.
2006/0222596 A1 10/2006 Askari et al.
2006/0241452 A1 10/2006 Cerofolini
2007/0016128 A1 1/2007 Keller
2007/0060906 A1 3/2007 Wu
2007/0163601 A1 7/2007 Pollock et al.
2007/0197954 A1 8/2007 Keenan
2007/0231366 A1 10/2007 Sawhney et al.
2008/0039890 A1 2/2008 Matson et al.
2008/0045865 A1 2/2008 Kislev
2008/0071269 A1 3/2008 Hilario et al.
2008/0103564 A1 5/2008 Burkinshaw et al.
2008/0154345 A1 6/2008 Taylor
2008/0308110 A1 12/2008 Callister et al.
2009/0024155 A1 1/2009 Lee-Sepsick et al.
2009/0048588 A1 2/2009 Peng et al.
2009/0053276 A1 2/2009 Richard
2009/0076459 A1 3/2009 Goldberg
2009/0127288 A1 5/2009 Keller
2009/0274678 A1 11/2009 Calabro et al.
2009/0277457 A1 11/2009 Hoey et al.
2010/0003297 A1 1/2010 Tobias et al.
2010/0006339 A1 1/2010 Desai
2010/0063392 A1 3/2010 Nishina et al.
2010/0068153 A1 3/2010 Bangera et al.
2010/0089406 A1 4/2010 Kachiguina
2010/0158813 A1 6/2010 Paradossi et al.
2010/0272672 A1 10/2010 Kita et al.
2010/0311861 A1 * 12/2010 Clapper .............. C08G 18/792
522/182
2010/0318035 A1 12/2010 Edwards et al.
2011/0021970 A1 1/2011 Vo-Dinh et al.
2011/0065809 A1 3/2011 Benz et al.
2011/0125185 A1 5/2011 Stopek et al.
2011/0137150 A1 6/2011 Connor et al.
2011/0165114 A1 7/2011 McCoy et al.
2011/0245866 A1 10/2011 Cassingham et al.
2012/0014978 A1 1/2012 Hafner et al.
2012/0149781 A1 6/2012 Lee et al.
2012/0165804 A1 6/2012 Newell et al.
2012/0192872 A1 8/2012 Rudakov et al.
2012/0226226 A1 9/2012 Edwards et al.
2012/0295214 A1 11/2012 Wang et al.
2013/0018314 A1 1/2013 Teague et al.
2013/0131632 A1 5/2013 Mudd et al.
2013/0220335 A1 8/2013 Lee-Sepsick et al.
2013/0230496 A1 9/2013 Mohapatra et al.
2013/0244975 A1 9/2013 Baldwin et al.
2013/0245604 A1 9/2013 Kouyoumjian et al.
2013/0331770 A1 12/2013 Kirk et al.
2013/0331771 A1 12/2013 Kirk et al.
2014/0046182 A1 2/2014 Connor et al.
2014/0114261 A1 4/2014 Geppert et al.
2014/0121699 A1 5/2014 Anderson et al.
2014/0128497 A1 5/2014 Ladet et al.
2014/0256831 A1 9/2014 Ito et al.
2014/0261446 A1 9/2014 Sjoquist et al.
2014/0276384 A1 9/2014 Schwab et al.
2015/0045729 A1 2/2015 Denzer et al.
2015/0068531 A1 3/2015 Lee-Sepsick et al.
2015/0136144 A1 5/2015 DePinto et al.
2015/0196684 A1 7/2015 Guillen et al.
2015/0231246 A1 8/2015 Tae et al.
2016/0024326 A1 1/2016 Khan et al.
2016/0114046 A1 4/2016 Brudno et al.
2016/0151535 A1 6/2016 Hoare et al.
2016/0153999 A1 6/2016 Tibbitt et al.
2016/0193392 A1 7/2016 Askari et al.
2016/0317621 A1 11/2016 Bright
2017/0014569 A1 1/2017 Flanagan et al.
2017/0130194 A1 5/2017 Lee et al.
2017/0136143 A1 5/2017 Herr et al.
2017/0136144 A1 5/2017 Herr et al.
2017/0189581 A1 7/2017 Desai et al.
2017/0296749 A1 10/2017 Porcher
2018/0028715 A1 2/2018 Eisenfrats
2018/0092769 A1 4/2018 DePinto et al.
2018/0185096 A1 7/2018 Eisenfrats et al.
2018/0369481 A1 12/2018 Pedersen et al.
2018/0369482 A1 12/2018 Pedersen et al.
2018/0369483 A1 12/2018 Pedersen et al.
2019/0009029 A1 1/2019 Fabricus et al.
2019/0038454 A1 * 2/2019 Eisenfrats ........ A61B 17/12186
2019/0053790 A1 2/2019 Grover et al.
2019/0060513 A1 2/2019 Herr et al.
2019/0224419 A1 7/2019 Pedersen et al.
2020/0146876 A1 5/2020 Grover et al.
2020/0147301 A1 5/2020 Grover et al.
2020/0237388 A1 7/2020 Eisenfrats et al.
2020/0352649 A1 11/2020 Eisenfrats et al.
2020/0384207 A1 12/2020 Egesborg et al.
2022/0142812 A1 5/2022 Grover et al.
2022/0168461 A1 6/2022 Herr et al.
2022/0175672 A1 6/2022 Eisenfrats et al.
2022/0313475 A1 10/2022 Grover et al.
2023/0116862 A1 4/2023 Grover et al.
2023/0346589 A1 11/2023 Grover et al.

FOREIGN PATENT DOCUMENTS

CN 103724638 12/2015
EP 0547530 6/1993
EP 2233160 9/2010
EP 3275469 1/2018
JP 2016155994 9/2016
WO WO96/16691 6/1996
WO WO2008115694 9/2008
WO WO2009137446 11/2009
WO WO2009148405 12/2009
WO WO2012112417 8/2012
WO WO2015168090 11/2015
WO WO2016094535 6/2016
WO WO2016154288 9/2016

(56) References Cited

FOREIGN PATENT DOCUMENTS

| | | |
|---|---|---|
| WO | WO2016164828 | 10/2016 |
| WO | WO2017044983 | 3/2017 |
| WO | WO2017083753 | 5/2017 |
| WO | WO2017114908 | 7/2017 |
| WO | WO2017152036 | 9/2017 |
| WO | WO2017174071 | 10/2017 |
| WO | WO2018104537 | 6/2018 |
| WO | WO2018129369 | 7/2018 |
| WO | WO2018144481 | 8/2018 |
| WO | WO2019070632 | 4/2019 |
| WO | WO2020102234 | 5/2020 |
| WO | WO2021035217 | 2/2021 |

OTHER PUBLICATIONS

Office Action for U.S. Appl. No. 17/677,295, mailed Sep. 28, 2022.
Office Action for U.S. Appl. No. 16/681,572, mailed Oct. 4, 2021.
Office Action for U.S. Appl. No. 16/681,577, mailed Nov. 9, 2021.
PCT/US19/60986 International Search Report and Written Opinion mailed Apr. 2, 2020.
Invitation to Pay Additional Fees for PCT/US2021/032235, mailed Jul. 6, 2021.
International Search Report and Written Opinion for PCT/US2021/032235, mailed Sep. 28, 2021.
Extended Search Report for European Application No. 19883448.3, mailed Jul. 20, 2022.
Abbe, Carmen R. et al. "Assessing safety in hormonal male contraception: a critical appraisal of adverse events reported in a male contraceptive trial," BMJ Sex. Reprod. Health, vol. 46, No. 2, Apr. 2020, pp. 139-146, HHS Public Access, Arthor Manuscript, 15 pages.
Abdala, Nitamar et al., "Use of Ethylene Vinyl Alcohol Copolymer for Tubal Sterilization by Selective Cathelerization in Rabbits," Journal of Vascular and Interventional Radiology, vol. 12(8), Aug. 2001, pp. 979-984.
Ahmed, Enas M., "Hydrogel: Preparation, characterization, and applications: A review," Journal of Advanced Research, vol. 6, Issue 2, 2015, pp. 105-121.
Ahrens, K.A. et al. "Unintended pregnancy and interpregnancy interval by maternal age, National Survey of Family Growth," Contraception 98, 52-55 (2018), 8 pgs.
Akbari et al. "Large-area graphene-based nanofiltration membranes by shear alignment of discotic nematic liquid crystals of graphene oxide," Nature Communications, published Mar. 7, 2016 (pp. 1-12).
Akram, Farhan, et al. "Segmentation of Regions of Interest Using Active Contours with SPF Function," Hindawi Publishing Corp., Computational Mathematical Methods in Medicine, vol. 2015; Article ID 710326, 15 pgs.
An, Lu, et al., "Paramagnetic hollow silica nanospheres for in vivo targeted ultrasound and magnetic resonance imaging," Biomaterials, vol. 35, Issue 20, 2014, pp. 5381-5392.
Amory, John K. "Male contraception," Fertility and Sterility, vol. 106, No. 6, Nov. 2016, pp. 1303-1309.
Amory, John K. "Development of Novel Male Contraceptives," Clin. Transl. Sci. 13 (2020), pp. 228-237.
Appel et al. "Self-assembled hydrogels utilizing polymer-nanoparticle interactions," Nature Communications, vol. 6, No. 6295, Feb. 19, 2015, [retrieved on Aug. 24, 2021]. Retrieved from the inernet <URL: https://www.nature.com/articles/ncomms7295.pdf?origin+ppub> pp. 1-9.
Attaran, Robert R., et al. "Protocol for Optimal Detection and Exclusion of a Patent Foramen Ovale Using Transthoracic Echocardiography with Agitated Saline Microbubbles" Echocardiography: A Jrnl. Of CV Ultrasound & Allied Tech., vol. 23, No. 7 2006, pp. 616-622.
Avery, R. K. et al. "An injectable shear-thinning biomaterial for endovascular embolization," Science Translation Medicine, vol. 8, 365ra156 (2016) Nov. 16, 2016 (13 pgs.).
Bakaic, Emilia et al. "Injectable hydrogels based on poly(ethylene glycol) and derivatives as functional biomaterials" RSC Adv 5, 35469-35486 (2015), RSC Advances, Accepted Manuscript, <online: https://pubs.rsc.org/en/content/getauthorversionpdf/C4RA13581D>, 51 pages.
Bank, Alan J., et al., "Contribution of Collagen, Elastin, and Smooth Muscle to In Vivo Human Brachial Artery Wall Stress and Elastic Modulus," Circulation, 1996;94:3263-3270, Originally published Dec. 15, 1996, 17 pgs.
Bearak, Jonathan et al. "Global, regional, and subregional trends in unintended pregnancy and its outcomes from 1990 to 2014: estimates from a Bayesian hierarchical model," Lancet Glob. Health, vol. 6, Apr. 2018, pp. e380-e389.
Behre, Hermann et al. "Efficacy and Safety of an Injectable Combination Hormonal Contraceptive for Men," J. Clin. Endocrinol. Metab. vol. 101, No. 12 Dec. 2016, pp. 4779-4788.
Bustamante-Forest, Rosa et al. "Changing men's involvement in reproductive health and family planning," Nurs. Clin. North Am. 39, 301-318 (2004).
Calliada, Fabrizio, et al., "Ultrasound contrast agents: basic principles", European Journal of Radiology 27 (1998) pp. S157-S160.
Chaki, S.P. et al., "A short-term evaluation of semen and accessory sex gland function in phase III trial subjects receiving intravasal contraceptive RISUG," Contraception, vol. 67(1), 2003, pp. 73-78.
Chao, Jing H. et al. "The current state of male hormonal contraception," Pharmacology & Therapeutics, Accepted Manuscript, vol. 163, Jul. 2016, (42 pgs.).
Clenny T.L. et al., "Vasectomy Techniques," Am Fam Physician, vol. 60(1), Jul. 1, 1999, 9 pgs.
Colagross-Schouten, Angela et al. "The contraceptive efficacy of intravas injection of Vasalgel™ for adult male rhesus monkeys," Basic and Clinical Andrology, 27:4 (2017), 7 pages.
Cosgrove, David "Ultrasound contrast agents: An overview," European Journal of Radiology, vol. 60, Issue 3, pp. 324-330.
D'Anna, Laura Hoyt et al. "Factors Associated With Condom Use Problems During Vaginal Sex With Main and Non-Main Partners," Sexually Transmitted Diseases, vol. 39, No. 9, Sep. 2012, pp. 687-693.
Daniels, Kimberly "Unmarried Men's Contraceptive Use at Recent Sexual Intercourse: United States, 2011-2015," Products, NCHS Data Brief, No. 284 <https://www.cdc.gov/nchs/products/databriefs/db284.htm> Aug. 2017, 8 pages.
Dorman, E. et al. "Modeling the impact of novel male contraceptive methods on reductions in unintended pregnancies in Nigeria, South Africa, and the United States," Contraception 97, 62-69, Jan. 2018, Arthor Manuscript, HHS Public Access <online: https://www.ncbi.nlm.nih.gov/pmc/articles/PMC5732079/pdf/nihms904029.pdf> 20 pages.
Dressaire, Emilie, et al. "Interfacial Polygonal Nanopatterning of Stable Microbubbles," Science, vol. 320, Issue 5880, May 30, 2008, pp. 1198-1201.
El-Sherif, Dalia M., et al., "Development of a novel method for synthesis of a polymeric ultrasound contrast agent," Journal of Biomedical Materials Research Part A, (2003) 66A(2), 347-355.
Fan, Hailong et al., "Fabrication, mechanical properties, and biocompatibility of graphene-reinforced chitosan composites," Biomacromolecules, 11(9), 2010, pp. 2345-2351.
Flickinger, Charles J., "Alterations in the fine structure of the rat epididymis after vasectomy." The Anatomical Record, 173(3): 1972, pp. 377-299.
Flickinger, Charles J. et al., "The influence of vasovasostomy on testicular alterations after vasectomy in lewis rats," The Anatomical Record, 217(2), 1987, pp. 137-145.
Flickinger, Charles J., "Ultrastructure of the rat testis after vasectomy," The Anatomical Record, 174(4), 1972, pp. 477-493.
Fulton, David A., "Click chemistry gets reversible" Nature Chemistry, vol. 8, Oct. 2016, pp. 899-900.
Garmiak, R. et al., "Echocardiography of the aortic root," Investigative Radiology, vol. 3, Sep.-Oct. 1968, pp. 356-366.
Grover, Gregory N. et al., "Biocompatible Hydrogels by Oxime Click Chemistry," Biomacromolecules, vol. 13, No. 10, Oct. 8, 2012, pp. 1-10.

(56) References Cited

OTHER PUBLICATIONS

Guha, S. K. et al. "Phase I clinical trial of an injectable contraceptive for the male," Contraception vol. 48, (1993) pp. 367-375.
Guha, Sujoy K. et al., "Phase II Clinical Trial of a Vas Deferens Injectable Contraceptive for the Male," Contraception, vol. 56, 1997, pp. 245-250.
Guha, Sujoy K. "Biophysical mechanism-mediated time-dependent effect on sperm of human and monkey vas implanted polyelectrolyte contraceptive," Asian J. Androl. 9(2), (2007) pp. 221-227.
Guimaraes, C. F. et al. "The stiffness of living tissues and its implications for tissue engineering," Nature Reviews, Materials 5, 2020, 20 pgs.
Hafez, ES, et al. "Atlas of Human Reproduction: By Scanning Electron Microscopy", 1982, MTP Press, Hingham, MA, Part 1-1 (separated into 4 parts for Filing), 85 pgs.
Hafez, ES, et al. "Atlas of Human Reproduction: By Scanning Electron Microscopy", 1982, MTP Press, Hingham, MA, Part 1-2 (separated into 4 parts for Filing), 85 pgs.
Hafez, ES, et al. "Atlas of Human Reproduction: By Scanning Electron Microscopy", 1982, MTP Press, Hingham, MA, Part 2-1 (separated into 4 parts for Filing), 66 pgs.
Hafez, ES, et al. "Atlas of Human Reproduction: By Scanning Electron Microscopy", 1982, MTP Press, Hingham, MA, Part 2-2 (separated into 4 parts for Filing), 101 pgs.
Hashemi, Ehsan et al., "Cyto and genotoxicities of graphene oxide and reduced graphene oxide sheets on spermatozoa," RSC Advances, 4(52), 2014, pp. 27213-27223.
Heinemann, Klaas et al. "Attitudes toward male fertility control: results of a multinational survey on four continents," Human Reproduction vol. 20, No. 2, (2005), pp. 549-556.
International Standard "Biological evaluation of medical devices. Part 5: Tests for in vitro cytotoxicity." ISO 10993-5, Third edition Jun. 1, 2009, 42 pgs.
Jha, R.K. et al., "Smart RISUG: A potential new contraceptive and its magnetic field-mediated sperm interaction," International Journal of Nanomedicine, vol. 4, 2009, pp. 55-64.
Kihara, K. et al. "A New Method to Generate Canine Seminal Emission and Its Application to Men: Direct Electrical Stimulation of the Vas Deferen,". Journal of Andrology, vol. 15, No. 5, Sep./Oct. 1994, pp. 479-483.
Khilwani, Barkha et al. "RISUG® as a male contraceptive: journey from bench to bedside," Basic and Clinical Andrology, 30:2, (2020), 12 pages.
Kloxin, April et al., "Photodegradable hydrogels for dynamic tuning of physical and chemical properties," Science, vol. 324, Apr. 3, 2009, pp. 59-63.
Koul, V. et al., "Reversibility With Sodium Bicarbonate of Styrene Maleic Anhydride, an Intravasal Injectable Contraceptive, in Male Rats," Contraception vol. 58(4), 1998, pp. 227-231.
Lahiri, Debrupa et al., "Graphene nanoplatelet-induced strengthening of ultrahigh molecular weight polyethylene and biocompatibility in vitro," ACS Applied Materials & Interfaces, vol. 4, 2012, pp. 2234-2241.
Lee, Wong Cheng et al., "Origin of enhanced stem cell growth and differentiation on graphene and graphene oxide," American Chemical Society, ACS Nano, vol. 5, No. 9, 2011, pp. 7334-7341.
Leocadio, D.E. et al., "Anatomical and histological equivalence of the human, canine, and bull vas deferens" The Canadian Journal of Urology, 18(3), Jun. 1, 2011, pp. 5699-5704.
Li, Jianyu et al. "Designing hydrogels for controlled drug delivery," Nat. Rev. Mater. vol. 1(12) pp. 1-17 (2016), Arthor Manuscript, HHS Public Access, 38 pages.
Li, Shunqiang et al., "The No-Scalpel Vasectomy," The Journal of Urology, vol. 145, Issue 2, Feb. 1991, pp. 341-344.
Lipshultz, Larry I. et al. "Techniques for Vasectomy Reversal," Urol. Clin. North Am. 36, 2009, pp. 375-382.
Liu, X. et al., "The Relationship Between the Vas Volume and the Anatomic Size of the Vas Deferens", Contraception, vol. 56{6), 1997, pp. 391-394.
Lohiya, N.K. et al., "Preclinical evaluation for noninvasive reversal following long-term vas occlusion with styrene maleic anhydride in langur monkeys," Contraception, vol. 71(3), 2005, pp. 214-226.
Lohiya, N.K et al., "RISUG: An intravasal injectable male contraceptive", Indian J Med Res 140 (Supplement), 2014, pp. 63-72.
Marks, Sheldon H. F., "Chapter 3—Predicting Reversal Success," pp. 9-35, Excerpt from *Manual of Vasovasostomy and Vasoepididymostomy*, (ed. Marks, S. H. F.) (Springer International Publishing, 2019). doi:10.1007/978-3-030-00455-2_3, 31 pages.
Mayans, David et al., "Neuromuscular ultrasonography: Quantifying muscle and nerve measurements," Phys. Med. Rehabil. Clin. N. Am. vol. 23(1), 2011, pp. 1-19.
Mckay, Craig S., et al., "Click Chemistry in Complex Mixtures: Bioorthogonal Bioconjugation," Chem Biol., vol. 21(9) Sep. 18, 2014, pp. 1-51.
Mehrali, Mehdi et al., "Mechanical and in vitro biological performance of graphene nanoplatelets reinforced calcium silicate composite," PLOS One, vol. 9, Issue 9, Sep. 2014, pp. 1-14.
Middleton, W.D. et al., "High-Resolution Sonography of the Normal Extrapelvic Vas Deferens," J Ultrasound Med., vol. 28, 2009, pp. 839-846.
Mossman, J. A., et al., "Variation in mean human sperm length is linked with semen characteristics," Human Reproduction, vol. 28, No. 1, Oct. 28, 2012, pp. 22-32.
Naahidi, Sheva et al. "Biocompatibility of hydrogel-based scaffolds for tissue engineering applications," Biotechnology Advances, vol. 35, (2017) pp. 530-544.
Naughton, C. K., et al., "The Use of URYX for Reversible Vasectomy in a Rabbit Model," Journal of Andrology, vol. 25, No. 4, Jul./Aug. 2004, pp. 545-553.
Noble, J. Alison et al., "Ultrasound image segmentation: a survey," IEEE Trans Med Imaging, vol. 25, No. 8, Aug. 2006 pp. 987-1010.
Norouzi, M. et al., "Injectable hydrogel-based drug delivery systems for local cancer therapy," Drug Discovery Today, vol. 21, No. 11, Nov. 2016, pp. 1835-1849.
WHO Laboratory Manual for the Examination of Human Semen and Sperm-Cervical Mucus Interaction. (Cambridge University Press, 1999).
Paefgen, Vera et al., "Evolution of contrast agents for ultrasound imaging and ultrasound-mediated drug delivery," Frontiers in Pharmacology, vol. 6, Article 197, Sep. 2015 pp. 1-16.
Rubinstein, Michael et al. "Polymer Physics," Oxford University Press, Jun. 26, 2003, 458 pgs.
Reddy, Neena M., et al., "Vasectomy-Related Changes on Sonographic Examination of the Scrotum," Journal of Clinical Ultrasound, vol. 32, 2004, pp. 394-398.
Robinette, W.B. "Ultrasound Contrast Agents", Journal of Diagnostic Medical Sonography, vol. 13, Supplement, Sep./Oct. 1997, pp. 29S-34S.
Roy, S. et al., "Polyelectrolyte polymer properties in relation to male contraceptive RISUG® action," Colloids and Surfaces B: Biointerfaces vol. 69, 2009, pp. 77-84.
RP Photonics Encyclopedia, "Silica Fibers" <online: https:/www.rp-photonics.com/silica_fibers.html> At least as early as Oct. 2, 2017, 3 pgs.
Sadtler, Kaitlyn et al. "Design, clinical translation and immunological response of biomaterials in regenerative medicine," Nature Reviews Materials, vol. 1, Jul. 2016, pp. 1-17.
Sato, Kenji et al., "Spinal cord segments controlling the canine vas deferens and differentiation of the primate sympathetic pathways to the vas deferens," Microscopy. Research and Technique, vol. 42, (1998) pp. 390-397.
Shen, Z. L. et al., "Viscoelastic Properties of Isolated Collagen Fibrils," Biophysical Journal, vol. 100, Jun. 2011, pp. 3008-3015.
Sheynkin, Y. R. "History of Vasectomy." Urol. Clin. North Am. vol. 36, 2009, pp. 285-294.
Schmidt, S.S. et al. "Anatomical Sizes of the Human Vas Deferens After Vasectomy," Fertility and Sterility, vol. 27, No. 3, Mar. 1976, pp. 271-274.
Sigma-Aldrich "Safety Data Sheet" Version 4.2, for Product name: "Poly(vinyl alcohol-co-ethylene)", Product No. 414093, Revision Date: Jun. 25, 2014. Print Date: Mar. 27, 2017, 6 pgs.

(56) References Cited

OTHER PUBLICATIONS

Sigma-Aldrich "Syringe Needle Gauge Chart," <online: http://www.sigmaaldrich.com/chemistry/stockroom-reagents/learning-center/technicallibrary/needle-gauge-chart.html>, At least as early as Oct. 2, 2017, 2 pgs.

Singh, Sunilk et al., "Amine-Modified Graphene: Thrombo-Protective Safer Alternative to Graphene Oxide for Biomedical Applications," ACS Nano, vol. 6, No. 3, Jan. 1, 2012, pp. 2731-2740.

Singh, Susheela et al. "Unintended Pregnancy: Worldwide Levels, Trends, and Outcomes," Studies in Family Planning, vol. 41, No. 4, Dec. 2010, pp. 241-250.

Soebadi, D. M. et al., "Intravasal injection of formed-in-place medical grade silicone for vas occlusion", International Journal of Andrology, vol. 18, Suppl. 1, 1995, pp. 45-52.

Sonfield, Adam et al. "The public costs of births resulting from unintended pregnancies: national and state-level estimates," Perspectives on Sexual and Reproductive Health, vol. 43, No. 2, Jun. 2011, pp. 94-102.

Staruch, Robert M.T. et al., "Injectable Pore-Forming Hydrogel Scaffolds for Complex Wound Tissue Engineering: Designing and Controlling Their Porosity and Mechanical Properties," Tissue Engineering, Part B, vol. 23, No. 3, Nov. 3, 2017, 16 pgs.

Stockton, D.M. et al. "No-scalpel vasectomy: a technique for family physicians," Am Fam Physician, vol. 46, No. 4, Oct. 1992, 18 pgs.

Sundaram, Aparna et al. "Contraceptive Failure in the United States: Estimates from the 2006-2010 National Survey of Family Growth," Perspectives on Sexual and Reproductive Health, vol. 49, No. 1, Mar. 2017, pp. 7-16.

Szabo, T.L. et al., "Ultrasound Transducer Selection in Clinical Imaging Practice," Journal of Ultrasound in Medicine, vol. 32(4), 2013, pp. 573-582.

Tan, H. et al. "Injectable, Biodegradable Hydrogels for Tissue Engineering Applications," Materials 2010, vol. 3, pp. 1746-1767.

Trussell, James "Contraceptive failure in the United States," Contraception vol. 83, No. 5, 397-404, May 2011, 14 pages.

Waller, D. et al., "Azoospermia in rabbits following an intravas injection of Vasalgel," Basic and Clinical Andrology, vol. 26:6, 2016, pp. 1-8.

VenaSeal™ Closure System, Product Code: VS-402 <online: https://www.accessdata.fda.gov/cdrh_docs/pdf14/p140018c.pdf> PT-11348-01 Rev D, Feb. 2015, 24 pages.

Waller, D. et al. "Reversibility of Vasalgel™ male contraceptive in a rabbit model," Basic and Clinical Andrology, vol. 27:8 (2017), 9 pages.

World Standards, "Plug, socket & voltage by country," <online: http://www.worldstandards.eu/electricity/plug-voltage-by-country/>, At least as early as Oct. 2, 2017, 16 pgs.

Yazdkhasti, Mansureh et al., "Unintended Pregnancy and Its Adverse Social and Economic Consequences on Health System: A Narrative Review Article," Iran. J. Public Health, vol. 44, No. 1, Jan. 2015, pp. 12-21.

Zambon, J.V. et al., "Efficacy of percutaneous vas occlusion compared with conventional vasectomy", BJU International, vol. 86, 2000, pp. 699-706.

Zhang, Lu et al., "High strength graphene oxide/polyvinyl alcohol composite hydrogels," Journal of Materials Chemistry, vol. 21, 2011, pp. 10399-10406.

Zhao, Sheng-cai et al. "Intravasal injection of formed-in-place silcone rubber as a method of vas occlusion," International Journal of Andrology, vol. 15, Issue 6, 1992, pp. 460-464.

Zhao, Sheng-cai, "Vas Deferens Occlusion By Percutaneous Injection Of Polyurethane Elastomer Plugs: Clinical Experience And Reversibility," Contraception, vol. 41(5), May 1990, pp. 453-459.

Zhou, Joe et al. "Optical Fiber Tips and Their Applications," Polymicro Technologies, <online:https://www.molex.com/mx_upload/superfamily/polymicro/pdfs/Optical_Fiber_Tips_and_Their_Applications_Nov_2007.pdf>, Nov. 2007, 5 pgs.

Hogan, et al., "Needle-free delivery of macromolecules through the skin using controllable jet injectors," Expert Opin Drug Deliv. 2015;12(10): pp. 1637-1648.

* cited by examiner 1361
1362
1351
1354
1350
1353
1352
1363
1355
1370

1000
1100
1163
1370
1320
1350
1300
1301
1115
1400
1420
1413
1160
1114
1110
1240
1230
1150
1152
1120
1200

1000
1300
1115
1163
1320
1350
1301
1100
1370
1400
1420
1413
1160
1114
1150
1152
1230
1110
1120
1240
1200

Figure 22:
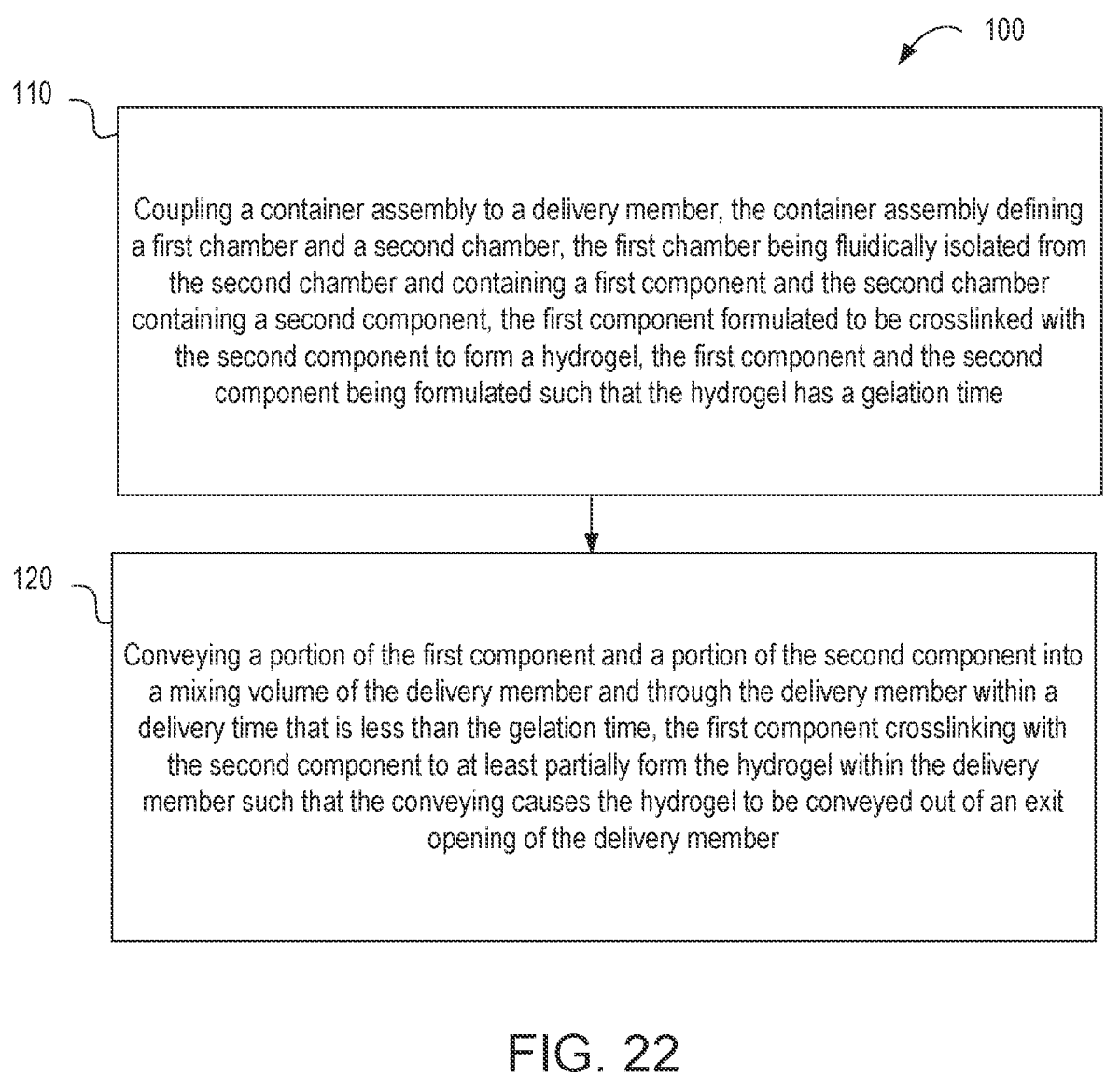

100

110

Coupling a container assembly to a delivery member, the container assembly defining a first chamber and a second chamber, the first chamber being fluidically isolated from the second chamber and containing a first component and the second chamber containing a second component, the first component formulated to be crosslinked with the second component to form a hydrogel, the first component and the second component being formulated such that the hydrogel has a gelation time

120

Conveying a portion of the first component and a portion of the second component into a mixing volume of the delivery member and through the delivery member within a delivery time that is less than the gelation time, the first component crosslinking with the second component to at least partially form the hydrogel within the delivery member such that the conveying causes the hydrogel to be conveyed out of an exit opening of the delivery member

BIOMATERIAL COMPOSITIONS AND METHODS OF DELIVERY

CROSS-REFERENCE TO RELATED APPLICATIONS

This application is a U.S. national stage filing under 35 U.S.C. § 371 of International Application No. PCT/US2021/032235 (filed May 13, 2021), entitled "BIOMATERIAL COMPOSITIONS AND METHODS OF DELIVERY," which claims benefit of priority to U.S. Provisional Application No. 63/024,628 entitled "Biomaterials Composition and Methods of Delivery," filed May 14, 2020, and U.S. Provisional Application No. 63/056,124 entitled "Biomaterials Composition and Methods of Delivery," filed Jul. 24, 2020, each of which is incorporated herein by reference in its entirety.

This application is also related to U.S. patent application Ser Nos. 16/681,572 and 16/681,577, each entitled "Systems and Methods for Delivering of Biomaterials," and each filed Nov. 12, 2019, each of which is incorporated herein by reference in its entirety.

BACKGROUND

The embodiments described herein relate generally to biomaterial compositions and methods of delivering biomaterials, and more particularly to controlled formation and delivery of a hydrogel to a body lumen, or other cavity, space, tissue or organ of a body.

Contraceptive usage has increased globally, yet many pregnancies are unintended. In the United States alone, these unintended pregnancies, which include mistimed, unplanned or unwanted pregnancies, result in a total public expenditure of ~$21 billion per year. These pregnancies are considered high-risk with evidence that both the women and the children experience worse health outcomes than intended pregnancies. Popular contraceptive methods include male/female condoms, female hormone treatments (pills, patches, implants, etc.), and intrauterine devices. Over the past three decades, even though many effective female contraceptive options have been introduced to market, unintended pregnancy rates have remained relatively constant. A promising strategy to reduce the number of unintended pregnancies and the subsequent societal and family costs is to increase contraceptive options, specifically options available to men.

While men make up about half of the population, they currently only have three contraceptive options available to them: condoms, withdrawal, and vasectomy. When used correctly, condoms are an effective contraceptive and prophylactic. However, condoms are frequently used incorrectly and are only ~85% effective overall, and have a low satisfaction rate. Vasectomy is considered permanent and very effective; however, it is difficult to reverse.

Currently, several methods of male contraception are under investigation. These methods can be broken down into two main categories: hormonal and vas-occlusive. Hormonal options such as hormone pills and creams often cause side-effects similar to those observed in female hormonal contraceptives. Some side effects of hormonal male contraceptives include mood swings, depression, and increased risk of suicide. Vas-occlusion has a similar mechanism of action to a vasectomy in that the sperm are prevented from entering into the ejaculatory duct, with the key difference that vas-occlusion does not sever the vessel. The most publicized vasocclusive technologies to date are reversible inhibition of sperm under guidance (RISUG) and Vasalgel (pre-hydrolyzed RISUG). These methods have been reported as being both occlusive and spermicidal (depending on the formulation of constituents used).

Biomaterials are natural or synthetic materials (such as polymers) that are suitable for introduction into living tissues as a therapeutic (to treat, augment, repair, modify, or replace a tissue function of the body) or as a diagnostic. Biomaterials such as hydrogel implants have been shown to be useful for embolization, drug delivery, sealing, filling, and occlusion purposes. Hydrogels are highly hydrated polymer chains or networks that are able to absorb significant volumes of water and can have tunable mechanical properties. Biomaterials are often injectable, such as through a needle and/or catheter into the body. When injected, the material may gel or cross-link to form the implant. Many known systems, however, deliver multiple components into the body that are then cross-linked within the body after delivery. As such, the formation of the delivered hydrogel can be dependent on the in vivo conditions. Such known methods can therefore expose the patient to both the underlying components (i.e., the monomers or macromers that form the delivered hydrogel) and the delivered hydrogel itself. Such known methods may also require additional stimulation after delivery into the body to facilitate formation of the hydrogel. Such additional steps can result in longer procedures and increased variability (i.e., patient-to-patient) for the procedure.

Some known systems and methods include injecting and/or implanting a biomaterial product (e.g., a hydrogel) into a small area such as the lumen of a vessel or duct. For example, in some applications, the biomaterial will form an implant that acts as an occlusion or embolization of a lumen. The occlusion can be used for providing contraception to a subject by occluding the vas deferens, fallopian tube(s), or uterus. Such occlusions can also be used to occlude any other body part, such as ducts, tissues, interstitial spaces, or organs such as for drug delivery, spacing, sealing, embolizing, or bulking purposes. Known delivery systems, however, do not provide the desired safety, accuracy, precision, and/or repeatability, particularly when micro-volumes are involved. For example, some known delivery systems and methods are specifically designed to produce a spray (e.g., for wound healing, etc.). Because precise control over the total amount delivered, timing of the delivery, rate of delivery and/or delivery force is not often a significant concern for such applications. Such known systems are not suitable for applications where delivery of a small, precise amount to a specific location is desired.

Some known systems include a manual delivery device, such as a syringe that is operated by hand to deliver the components. Such manual systems, however, can often result in high variability. For example, the manual force applied by a physician on a hand delivery device can vary from procedure-to-procedure, and those variations are further magnified when considering different physicians performing the delivery procedure on different patients under different operating conditions. The variations in manual force applied on known hand delivery devices may drastically impact the total delivery amount administered to a patient and/or to a specific target area, particularly when the desired amount of compositions is very small (e.g., 0.001 mL to 1 mL). Insufficient delivery of compositions may result in the target area not being properly occluded, embolized, or sealed, which may result in a failed operation. On the other hand, excess delivery of compositions may lead to undesired occlusion, embolization, or sealing of non-target areas, and may be problematic if the non-target areas are sensitive to the compositions or need to remain free from occlusion, embolization, or sealing. Excess delivery of composition may also result in delivery of a final amount greater than the capacity of the target area, resulting in damage. For example, if the volume of the compositions delivered exceeds a capacity of a target vessel, the target vessel may rupture or the tissue may experience a histological response.

Some known delivery systems include an electromechanical delivery mechanism, and therefore do not rely on the practitioner to generate the delivery forces and control the timing and delivery process. For example, high-pressure jet injectors have been used to deliver high-viscous materials such as liquids and powders into the body for drug delivery purposes (see Nora C Hogan, Andrew J Taberner, Lynette A Jones & Ian W Hunter (2015), Needle-free delivery of macromolecules through the skin using controllable jet injectors, Expert Opinion on Drug Delivery, 12:10, 1637-1648). However, these devices are usually only applicable for injections into the epidermis and do not have a needle or catheter attachment to inject liquids or fluids into other confined areas of the body. Furthermore, they are incapable of injecting already-formed gelled materials.

Moreover, such known electronic systems do not include desired control over the velocity, flow rate, and/or force with which the compositions are delivered. Known systems that use an energy storage device (e.g., spring, electromechanical device, etc.) are designed for high volume delivery (e.g., greater than 1 mL) and may also deliver the product at a force that causes damage to target tissue. For example, a high rate delivery or large delivery force may rupture, scar, or tear the target tissue; the overall safety and efficacy of the product is thus impacted. Such known systems may also deliver the underlying components too quickly such that the resulting biomaterial product to be delivered is not formed in the delivery system, but rather within or on the body tissue.

Thus, a need exists for compositions, devices, and methods for delivering biomaterials for medical procedures, including but not limited to contraception, where a controlled rate and volume of the biomaterials is desired. More specifically, a need exists for devices and methods for controlled delivery of at least a partially-formed hydrogel to a target site of a body where a controlled micro-volume is desired (e.g., 0.001 mL to 1 mL, or 1 μL-1,000 μL of volume).

SUMMARY

Compositions, delivery devices, and methods for forming and delivering biomaterials from two components are described herein. In particular, systems and methods for performing controlled delivery of biomaterials into or onto a body part, such as a body lumen, cavity, tissue or organ are described.

In some embodiments, a system includes a container assembly, a connector, a delivery member, and a drive assembly. The container assembly contains a first component and a second component with first component being separate from the second component within the container assembly. The first component is formulated to be crosslinked with the second component to form a hydrogel. The first component and the second component are formulated such that the hydrogel has a gelation time. The connector is configured to be coupled to the container assembly. The delivery member is configured to be coupled to the connector and to be inserted into a body lumen, cavity, tissue or organ. The drive assembly is configured to be operatively coupled to the container assembly. The drive assembly is further configured to move a first plunger within the first container to convey a portion of the first component from the first container and a second plunger within the second container to convey a portion of the second component from the second container. The drive assembly moves the first plunger and the second plunger to convey a portion of the first component and a portion of the second component through the connector and out of the delivery member within a delivery time that is less than the gelation time.

In some embodiments, a method includes coupling a container assembly to a delivery member. The container assembly defines a first chamber and a second chamber, with the first chamber being fluidically isolated from the second chamber. The first chamber contains a first component and the second chamber contains a second component. The first component is formulated to be crosslinked with the second component to form a hydrogel. The first component and the second component are formulated such that the hydrogel has a gelation time. A portion of the first component and a portion of the second component are conveyed into a mixing volume of the delivery member and through the delivery member within a delivery time that is less than the gelation time. The first component crosslinks with the second component to at least partially form the hydrogel within the delivery member such that the conveying causes the hydrogel to be conveyed out of an exit opening of the delivery member.

In some embodiments, a composition includes a first component and a second component that are each formulated to be crosslinked with the other to form a hydrogel. The first component and the second component are formulated to have an initial storage modulus (initial G') and an initial loss modulus (initial G") when initially combined such that a ratio of the initial G" to the initial G' is between about 5 and about 100. The first component and the second component are formulated to have a gelation storage modulus (gelation G') and a gelation loss modulus (gelation G") at a gelation time after the first component and the second component are combined such that a ratio of the gelation G" to the gelation G' is less than about 5, such as less than about 1. The gelation time is less than about 120 seconds.

In some embodiments, the gelation time is less than about 60 seconds. In other embodiments, the gelation time is less than about 30 seconds, and in some cases the gelation time may be instantaneous In yet other embodiments, the gelation time is between about 1 second and 60 seconds.

In some embodiments, the ratio of the gelation G" to the gelation G' is less than about 0.2. In other embodiments, the ratio of the gelation G" to the gelation G' is about 0.1. In yet other embodiments, the ratio of the gelation G" to the gelation G' is a ratio of up to 1, such as a ratio of up to 0.9, or up to 0.8, or up to 0.7, or up to 0.6, or up to 0.5, or up to 0.4, or up to 0.3, or up to 0.2, or up to 0.1.

The description below and the accompanying figures provide details on the various systems, methods and devices for delivering biomaterials.

BRIEF DESCRIPTION OF THE DRAWINGS

FIG. 22 is a flow chart of a method of delivering a hydrogel according to an embodiment.

FIG. 23 is a flow chart of a method of delivering a hydrogel according to an embodiment.

DETAILED DESCRIPTION

Figures 1A, 1B:
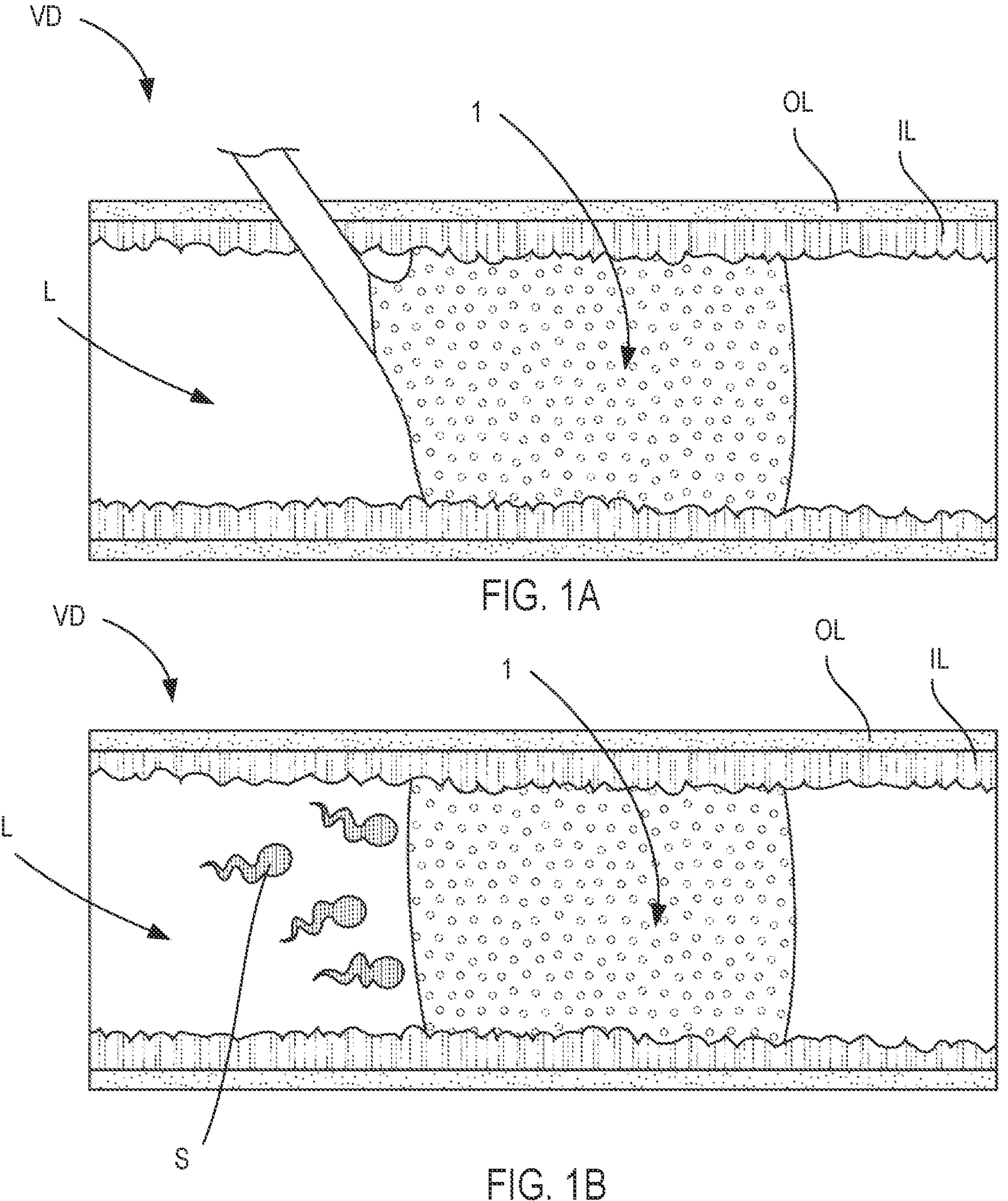
FIG. 1A is a cross-sectional illustration of a hydrogel system being injected into a lumen of a vas according to an embodiment.
FIG. 1B is a cross-section illustration of the hydrogel system of FIG. 1A after injection into the lumen of the vas.

As described herein, a two component hydrogel system was developed for vas-occlusion and tuned for precise delivery of a hydrogel material intraluminal into the vas. For example, as shown in FIG. 1A, a cross-sectional view of the vas VD is shown including a layer OL of outer circular smooth muscle fibers, a layer IL of inner longitudinal smooth muscle fibers, and an inner lumen L. A hydrogel material 1 can be conveyed into the inner lumen L via any delivery system of the types shown and described herein including a needle or catheter, for example, the delivery system 1000. In particular, as shown in FIG. 1B, the hydrogel material 1 based on the formulations described herein have low injection forces that rapidly form strong viscoelastic materials that swell to enable occlusion while withstanding in vivo resting and ejaculation pressures. Once the hydrogel material 1 is fully formed, the hydrogel material 1 seals the lumen L and prevents passage of sperm S or other materials.

In some embodiments, a method includes coupling a container assembly to a delivery member. The container assembly defines a first chamber and a second chamber, with the first chamber being fluidically isolated from the second chamber. The first chamber contains a first component and the second chamber contains a second component. The first component is formulated to be crosslinked with the second component to form a hydrogel. The first component and the second component are formulated such that the hydrogel has a gelation time. A portion of the first component and a portion of the second component are conveyed into a mixing volume of the delivery member and through the delivery member within a delivery time that is less than the gelation time. The first component crosslinks with the second component to at least partially form the hydrogel within the delivery member such that the conveying causes the hydrogel to be conveyed out of an exit opening of the delivery member.

In some embodiments, the hydrogel is conveyed out of the exit opening of the delivery member into or onto a body lumen, cavity, tissue, or organ to at least partially occlude the body lumen, cavity, tissue, or organ. In some embodiments, the lumen, cavity, tissue, or organ is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space. In some embodiments, the hydrogel can additionally or alternatively provide contraceptive effect to a subject or induce azoospermia or infertility in a subject.

In some embodiments, the conveying of the first component and the second component to the mixing volume includes conveying equal parts of the first component and the second component. In some embodiments, the conveying of the first component and the second component to the mixing volume includes conveying more of the first component than the second component, or more of the second component than the first component.

In some embodiments, the first component and the second component are formulated such that a viscoelastic substance is conveyed out of the exit opening of the delivery member.

In some embodiments, the first component and the second component are formulated to have an initial storage modulus (initial G') and an initial loss modulus (initial G") when the first component and the second component are initially combined. A ratio of the initial G" to the initial G' is between about 5 and about 100. The first component and the second component are formulated to have a delivered storage modulus (delivered G') and a delivered loss modulus (delivered G") when the first component and the second component are conveyed out of the delivery member (e.g., at the delivery time). A ratio of the delivered G" to the delivered G' is between about ⅓ and about 3. In some embodiments, the ratio of the initial G" to the initial G' is between about 30 and about 5 and the ratio of the delivered G" to the delivered G' is between about ⅓ and about 1. In some embodiments, the first component and the second component are formulated to have a gelation storage modulus (gelation G') and a gelation loss modulus (gelation G") after the gelation time and a ratio of the gelation G" to the gelation G' being less than about 0.2. In some embodiments, the ratio of the gelation G" to the gelation G' is about 0.1.

In some embodiments, the first component is at least one of a polyvinyl alcohol, alginate or modified alginate, chitosan or modified chitosan, polyethyleneimine, carboxymethyl cellulose, and/or polyethylene glycol terminated with a biorthogonal functional group (e.g., amine, thiol, maleimide, azide, activated ester). The second component is at least one of a water or buffer, water or buffer with divalent cations such as calcium, a solution of reduced hyaluronic acid, a solution of polystyrene sulfonate, a solution of gelatin, and/or polyethylene glycol terminated with a biorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent, such as about 2 to 10%, about 3 to 12%, about 4 to 15%, about 5 to 20%, about 6 to 25%, or about 7 to 28%, or any range in between any of these endpoints. In some embodiments, the polysaccharides may be modified with one or more functional groups, such as the same or different functional groups. For example, the functions groups may include one or more of alcohols, amines, thiols, carboxylic acid, carboxylic acid derivatives, carbonates, carbamates, carbamides, alkanes (n=2 to n=12), alkenes, maleimides, sulfones, vinyl sulfones, and activated carboxylic acids.

In some embodiments the polysaccharides and proteins may range in molecular weight from about 10,000 to about 1,000,000 grams/mole, such as about 15,000 to about 900,000 grams/mole, about 20,000 to about 850,000, about 25,000 to about 800,000, about 30,000 to about 700,000, about 50,000 to about 600,000, about 75,000 to about 500,000, about 100,000 to about 400,000, about 200,000 to about 300,000, or about 225,000 to about 275,000. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from about 1,000 to about 1,000,000 grams/mole such as about 1,500 to about 900,000 grams/mole, about 2,000 to about 850,000, about 2,500 to about 800,000, about 3,000 to about 700,000, about 5,000 to about 600,000, about 7,500 to about 500,000, about 10,000 to about 450,000, about 15,000 to about 50,000, about 100,000 to about 400,000, about 200,000 to about 300,000, or about 225,000 to about 275,000, or any range in between any of these endpoints.

In some embodiments, the dissolving solution for the polymer component(s) may be aqueous buffers, including any one or more of phosphate, citrate, acetate, histidine, lactate, tromethamine, gluconate, aspartate, glutamate, tartrate, succinate, malic acid, fumaric acid, alpha-ketoglutaric, and/or carbonate. Specific solvents/buffers can include: 1) acetic acid and sodium acetate (AA), 2) citric acid and sodium citrate (CP), 3) citric acid and phosphate buffer (CP), and 4) phosphate buffer (PB). Non-aqueous solvents include: dimethyl isosorbide, glycofurol 75, PEG 200, diglyme, tetrhydrofurfuryl alcohol, ethanol, acetone, solketal, glycerol formal, dimethyl sulfoxide, propylene glycol, ethyl lactate, N-methyl-2-pyrrolidone, dimethylacetamide, methanol, isopropanol, 1,4-butanediol, ethyl acetate, toluene, acetonitrile. The molarity of the solutions/solvents/buffers can range for example from about 0.1 M to about 0.15 M to about 0.2 M, such as about 0.12 M to about 0.17 M to about 0.19 M, or any range in between any of these endpoints. In some embodiments, the solution can include about a 0.2 M citric acid buffer and can be formulated to have a solution pH of between 4.0 and 6.0. In some embodiments, the pH of the solution can be between 4.0 and 5.25. In some embodiments, the pH of the solution can be about 4.0. In other embodiments, the pH of the solution can be about 5.25. In yet other embodiments, the pH of the solution can be between about 4.5 and about 8 such as a pH of about 5-7, or about 4.5-6.

The term "about" when used in connection with a referenced numeric indication means the referenced numeric indication plus or minus up to 10% of that referenced numeric indication. For example, "about 100" means from 90 to 110.

The term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range.

As used herein, the term "biomaterial component" (also referred to as "component") includes any substance that is used in connection with any of the systems or delivery devices described herein to form a delivered biomaterial product. For example, a component can include a small molecule, catalyst, peptide, protein, enzyme, nucleotide (or derivatives of), short chains of nucleotides (or derivatives of), long chains of nucleotides (or derivatives of), monosaccharides (or derivatives of), disaccharides (or derivatives of), trisaccharides (or derivatives of), oligo saccharides (or derivatives of), polysaccharides (or derivatives of), monomer, oligomer, macromer, or polymer that can be crosslinked with another component to form a delivered product (e.g., hydrogel). A component can include a mixture or solution of one or more constituents (e.g., a polymer and a solvent). A component can include such constituents regardless of their state of matter (e.g., solid, liquid or gas). A component can include both active constituents and inert constituents. For example, in some embodiments, a component can include certain polymers that can form a delivered product, as well as a medicament or other active ingredient. By way of another example, in some embodiments a component can include drugs, including but not limited to, small molecule drugs and biologics. In other embodiments, a component can include certain constituents to impart desired properties to the delivered product, including constituents that facilitate the delivered product being echogenic, radiopaque, radiolucent, or the like.

The term "biomaterial product," "delivered biomaterial product," or "delivered product" includes any substance that is delivered by any of the systems or delivery devices described herein. For example, a delivered product can a biomaterial that is formed from multiple biomaterial components and delivered with any of the delivery systems described herein and then delivered to target locations. Thus, a delivered product can be the implant or structure that is at least partially formed with the system by multiple biomaterial components that react together or assemble into higher order structures via covalent and/or non-covalent bonds, and that is delivered by the system. For example, in certain situations, the delivered product can have a storage modulus (delivered G') and a loss modulus (delivered G") when the first component and the second component are conveyed out of a delivery member. The ratio of the delivered G" to the delivered G' can between about ⅓ and about 3. In some embodiments, the delivered G' can be greater than the delivered G" (i.e., the ratio of the delivered G" to the delivered G' is less than one), thus indicating that the delivered product is more solid than liquid. In some embodiments, the components can be formulated such that a viscoelastic substance (and not a liquid substance) is conveyed out of the exit opening of the delivery member.

In certain situations, the biomaterial can be delivered by the system in a fully formed state to a target location. Although a delivered product can be considered fully formed (i.e., the chemical reactions between the biomaterial components are completed), it can still undergo certain changes (e.g., in vivo changes) after delivery. For example, a delivered biomaterial product can continue to absorb water and/or swell and/or can expel impurities. In some embodiments, a delivered biomaterial product can be a hydrogel that is formed by crosslinking of two or more biomaterial components. The term "hydrogel" can refer to any water-swollen (majority, >50%, of material mass is water), and cross-linked polymeric network produced by the reaction of one or more components (e.g., polymers, monomers) and/or a polymeric material that exhibits the ability to swell and retain a significant fraction of water within its structure, but will not dissolve in water.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

The term "gelation" refers to the transition of the hydrogel components from a soluble polymer of finite branches to a substance with infinitely large molecules. Similarly stated, "gelation" refers to the condition where the gel forms and after the components are combined. Thus, the gelation time refers to the time that it takes for the resulting hydrogel to substantially reach equilibrium.

Formulations and Test Results

Specific design parameters were identified and selected for a vas-occlusive hydrogel formulation for delivery with low injection forces that rapidly form strong, viscoelastic materials that swell to enable occlusion while withstanding in vivo resting and ejaculation pressures. Although the vas was selected for these examples, the formulations are applicable to other applications, body parts, lumens, cavities, tissues, and organs as well. These selected formulations were further developed and tested with three different aqueous carrier solvents that resulted in a broad range of gelation times. As described further herein, these three systems use the same polymer constituents but have different gelation times. Mechanical characterization of this material via rheology, compression testing, and fatigue testing indicated that is the embodiments described herein are capable of withstanding the dynamic environment of the vas, while still occluding sperm. Biocompatibility of the hydrogel was demonstrated with a mammalian cell line and human sperm. Injections of the hydrogel into cadaveric canine vas demonstrated the feasibility of implantation of the compositions described herein via the methods described herein. The injected hydrogel material occluded the lumen without damaging the vessel wall, and was able to withstand 100× ejaculation pressure.

As described herein, three injectable hydrogel systems based on three separate formulations are identified for vas-occlusive performance. However, it will be appreciated that these three formulations, and other formulations identified herein, can be used in or with other body lumens, cavities, tissues or organs. Such body lumens, cavities, tissues or organs can include an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space. The formulations for the three injectable hydrogel systems (also referred to collectively as three systems, or individually as Fast System, Intermediate System, and Slow System) includes two reactive polymeric hydrogelators in an aqueous carrier solvent that are combined at the time of injection in a delivery device (e.g., the delivery device 1100 described herein) and form a covalently crosslinked hydrogel network. The three formulations using these polymer systems have been assessed to be good candidates for vas-occlusive applications based on the following criteria: gelation time, injection force, delivery mass, swelling ratio, and immediate mechanical properties.

Figure 2A:
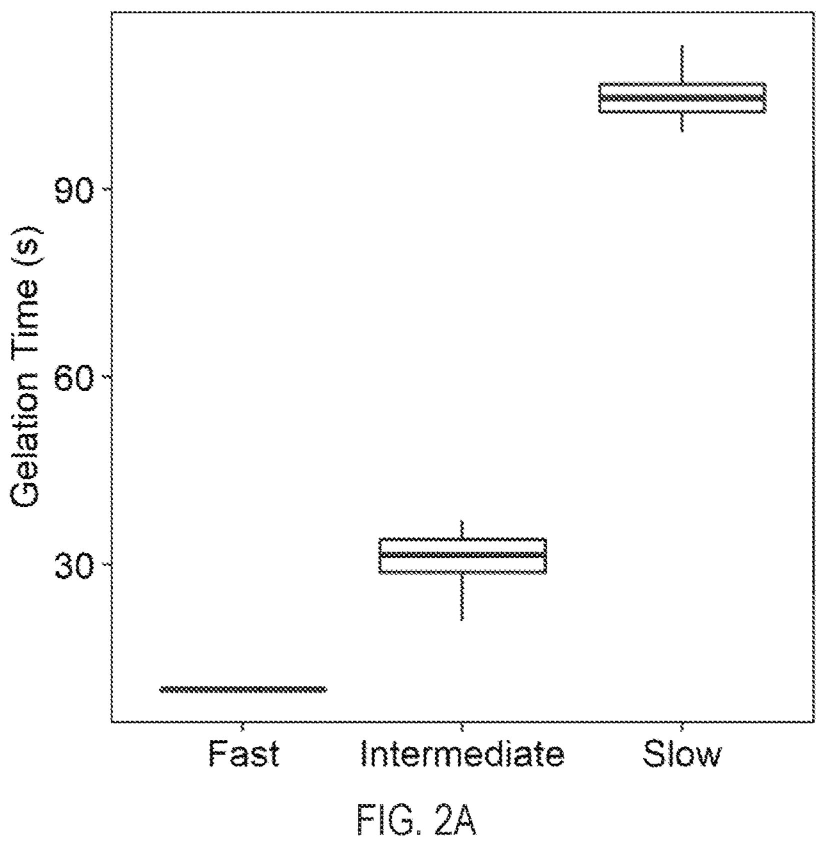
FIG. 2A is a plot showing gelation times of Fast, Intermediate and Slow Hydrogel Systems in a tilt vial experiment.

Gelation time is an important variable to consider for an injectable hydrogel, especially when it is used to occlude a pressurized vessel like the vas. The gelation time has an impact on clinically relevant properties of an injectable hydrogel and its use as an occlusive material. Tilt vial experiments were used to assess gelation times of the formulations described herein. In these experiments 100 μL hydrogels were injected into 2-mL vials and lightly tilted from 0° to 45° until no flow was observed. The injected volume was selected based on previous reports indicating that it is suitable for vas-occlusion in humans and animals using injectable polymeric materials. As shown in FIG. 2A, by adjusting the carrier solvent, the macroscopic gelation time can be adjusted from substantially instantaneous to greater than 1.5 minutes. The Fast System has a gelation time of less than 10.0 seconds, which is shorter than the injection or delivery time of the 100 μL hydrogel. The Intermediate System has a gelation time of about 30.0±5.0 s, with a gelation time range of 21.0 s to 37.0 s, which is ~2.5 times longer than the time required for injection. The Slow System has gelation time of about 105.0±4.6 s, with a gelation time range of 99.0 s to 113.0 s, which is >5 times longer than the time required to deliver the implant.

Figure 2B:
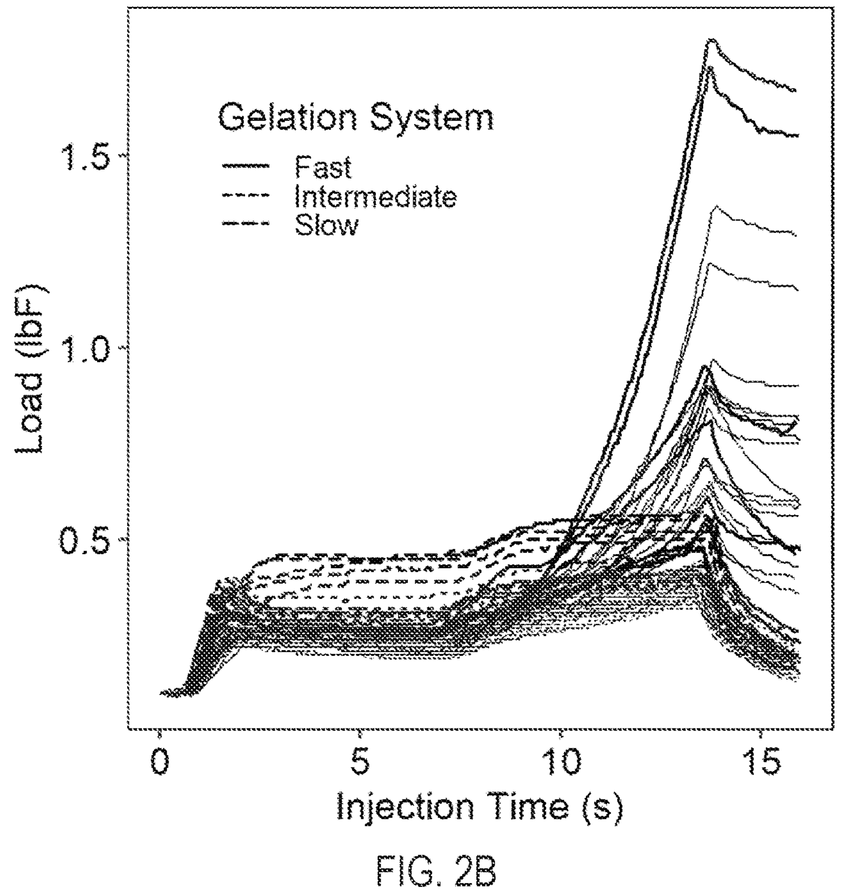
FIG. 2B is a plot showing extrusion forces of the Fast, Intermediate and Slow Hydrogel Systems injected into tubing or into vials according to an embodiment.

With the three systems that spanned gelation times from immediate to minutes identified, the impact of gelation time on injection force (i.e., the force with which the compositions are delivered; also referred to herein as the extrusion force) was examined. The force of injection is an important variable to consider since high injection forces can result in unexpected pauses during injection that create non-uniform implants and result in a poor injection experience for the user. Additionally, for an occlusive material, higher injection forces can damage the body lumen or vessel wall. For example, a higher injection force may scar or tear the target tissue. Peak injection forces of the Slow, Intermediate, and Fast Systems were measured during controlled injections (using our delivery system) of 100 μL hydrogels into 2-mL vials as well as into 0.8 mm inner diameter PTFE tubing. This PTFE tubing is similar to the average human vas inner diameter (0.5-1.4 mm inner diameter). These two experimental injection systems were used to investigate if there was a difference of forces when the hydrogel systems were injected in an open space (vial) versus confinement (tubing). As shown in FIG. 2B, the Intermediate and Slow Systems injected into 2-mL vials displayed similar average peak extrusion forces of 1.87±0.18 N (0.42±0.04 lbF) and 2.40±0.58 N (0.54±0.13 lbF), respectively. A slight decrease in extrusion forces was observed when injecting into confinement of the 0.8 mm inner diameter PTFE tubing, with average extrusion forces being 1.82±0.31 N (0.41±0.07 lbF) and 1.73±0.27 N (0.39±0.06 lbF) for the Intermediate and Slow Systems, respectively. Peak extrusion force observed for the Fast System was more than two times higher than that for the Intermediate System in both the vial and tubing experimental injection systems. For the Fast System, the average peak extrusion forces were 4.14±2.40 N (0.93±0.54 lbF) in vials and 3.74±1.02 N (0.84±0.23 lbF) in 0.8 mm inner diameter tubing. All three systems displayed extrusion forces that would be indistinguishable by the human hand (e.g., if a manual delivery system is used). These results show that a lower force of injection is observed when the gelation time is greater than the time required for injection. Furthermore, for the systems contemplated herein, there is minimal difference of injection force when the material is delivered to a free space (vials) versus a confined space (tubing), which was unexpected.

Figure 2C:
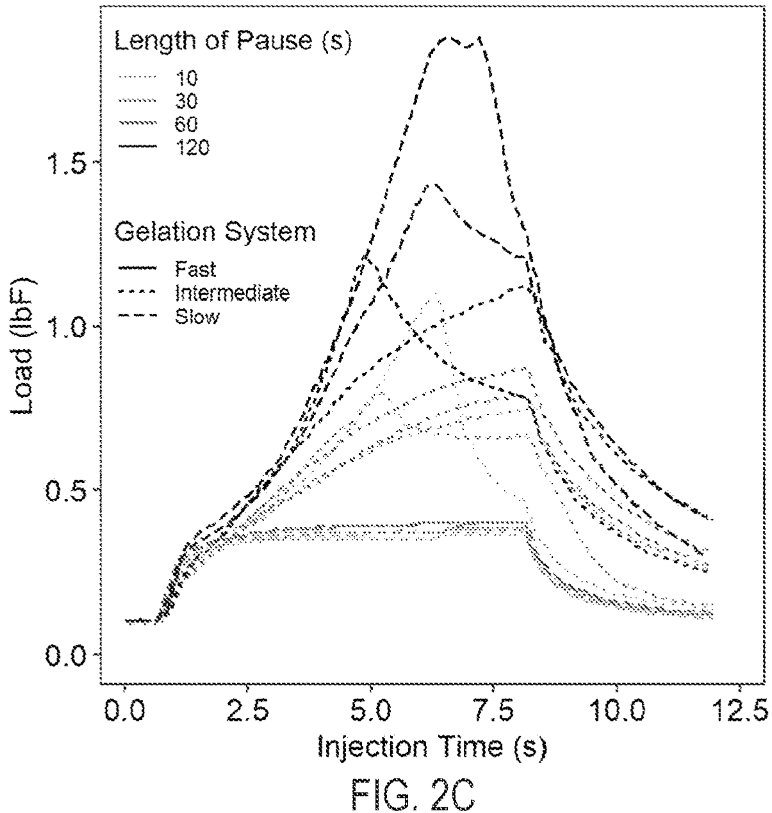
FIG. 2C is a plot showing duration of pause mid-injection that can be achieved with the Intermediate and Slow Hydrogel Systems without exceeding forces of 8.9 N (2 lbF) according to an embodiment.

In some embodiments, the two component hydrogel forming the occlusive product or implant is mixed in situ or at the point of injection. In some cases, a physician or technician may want to pause the injection if complications are observed, such as if there is needle or catheter slippage or bleeding. The ability to pause mid-injection for different durations using the three systems was examined. As shown in FIG. 2C, the Slow and Intermediate Systems were tested and could be paused mid-injection for up to 90 seconds while maintaining injection forces lower than 22.24 N (2 lbF). In particular, testing was conducted using pauses of 10 seconds, 30 seconds, 60 seconds, and 120 seconds on the Slow and Intermediate Systems. The Fast System was not tested under these conditions since this system has a gelation time of about 10 seconds, but under other scenarios the Fast System can be paused for periods of less than 10 seconds, or may be paused a duration of 10 seconds or more if injection forces do not need to be maintained at or below 22.24 N (2 lbF). This analysis shows how the gelation time can affect certain potential clinical situations, specifically pausing mid-delivery, while still being able to deliver the entire two component hydrogel payload without having to exchange the needle or catheter.

Figure 2D:
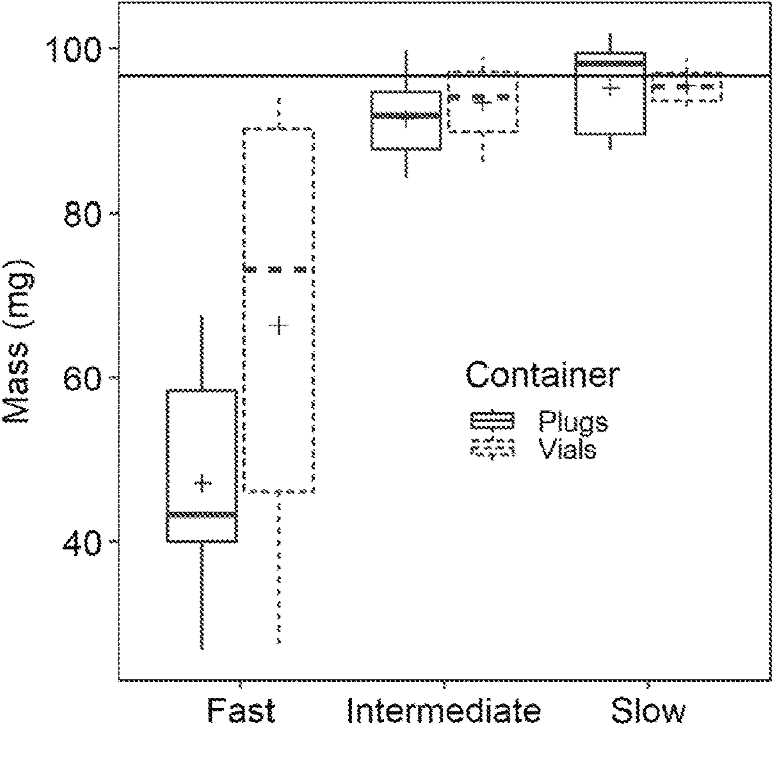
FIG. 2D is a plot showing mass of the Fast, Intermediate and Slow Hydrogel Systems extruded into tubing or into vials according to an embodiment.

For an occlusive product, it is important that injections deliver the required amount of hydrogel to form an efficacious occlusion. A gravimetric analysis was conducted to quantify the accuracy and precision of delivering hydrogels into vials and into an 0.8 mm inner diameter PTFE tubing for all three systems. As shown in FIG. 2D, the Fast System delivered less than the targeted mass range of 80-100 mg, whereas in the Intermediate and Slow systems, the targeted mass range was achieved. For the Fast System, the hydrogel mass range in vials was between about 48.5 mg to about 87 mg and hydrogel mass range in tubing was about 39.5 mg to about 58 mg. For the Intermediate System, the hydrogel mass range in vials was between about 88.7 mg to about 98.2 mg and hydrogel mass range in tubing was about 86.8 mg to about 96.1 mg. For the Slow System, the hydrogel mass range in vials was between about 93.4 mg to about 97.6 and hydrogel mass range in tubing was about 89.9 mg to about 100.5 mg. The decrease in delivered mass for the Fast System can possibly be attributed to the removal of hydrogel material with the injection device (also referred herein as a delivery device) after completion of injection. Specifically, material was still attached to the tip of the needle/catheter when it was removed from the mouth of the vial or the lumen of the tubing. Thus, these results show that the accuracy and precision of delivery is improved when the gelation time of the injectable hydrogel is at least 2.5 times more than the injection time.

Figure 2E:
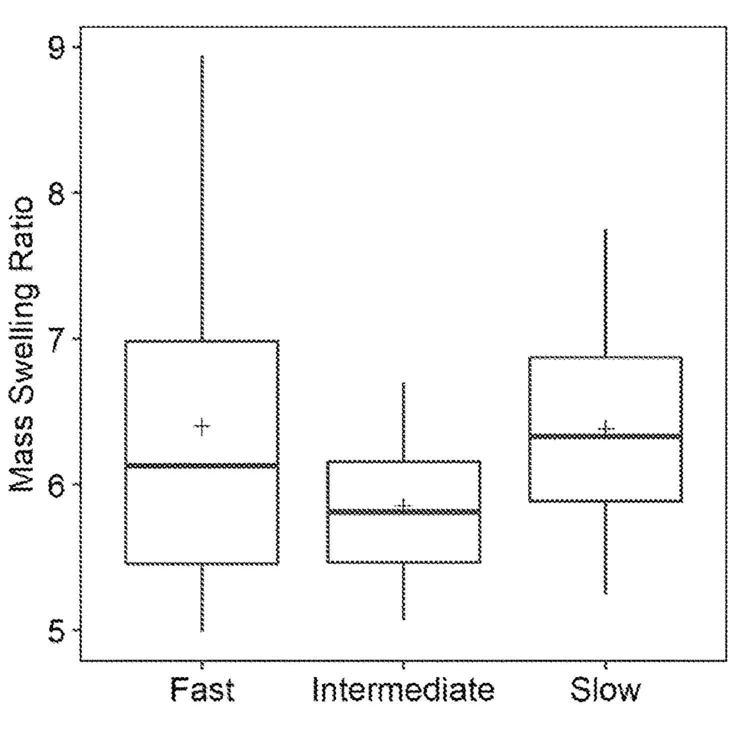
FIG. 2E is a plot of mass swelling ratio for the Fast, Intermediate and Slow Hydrogel Systems according to an embodiment.

The swelling ratio is a key parameter in designing an injectable occlusive implant. For example, the inner diameter of the vas can increase 1.5-3 times from rest to ejaculation. Therefore, a swelling ratio of >3 or >300% swelling is desired for a hydrogel to maintain an occlusion in the vas or other similar vessels. The equilibrium swelling ratios of the Fast, Intermediate, and Slow Systems are shown in FIG. 2E, and the hydrogel swelling was determined by mass and volume (ESI). To assess swelling, 100 μL hydrogels from all three systems were formed in 2-mL vials and then incubated with 1 mL pH 7.2 100 mM PBS for 72 hours at 37° C. After 72 hours, the three systems were imaged in the vials and the volume determined. Then the buffer was removed, and the swollen hydrogel mass was obtained. The Fast, Intermediate, and Slow Systems all produced hydrogels with equilibration volumes greater than five times the original injection volume. The swelling ratios by mass were determined to be 6.40±1.33 for the Fast System, 5.85±0.59 for the Intermediate System, and 6.38±0.83 for the Slow System. Interestingly, these results showed that the gelation time had minimal impact on the swelling properties and that all three systems swelled >300% via mass and volume, thus being suitable for an occlusive implant within the lumen of the vas.

Figure 2F:
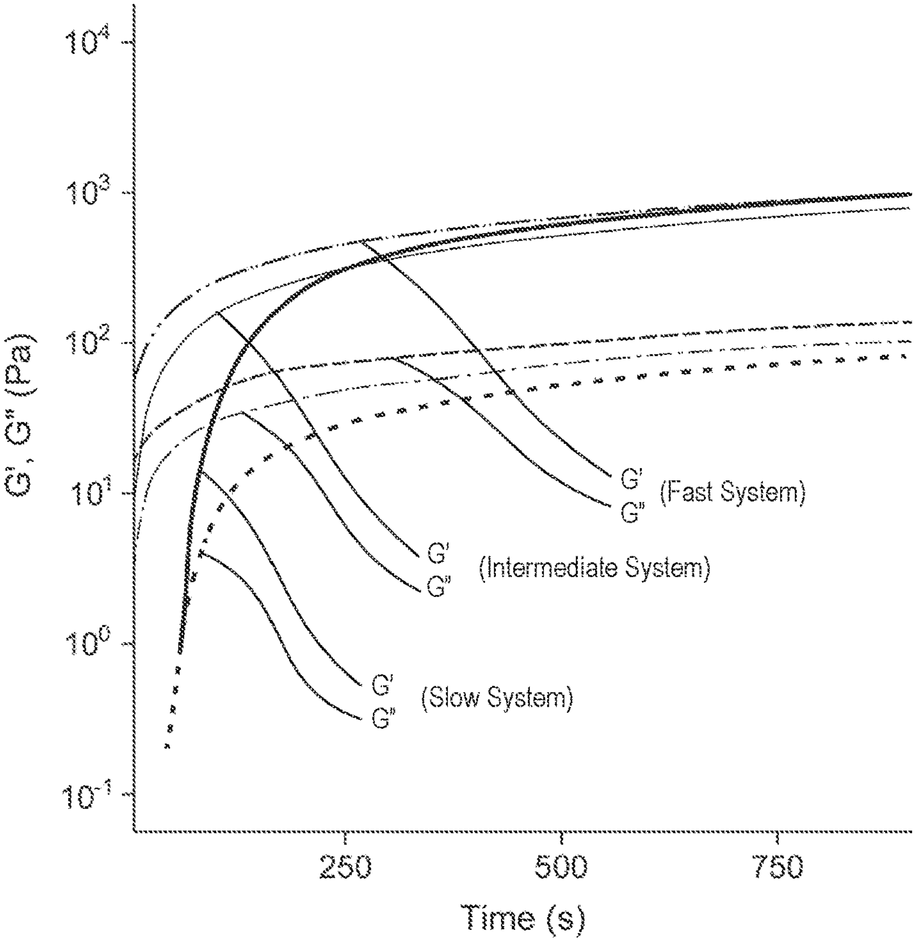
FIG. 2F is a plot of storage moduli and loss moduli over time for the for the Fast, Intermediate and Slow Hydrogel Systems.

In order to facilitate manipulation by the vas during ejaculation and avoid a mechanical stiffness mismatch that could result in muscle damage or poor implant compliance, a vas-occlusive hydrogel should be softer or as stiff as the smooth muscle tissue surrounding the vas. Oscillatory rheology time sweep measurements of Fast, Intermediate, and Slow hydrogels were conducted to investigate network formation kinetics and mechanical properties immediately after injection. Time sweep measurements were performed by injecting Fast, Intermediate, and Slow hydrogels between a parallel plate geometry (8 mm diameter) set at a 0.8 mm gap. Rheological measurements at a constant oscillation frequency of 5 rad/s and oscillation strain of 5% were started immediately after injection onto the stage and beneath the geometry. As shown in FIG. 2F, the Fast and Intermediate systems are viscoelastic materials before the first time point is measured (G'>G"), whereas the Slow system displays a G'–G" crossover at approximately 40 s. Stated in another way, the Fast and Intermediate Systems experience a G'–G" crossover and each becomes a viscoelastic material prior to exiting the injection device. The G' and G" values of all three systems begin to converge at ~250 s. After 10 minutes of measurement, all three gelation systems display similar G' (~$10^3$ Pa) and G" (~$10^2$ Pa) values. This indicates that the gelation time does not impact the mechanical properties in the minutes after injection, and that all three systems are as stiff or softer than the vas muscle tissue. Thus, all three systems reduce complications due to a stiff intraluminal material that could damage the vas.

Figure 3A:
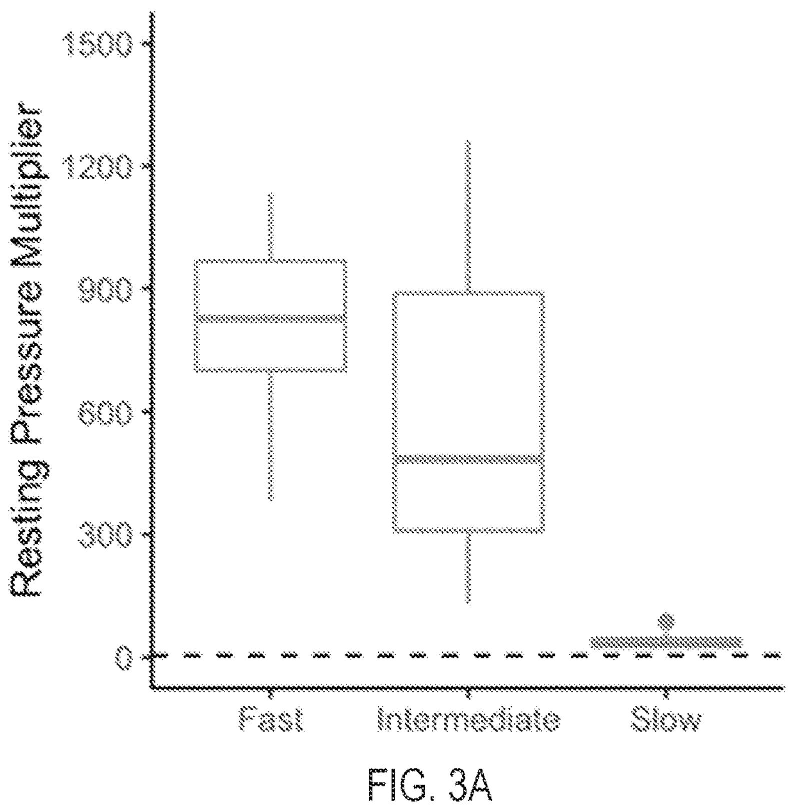
FIG. 3A is a plot of resting burst testing pressures experienced by the Fast, Intermediate and Slow Hydrogel Systems relative to resting pressures of the vas according to an embodiment.
Figure 3B:
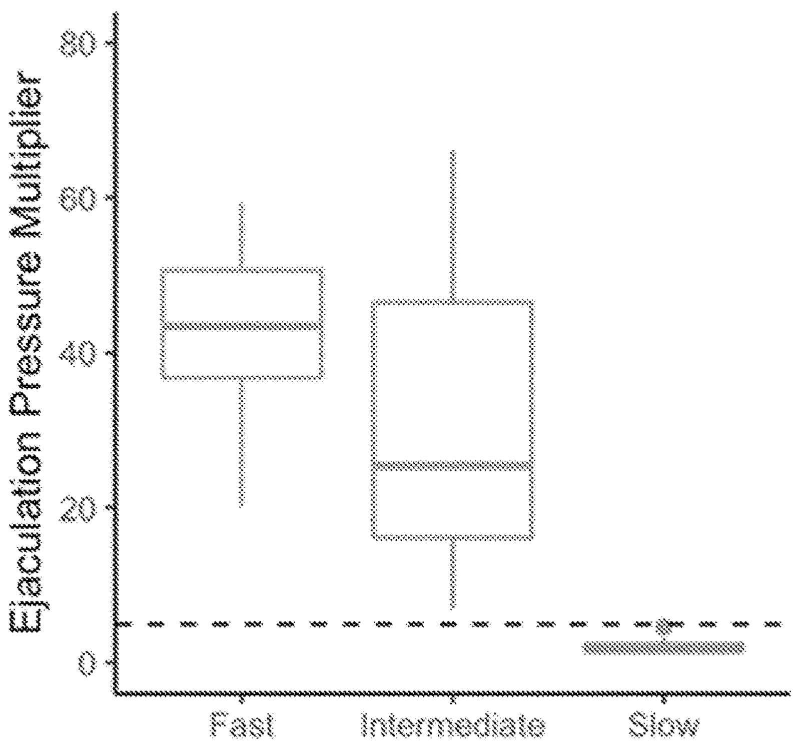
FIG. 3B is a plot of ejaculation pressures experienced by the Fast, Intermediate and Slow Hydrogel Systems relative to ejaculation pressures of the vas according to an embodiment.

Implanted hydrogels for vas-occlusive contraception must be able to immediately withstand the in vivo pressures of the vas. At rest, the intraluminal pressure of the canine vas is ~11 $cmH_2O$. During ejaculation, the intraluminal pressure can reach as high as 210 $cmH_2O$. These pressure values are conserved across other mammals and therefore we reasoned that the human vas, which is similar in vessel thickness and inner diameter to the canine, would have similar intraluminal pressures. To test the efficacy of the implant, i.e., ability to withstand in vivo pressures, an in vitro burst test experiment was conducted. Each of the hydrogel systems were injected into vas mimetic PTFE tubing and subjected to hydraulic pressure with an experimental shutoff at 100× in vivo ejaculation pressure. There are two possible results of this testing: 1) the hydrogel experiences the 100× pressure event and maintains its position in the tubing and 2) the hydrogel experiences the 100× pressure event and moves/migrates within the tubing or is completely extruded before reaching the 100× cutoff. If scenario 2 occurs then the pressure at which the implant moves is recorded as the failure pressure. For the purposes of burst testing, PTFE serves as a worst-case-scenario since it is devoid of surface features and is non-interacting with the hydrogel. For all three systems, 100 μL hydrogels were injected into 0.8 mm inner diameter PTFE tubing. Within 10 minutes of injection, the hydrogel filled tubes were fitted with a syringe loaded with 1-mL of saline solution and saline was flowed into the tube at 0.2 mL/minute while measuring the force applied to the saline plunger. The measured forces were converted to the pressure experienced by the plug and the data is reported in terms of resting and ejaculation pressures multipliers. As shown in FIG. 3A, the Fast, Intermediate, and Slow Systems were able withstand resting pressure multipliers of 809±240, 591±403, and 42.0±22.0, respectively. As shown in FIG. 3B, the Fast, Intermediate, and Slow Systems were able withstand ejaculation pressure multipliers of 42.4±12.6, 30.9±21.1, and 2.20±1.15, respectively. All three systems can withstand pressures >40 times the resting pressure of the vas immediately after implantation. Furthermore, all three systems were able to withstand >2 times ejaculation pressure immediately after implantation. These data show that gelation time has a significant impact on how much pressure the hydrogel can withstand immediately after implantation, with the faster gelation times being able to withstand higher pressures.

Figure 3C:
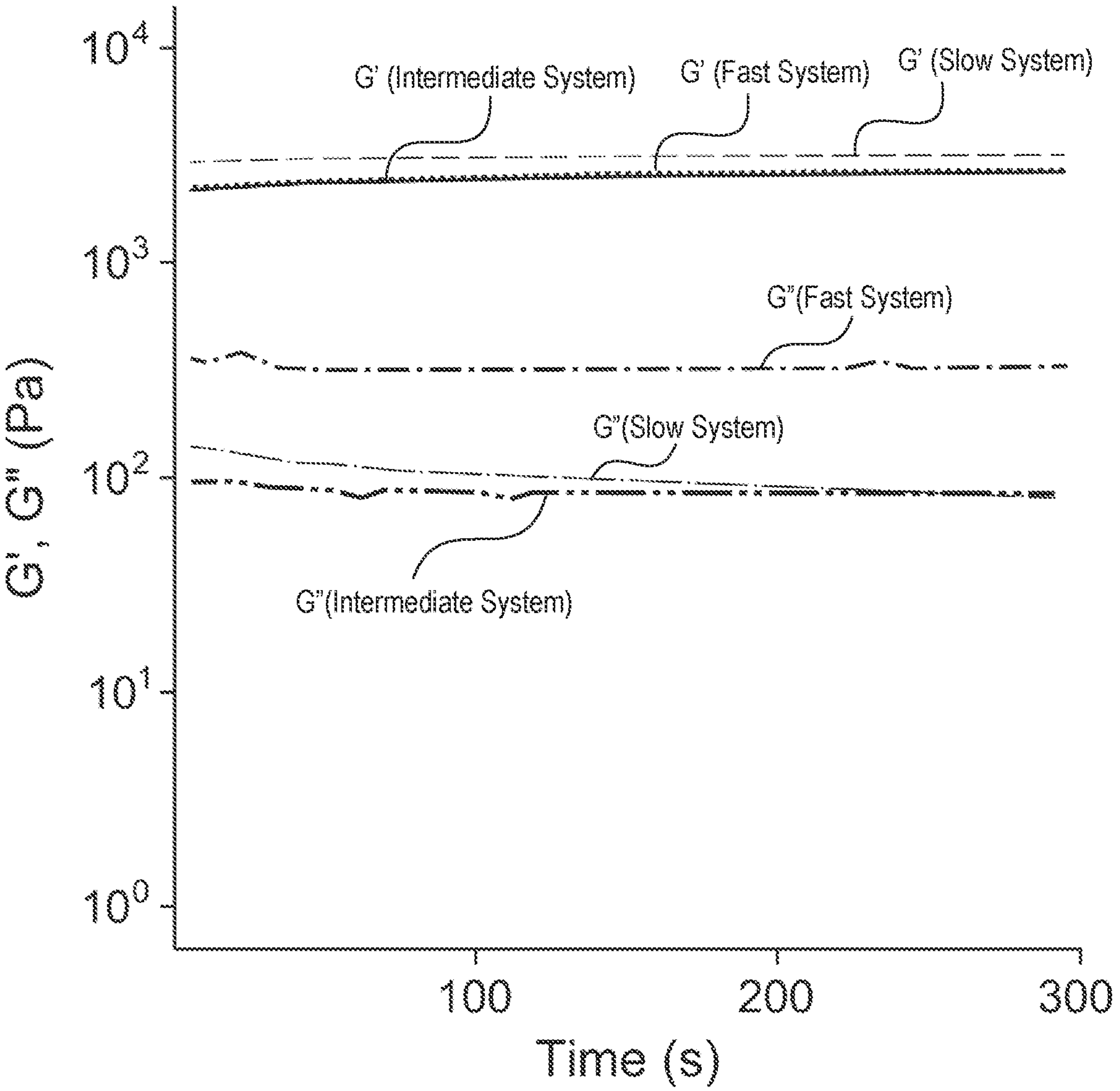
FIG. 3C is a plot showing a time sweep rheology of enubilated hydrogels for the Fast, Intermediate and Slow Hydrogel Systems according to an embodiment.

Additional experimentation demonstrated that all three systems had similar mechanical properties when directly injected onto the rheometer after 250 s. As a result of the differences in resistance to pressure, an investigation was conducted to see if a difference was observed in the equilibrium mechanical properties using oscillatory rheology. To obtain swollen hydrogels for rheology, 100 μLhydrogels were formed in 2-mL vials then incubated with 1-mL of pH 7.2 100 mM PBS for 72 hours at 37° C. As shown in FIG. 3C, time sweeps were then conducted at a constant oscillation frequency of 5 rad/s and oscillation strain of 5%. Average tan(delta) values for the Fast, Intermediate, and Slow Systems were 0.13, 0.034, 0.032, respectively. The high tan(delta) of the Fast System can be attributed to the heterogeneous nature of the Fast System hydrogel network, which gels substantially instantaneously upon injection. All these values were within the desired range. Based on this information and the performance of the Intermediate System's gelation time, injection force, paused injection, delivery mass, and immediate burst testing, additional studies of the Intermediate system were conducted. Specifically, the study set out to determine whether it was possible to accurately deliver the Intermediate System and have it withstand >30 times ejaculation pressure immediately after injection.

Figure 4A:
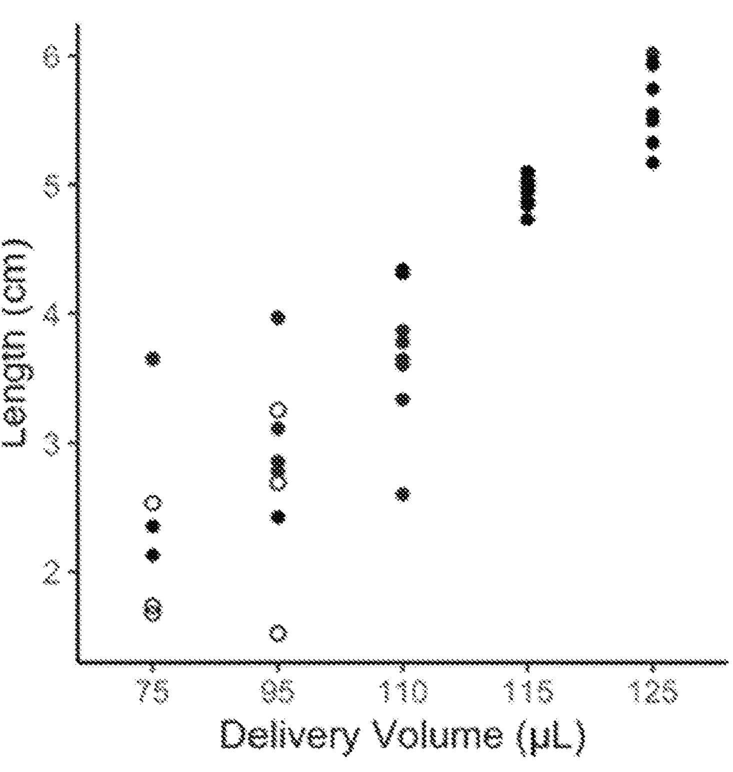
FIG. 4A is a plot of volume screening of the Intermediate Hydrogel System to show minimum efficacious delivery volume according to an embodiment.

As discussed above, the 100 μL of the Intermediate System was able to withstand immediately after injection. Next, the minimum volume of implant required to withstand in vivo ejaculation pressures in the vas was determined. Vasectomy is a minimally invasive outpatient procedure, where most patients experience tenderness up to 72 hours after the procedure. Based on review, the Intermediate System equilibrates within 8-12 hours. Therefore, it was reasoned that the earliest that an implant based on the Intermediate System could experience ejaculation pressures would be 72 hours post-implantation. Different volumes (75 to 125 μLs) of the Intermediate System were injected into 1.4 mm ID tubing (maximum in vivo inner diameter), followed by plug burst/pressure testing with a 100× ejaculation experimental cutoff. The volumes were implanted in the lumen of the tubing, placed in contact with solution and incubated at 37° C. for 72 hours. As shown in FIG. 4A, an implant that passes (closed/solid circle) is able to maintain its position in the tube after experiencing 100× ejaculation pressure, while a failed implant (open circle) migrates or is extruded from the tubing prior to experience the 100× ejaculation pressure. It was observed that delivery volumes targeting <95 μL have failures, whereas delivery volumes >100 μL have no failures. Based on this testing, it was determined that the minimum volume of the Intermediate System is 100× in order for it to be able to withstand 100× in vivo ejaculation pressure. The 100 μL volume is easily injectable, has a high swelling ratio, functions as an occlusion immediately after injection, and has mechanical properties softer than the vas.

Figure 4B:
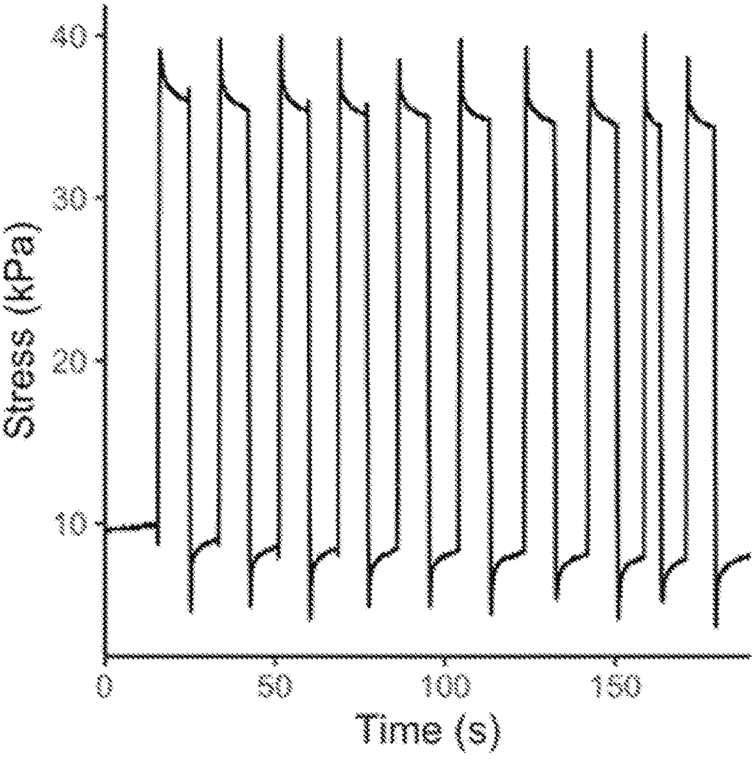
FIG. 4B is a plot showing compression testing of the Intermediate Hydrogel System according to an embodiment.

The vas is different than most vessels in the body. Structurally, it contains three layers of muscle tissue resulting in vessel wall that is 1-3 mm thick and an inner diameter that ranges from 0.5 mm to 1.4 mm at rest to ejaculation, respectively. This lends to a unique environment where at rest an intraluminal vas implant would experience pressures of 5-15 $cmH_2O$ and 200-250 $cmH_2O$ during ejaculation. However, the volume of space can change dramatically due to luminal expansion and contraction during ejaculation events. An in vivo ejaculation event consists of 8-12 pulses over a 10-30 seconds, during which the vas lumen is dynamically changing as it pumps sperm against gravity toward the ejaculatory duct. A series of experiments were conducted to investigate the responsiveness of the Intermediate System under similar forces and situations experienced within the vas. Uniaxial compression testing was performed on the Intermediate System in aqueous media at 37° C. to determine the elastic modulus. The hydrogel based on the Intermediate System was extruded between two steel plates with a gap 0.8 mm and equilibrated in an aqueous bath at 37° C. for 72 hours. In particular, as shown in FIG. 4B, uniaxial compression testing was performed on the Intermediate System. 100 μL of hydrogel was injected into an 800 μm gap M5-20 force gauge (Mark-10) attached to an ESM-303 force gauge (Mark-10) stand interfaced with MESURgauge software (Mark-10). The force gauge stand stage was fitted with a custom-built heated solvent reservoir. The hydrogel was submerged in pH 7.2 100 mM PBS and allowed to swell for 72 h at 37° C. Force data was collected throughout testing at a sampling rate of 20 Hz. The Intermediate System hydrogel was subjected to 10 successive cycles of compression and decompression of 5 N and 0.5 N, respectively, with a dwell of 10 seconds between each event (test duration ~175 seconds). The Intermediate System showed viscoelastic behavior, and the non-linear stress vs. strain response fit a two-component Maxwell-Weichart model with $R^2$ values >0.95. The elastic modulus of the Intermediate System was determined to be 34.25 kPa, which is in the middle of the range for cardiac muscle (5-50 kPa), and on the lower end of skeletal muscle (5-170 kPa). These results align with the oscillatory rheology data and demonstrate that the Intermediate System is viscoelastic and has mechanical properties similar to muscle tissue.

Figure 4C:
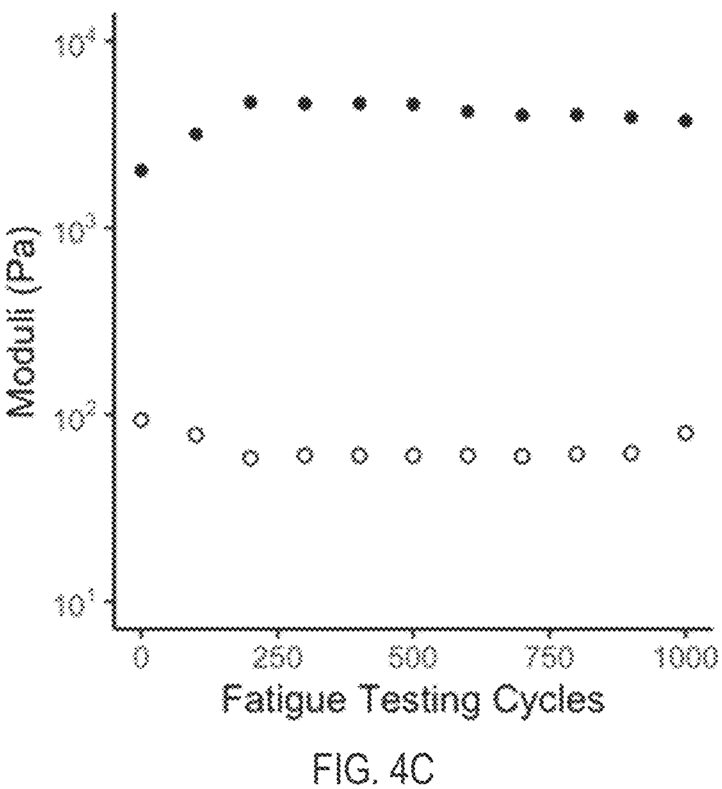
FIG. 4C is a plot showing rheological fatigue testing of the Intermediate Hydrogel System according to an embodiment.

Based on the positive viscoelastic response of the Intermediate System, two methods of fatigue testing using rheology and a pressurized tube-model were conducted to demonstrate that the implant would not build up or store energy over its lifetime since within the vas it will always be under some form of pressure and compression. Rheological fatigue testing was conducted on a swollen Intermediate System hydrogel in an aqueous bath at 37° C. to assess hydrogel mechanical properties after repeated high oscillation frequency and strain events. Rheological fatigue experiments were conducted by subjecting a hydrogel sample to 1,000 fatigue cycles. Each fatigue cycle consisted of a 30 s of high oscillatory frequency (20 rad/s) and strain (20%) event followed by a 30 s rest period at low oscillatory frequency (5 rad/s) and strain (20%). As shown in FIG. 4C, a 600 s time sweep was measured every 100 cycles during the 1000 cycle fatigue test showing the storage modulus G' (closed/solid circle) and the loss modulus G" (open circle).

Figure 4D:
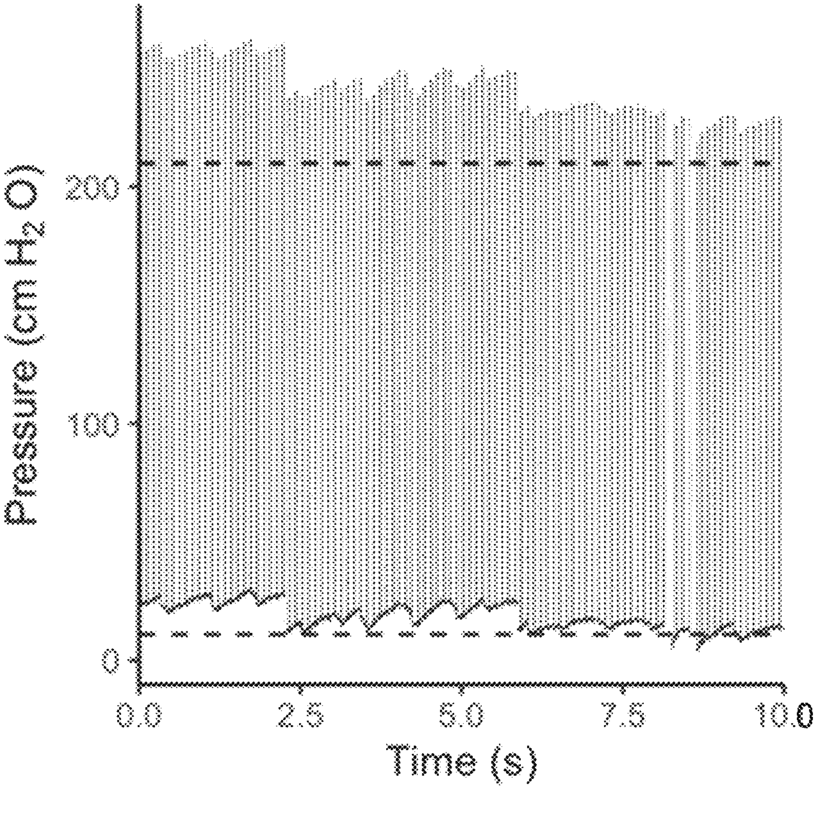
FIG. 4D is a plot showing fatigue testing of the Intermediate Hydrogel System within a model vas according to an embodiment.

Throughout the 1000 cycle test, the average storage modulus remains >2 kPa and the average loss modulus remains <100 Pa indicating minimal change in network structure throughout the test. For the pressurized tube-model, the Intermediate System hydrogels was injected into 0.8 mm inner diameter PTFE tubing, and equilibrated them in contact with aqueous media at 37° C. for 72 hours. This fatigue test was designed to mimic the scale and timing of pressure events within the vas during rest and ejaculation. To perform fatigue testing, the hydrogel filled tube was placed in-line with a pressure sensor and a syringe filled with saline. As shown in FIG. 4D, the syringe was placed on a syringe pump which was programed to infuse and withdraw solution repeatedly to mimic repeated ejaculation events >210 $cmH_2O$, while maintain a resting state pressure between these events. The upper dashed line at 210 $cmH_2O$ represents maximum ejaculation pressures while the lower dashed line at 11 $cmH_2O$represents resenting pressures. The Intermediate System hydrogel was capable of withstanding 100 simulated ejaculation events. Each ejaculation event consisted of 10 pressure pulses >210 $cmH_2O$ over 1 second with 10 of these decades occurring between 10-15 seconds; thus mimicking the timescale and pressures of ejaculation. Throughout the pressurized fatigue testing, no deviations in pressure measurement were observed and the position of the hydrogel in the tubing did not change indicating that the hydrogel did not migrate during the experiment. The pressurized fatigue test demonstrated that the Intermediate hydrogel system does not accumulate energy and resists macroscopic deformation due to hydraulic forces. The rheological fatigue testing showed that the network's structural fidelity remains after repeated high strain insults. Together, these fatigue tests indicated that the Intermediate system hydrogel is capable of resisting pressures and strains present in the vas.

Figure 5A:
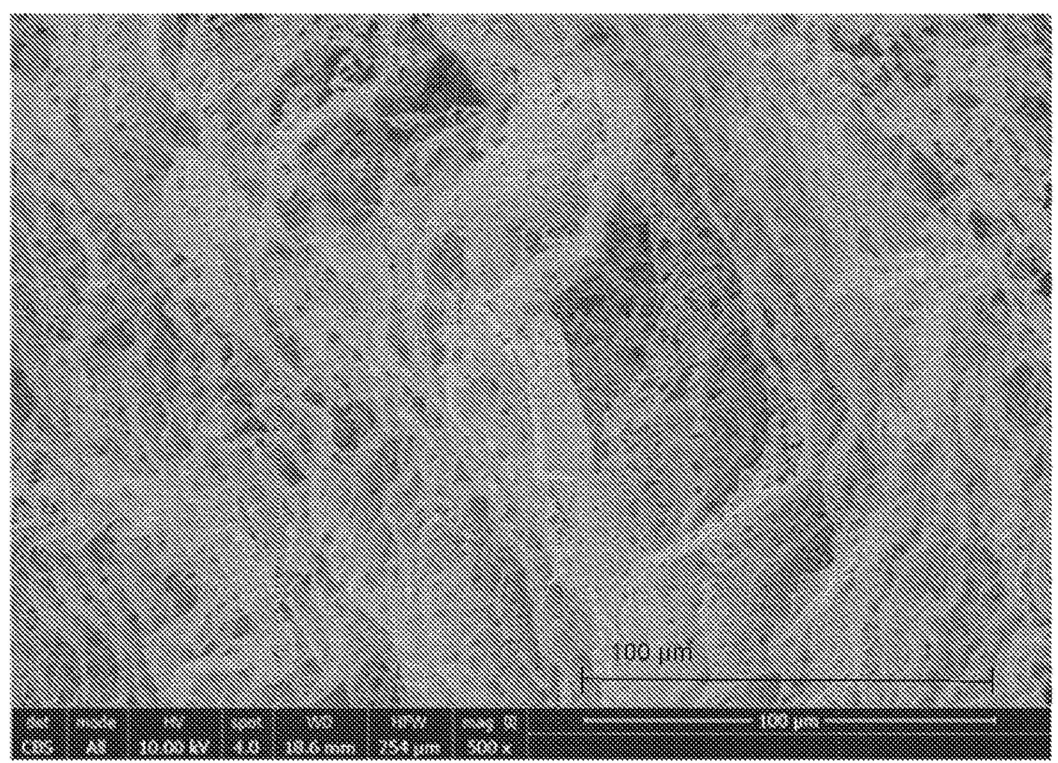
FIG. 5A is a photo of a scanning electron microscopy (scale of black bar is 100 μm) of lyophilized hydrogel of the Intermediate Hydrogel System according to an embodiment.
Figure 5B:
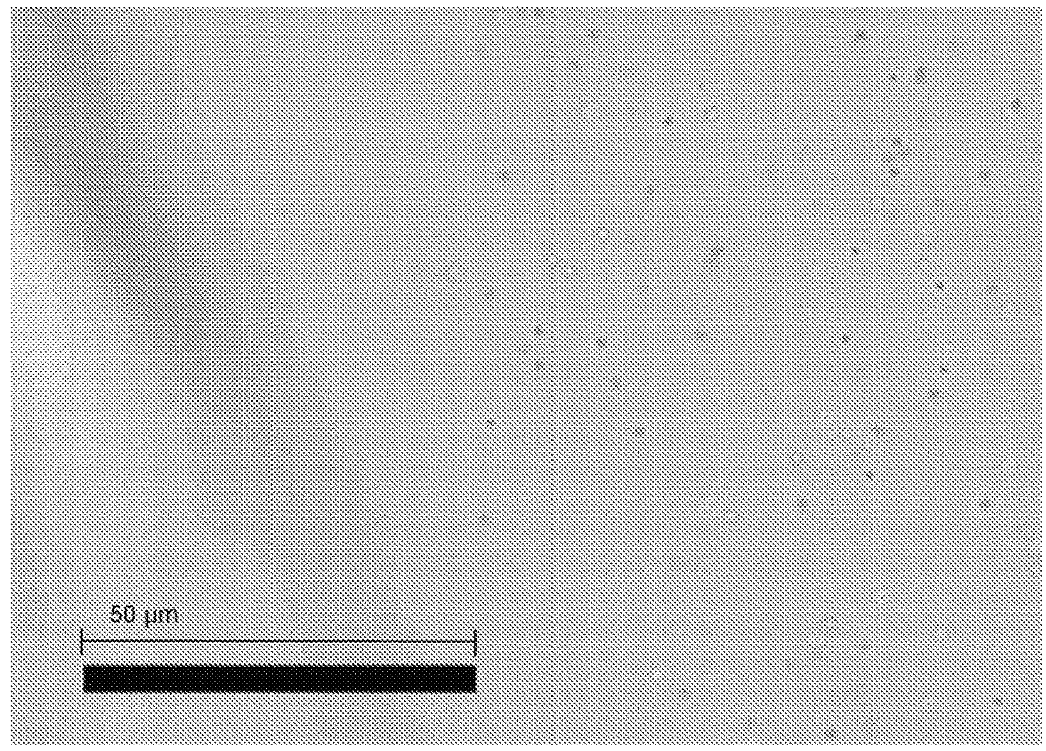
FIG. 5B is a photo of an optical microscopy micrograph (scale of black bar is 50 μm) showing an interface between the Intermediate Hydrogel System and a solution of silicon microparticles according to an embodiment.

For the dynamically responsive viscoelastic implant to function as a vas-occlusive male contraceptive, it must also be able to occlude sperm, i.e., prevent sperm from entering the ejaculate. For the implant to occlude sperm, the implant's pore features must be at a smaller scale than the dimensions of sperm cells. Human sperm are ~50 μm long and the smallest part of the head is 3-4 μm wide. The mesh size of the Intermediate System determined by rheology was two orders of magnitude less than the smallest feature of the human sperm cell. As shown in FIG. 5A (with the scale bar at lower left corner being 100 μm), scanning electron microscopy (SEM) of the lyophilized Intermediate System hydrogels indicated a porous structure typical of hydrogels. Lamellae like features are prominent in SEM micrographs of the lyophilized hydrogel, which indicated that network formation occurred rapidly after injection. As shown in FIG. 5B (with the scale bar at lower left corner being 50 μm), optical microscopy of the hydrogel incubated with 1 μm diameter silicon particles, showed a clear interface between the hydrogel and silicon microparticle solution, with no visible penetration of the microparticles into the hydrogel after extended time of agitation with the hydrogel. Experiments measuring the diffusion of water-soluble dyes into the hydrogels formed within the 0.8 mm inner diameter tubing were able to be described by applying Fick's laws (ESI). Finally, a test was conducted where hydrogels were formed onto the membranes of transwell 96-well plates and human sperm was placed either above or below the hydrogel and incubated for 24 hours (using no gel coated membranes as controls). No sperm we able to cross any transwell membranes that we coated with the hydrogel, while sperm plated in no-gel-coated-membranes were able to cross the membrane (ESI). The SEM, 1 μm particle, dye diffusion experiments, and gel-coated transwell experiments demonstrated that the Intermediate System is a semipermeable network capable of blocking objects smaller than sperm, but allowing diffusion of water and proteins.

Figure 5C:
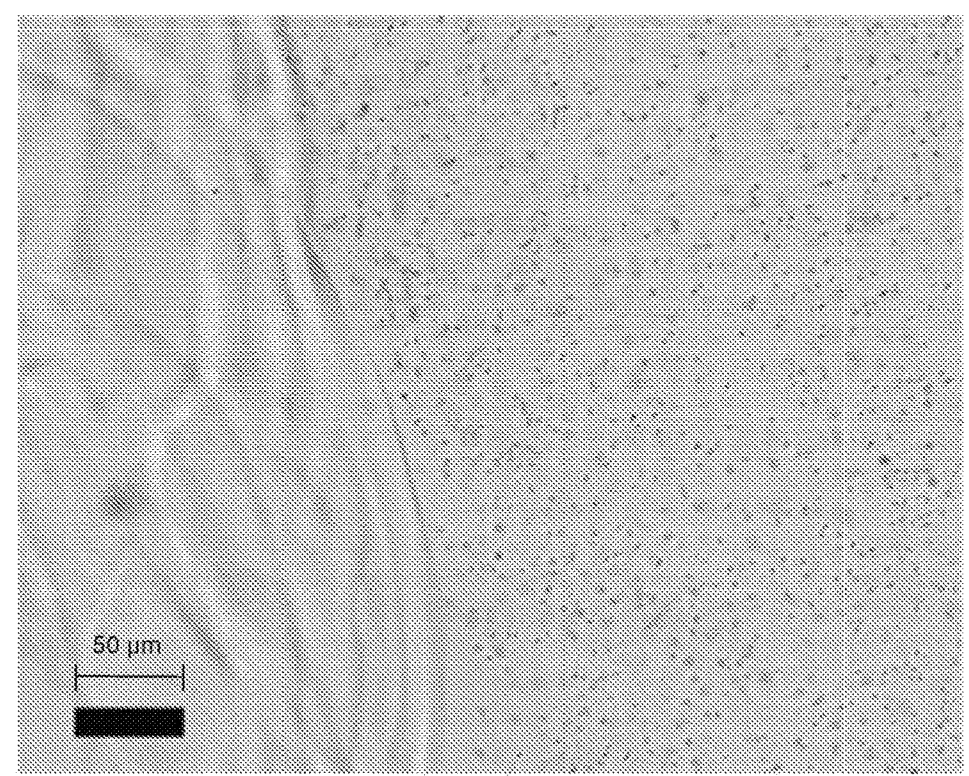
FIG. 5C is a photo of an optical microscopy micrograph (scale of black bar is 50 μm) of sperm interacting with the Intermediate Hydrogel System according to an embodiment.
Figure 5D:
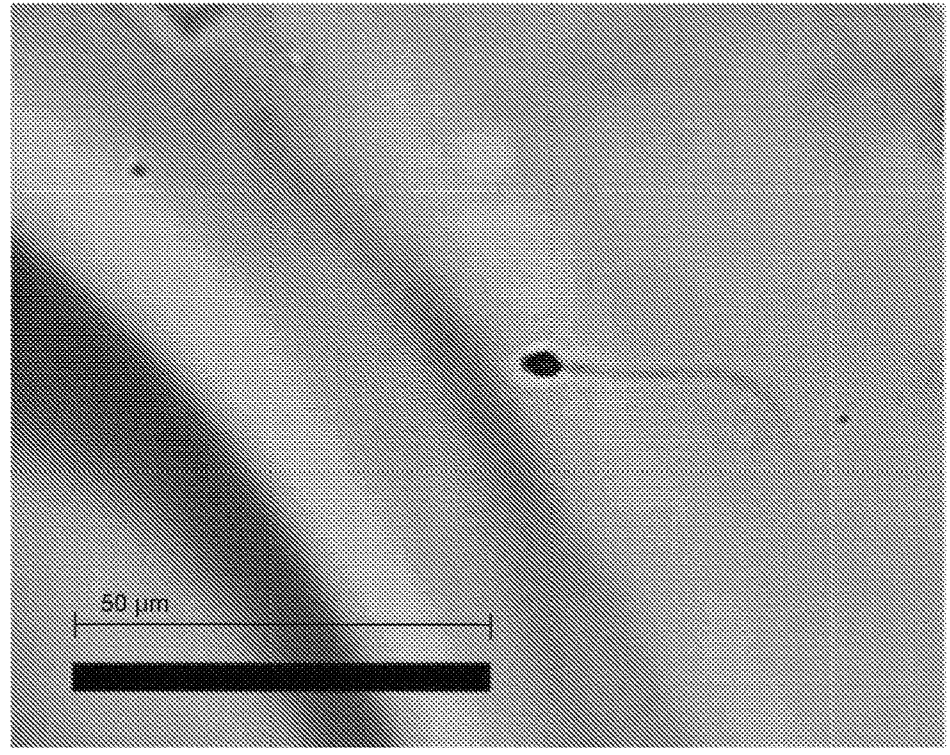
FIG. 5D is a photo of an optical microscopy micrograph (scale of black bar is 50 μm) of sperm interacting with the Intermediate Hydrogel System according to an embodiment.

Imaging was performed on how sperm interacted with the implant. As generally shown in FIG. 5C (with the scale bar at lower left corner being 50 μm), an optical microscope was used to monitor human sperm at the implant interface. At 10× magnification, there is a clear demarcation or interface of what is the implant and what is the sperm solution. When we increased magnification to 40×, as shown in FIG. 5D (with the scale bar at lower left corner being 50 μm), there were instances of sperm swimming directly against the implant-solution interface, thus verifying that our feature sizes are smaller than those of human sperm and indicating that our implant would occlude sperm in vivo.

As described above, the injection properties of two-component hydrogel systems described herein (such as the Intermediate System) are suitable for injection into the vas. By selecting the desired gelation time, injection forces can be reduced while precisely delivering clinically relevant quantities of viscoelastic hydrogels into the vas. Although the Intermediate System has been identified as a candidate for use as a vas-occlusive material, other systems and formulations described herein may also be suitable for use as a vas-occlusive material or for use within other body lumens, cavities, tissues or organs.

Figure 5E:
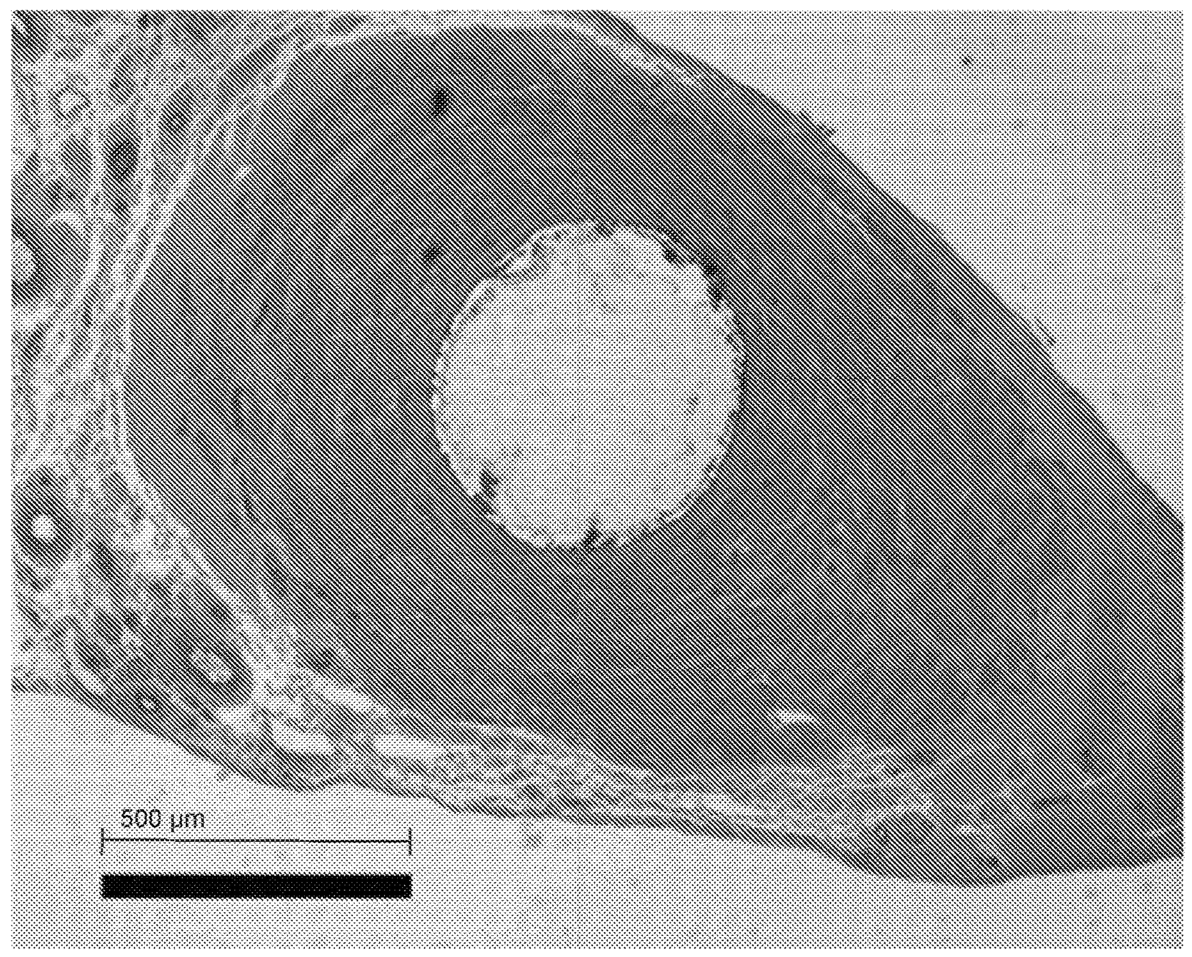
FIG. 5E is a histology of the Intermediate Hydrogel System (scale of black bar is 500 μm) extruded into a canine cadaveric vas.

Finally, feasibility of clinical translation was demonstrated by injection of the hydrogel into cadaveric canine vas using an NSV-like approach. As shown in FIG. 5E (with the scale bar at lower left corner being 500 μm), histology of the cadaveric vas implanted with hydrogel indicated that the material dilated and filled the lumen without damaging the vessel walls and surrounding tissue. Implants within the canine vas were able to withstand 100× in vivo ejaculation pressure without migrating.

Having described suitable components that can be used as a part of a two component hydrogel system, different combinations or formulations of the two components can be utilized to achieve the properties of the three systems described above, such as the properties of the Intermediate System. In some embodiments, a composition can include any of the formulations provided in Table 1. The formulations provided in Table 1 are merely examples. Based on the information provided therein, one of ordinary skill in the art would be able to interpret the data provided and modify the components of the composition accordingly to achieve a particular objective.

TABLE 1

Formulations

| Buffer | M | pH | MW | Chem | Wt % | Meth | Rate | Gel Time | System Type |
|---|---|---|---|---|---|---|---|---|---|
| AA | 0.1 | 4.50 | 20 | SH-MAL | 20 | VID | 566 | ~120 | Slow |
| AA | 0.1 | 5.00 | 20 | SH-MAL | 20 | VID | 283 | ~120 | Slow |
| AA | 0.2 | 4.50 | 20 | SH-MAL | 20 | VID | 5661 | ~120 | Slow |
| AA | 0.2 | 4.50 | 20 | SH-MAL | 20 | VID | 566 | ~120 | Slow |
| AA | 0.2 | 4.50 | 20 | SH-MAL | 20 | VID | 283 | ~120 | Slow |
| AA | 0.2 | 5.00 | 20 | SH-MAL | 20 | VID | 5661 | ~120 | Slow |
| AA | 0.2 | 5.00 | 20 | SH-MAL | 20 | VID | 566 | ~120 | Slow |
| AA | 0.2 | 5.00 | 20 | SH-MAL | 20 | VID | 283 | ~120 | Slow |
| AA | 0.2 | 5.50 | 20 | SH-MAL | 20 | VID | 566 | ~120 | Slow |
| AA | 0.2 | 5.50 | 20 | SH-MAL | 20 | VID | 283 | ~120 | Slow |
| CA | 0.1 | 4.50 | 20 | SH-MAL | 20 | VID | 5661 | ~120 | Slow |
| CA | 0.1 | 4.50 | 20 | SH-MAL | 20 | VID | 566 | ~120 | Slow |
| CA | 0.1 | 4.50 | 20 | SH-MAL | 20 | VID | 283 | ~120 | Slow |
| CA | 0.1 | 5.00 | 20 | SH-MAL | 20 | VID | 5661 | ~120 | Slow |
| CA | 0.1 | 5.00 | 20 | SH-MAL | 20 | VID | 566 | ~120 | Slow |
| CA | 0.1 | 5.00 | 20 | SH-MAL | 20 | VID | 283 | ~120 | Slow |
| CA | 0.2 | 4.00 | 20 | SH-MAL | 20 | VID | 283 | ~120 | Slow |
| CA | 0.2 | 5.25 | 20 | SH-MAL | 20 | VID | 600 | ~30 | Intermediate |
| CA | 0.2 | 5.25 | 20 | SH-MAL | 20 | VID | 566 | ~30 | Intermediate |
| CA | 0.2 | 5.25 | 20 | SH-MAL | 20 | VID | 500 | ~30 | Intermediate |
| CA | 0.2 | 5.25 | 20 | SH-MAL | 20 | VID | 450 | ~30 | Intermediate |
| CA | 0.2 | 5.25 | 20 | SH-MAL | 20 | VID | 400 | ~30 | Intermediate |
| CA | 0.2 | 5.25 | 20 | SH-EMAL (ESTER) | 20 | VID | 400 | ~60 | Intermediate |
| CA | 0.2 | 5.25 | 20 | SH-MAL | 20 | VID | 350 | ~30 | Intermediate |
| CA | 0.2 | 5.25 | 20 | SH-MAL | 20 | VID | 300 | ~30 | Intermediate |
| CA | 0.2 | 5.25 | 20 | SH-MAL | 20 | VID | 283 | ~30 | Intermediate |
| CA | 0.2 | 5.25 | 20 | SH-MAL | 15 | VID | 400 | ~30 | Intermediate |
| CA | 0.2 | 5.25 | 20 | SH-MAL | 10 | VID | 400 | ~30 | Intermediate |
| CA | 0.2 | 5.25 | 20 | SH-MAL | 5 | VID | 400 | ~60 | Intermediate |
| CA | 0.2 | 5.25 | 20 | SH-MAL | 2.5 | VID | 400 | ~120 | Slow |
| CA | 0.2 | 5.25 | 20 | SH-MAL | 1 | VID | 400 | ~120 | Slow |
| CA | 0.2 | 6.00 | 20 | SH-MAL | 2.5 | VID | 400 | ~60 | Intermediate |

TABLE 1-continued

| Formulations | | | | | | | | | |
|---|---|---|---|---|---|---|---|---|---|
| Buffer | M | pH | MW | Chem | Wt % | Meth | Rate | Gel Time | System Type |
| CA | 0.2 | 6.00 | 20 | SH-MAL | 1 | VID | 400 | ~60 | Intermediate |
| CP | 0.15 | 5.50 | 20 | SH-MAL | 20 | VID | 5661 | Imm. | Fast |
| CP | 0.15 | 5.50 | 20 | SH-MAL | 20 | VID | 566 | Imm. | Fast |
| CP | 0.15 | 5.50 | 20 | SH-MAL | 20 | VID | 283 | Imm. | Fast |
| CP | 0.15 | 5.75 | 20 | SH-MAL | 20 | VID | 5661 | Imm. | Fast |
| CP | 0.15 | 5.75 | 20 | SH-MAL | 20 | VID | 566 | Imm. | Fast |
| CP | 0.15 | 5.75 | 20 | SH-MAL | 20 | VID | 283 | Imm. | Fast |
| CP | 0.15 | 5.85 | 20 | SH-MAL | 20 | VID | 5661 | Imm. | Fast |
| CP | 0.15 | 5.85 | 20 | SH-MAL | 20 | VID | 566 | Imm. | Fast |
| CP | 0.15 | 5.85 | 20 | SH-MAL | 20 | VID | 283 | Imm. | Fast |
| PB | 0.1 | 5.50 | 20 | SH-MAL | 20 | VID | 3198 | ~30 | Intermediate |
| PB | 0.1 | 5.50 | 20 | SH-MAL | 20 | VID | 566 | Imm. | Fast |
| PB | 0.1 | 5.50 | 20 | SH-MAL | 20 | VID | 283 | Imm. | Fast |
| PB | 0.1 | 6.00 | 20 | SH-MAL | 20 | VID | 3198 | Imm. | Fast |
| PB | 0.1 | 6.00 | 20 | HZ-AD | 20 | PIP | N/A | Did Not Gel | n/a |
| PB | 0.1 | 6.50 | 20 | SH-EP | 20 | PIP | N/A | <24 hrs | Slow |
| PB | 0.1 | 6.50 | 20 | SH-MAL | 20 | PIP | N/A | Imm. | Fast |
| PB | 0.1 | 6.50 | 40 | SH-MAL | 20 | PIP | N/A | Imm. | Fast |
| PB | 0.1 | 6.50 | 20 | SH-MAL | 20 | VID | 5697 | Imm. | Fast |
| PB | 0.1 | 6.50 | 20 | SH-MAL | 20 | VID | 5661 | Imm. | Fast |
| PB | 0.1 | 6.50 | 20 | SH-MAL | 20 | VID | 3198 | Imm. | Fast |
| PB | 0.1 | 6.50 | 20 | SH-MAL | 20 | VID | 2878 | Imm. | Fast |
| PB | 0.1 | 6.50 | 20 | SH-MAL | 20 | VID | 2302 | Imm. | Fast |
| PB | 0.1 | 6.50 | 20 | SH-MAL | 20 | VID | 1796 | Imm. | Fast |
| PB | 0.1 | 6.50 | 20 | SH-MAL | 20 | VID | 1663 | Imm. | Fast |
| PB | 0.1 | 6.50 | 20 | SH-MAL | 20 | VID | 1612 | Imm. | Fast |
| PB | 0.1 | 6.50 | 20 | SH-MAL | 20 | VID | 1365 | Imm. | Fast |
| PB | 0.1 | 6.50 | 20 | SH-MAL | 20 | VID | 1010 | Imm. | Fast |
| PB | 0.1 | 6.50 | 20 | SH-MAL | 20 | VID | 566 | Imm. | Fast |
| PB | 0.1 | 6.50 | 20 | SH-MAL | 20 | VID | 283 | Imm. | Fast |
| PB | 0.1 | 6.50 | 20 | SH-MAL | 15 | PIP | N/A | Imm. | Fast |
| PB | 0.1 | 6.50 | 20 | SH-MAL | 10 | PIP | N/A | Imm. | Fast |
| PB | 0.1 | 6.50 | 20 | SH-MAL | 5 | PIP | N/A | Imm. | Fast |
| PB | 0.1 | 6.50 | 20 | SH-MAL | 2.5 | PIP | N/A | Imm. | Fast |
| PB | 0.1 | 6.50(SH) + 7.00(MAL) | 40 | SH-MAL (ONB) | 15 | PIP | N/A | ~30 | Intermediate |
| PB | 0.1 | 7.00 (SG) + 9.00 (NH) | 20 | SG-NH | 20 | PIP | N/A | <24 hrs, degraded in <3 days at 37° C. | Slow |
| PB | 0.1 | 7.00 (IC) + 9.00 (NH) | 20 | IC-NH | 20 | PIP | N/A | Did Not Gel | n/a |
| PB | 0.1 | 7.00 | 20 | SH-MAL | 2.5 | VID | 400 | Imm. | Fast |
| PB | 0.1 | 7.00 | 20 | SH-MAL | 1 | VID | 400 | Imm. | Fast |
| PB | 0.1 | 8.00 | 20 | SH-MAL | 2.5 | VID | 400 | Imm. | Fast |
| PB | 0.1 | 8.00 | 20 | SH-MAL | 1 | VID | 400 | Imm. | Fast |
| PB | 0.1 (+0.1/ 0.2M NaCl) | 6.50 | 20 | SH-MAL | 20 | PIP | N/A | Imm. | Fast |

The buffer (first column) can include any of Acetic Acid-Sodium Acetate (AA), Citric Acid-Sodium Citrate (CA), Citric Acid (0.2)-Phosphate Buffer (0.1) (CP), or Phosphate Buffer (PB). The molarity (M) is provided in the second column. The pH is provided in the third column, but can be adjusted for any embodiment to have a pH range of about 4-9. The molecular weight (in kDa) is provided in the fourth column, but can also be adjusted such that the polymer has a molecular weight within a desired range. The chemistry of the components is provided in the fifth column, and can include any of the listed combinations including Thiol (SH), Maleimide (MAL), photo-reversible formulation (ONB), Hydrazide (HZ), Isocyanate (IC), Amine (NH), Succinimidyl Glutaraldehyde (SG), Aldehyde (AD), or Epoxide (EP). The weight percentage (in solution) is provided in the sixth column and likewise can be adjusted according to particular applications, such as providing a composition comprising a desired polymer with a weight percent of up to 20 wt %, such as from about 1-5 wt %, or from about 2-10 wt %, or from about 3-15 wt %, or from about 10-20 wt %. The seventh column provides information regarding the method of delivery performed on the formulation. Methods of delivery were either via an injection device (VID) similar to those described in each of U.S. patent application Ser. Nos. 16/681,572 and 16/681,577, each entitled "Systems and Methods for Delivering of Biomaterials," and each filed Nov. 12, 2019, each which is incorporated herein by reference in its entirety, or via a pipette (PIP). The eighth column provides information on the delivery or injection rate performed on the formulation. The units of injection rate are microliters per minute (μL/min). The gelation time (seconds) is provided in the ninth column. A gelation time of "Imm." indicates that gelation occurred immediately after the two components were combined. The type of system associated with each of the formulations is provided in the last (tenth) column and each of the formulations may have attributes similar to either the Fast System, the Intermediate System, or the Slow System as described herein.

Any of the systems for delivering an implant can include any suitable components, including any of the biomaterial components described herein. For example, in some embodiments, a first component and a second component can each be a water soluble component (e.g., monomer, macromer, polymer, or the like) that is capable of crosslinking (e.g., with the other component) to form a hydrogel (as the delivered biomaterial product). In some embodiments, the first component and the second component are formulated such that the resulting hydrogel has a gelation time of less than 5 minutes. In other embodiments, the first component and the second component are formulated such that the resulting hydrogel has a gelation time of less than two minutes. In other embodiments, the first component and the second component are formulated such that the resulting hydrogel has a gelation time of less than one minute. In yet other embodiments, the first component and the second component are formulated such that the resulting hydrogel has a gelation time of less than about 30 seconds.

In some embodiments, the first component is at least one of a polyvinyl alcohol, alginate or modified alginate, chitosan or modified chitosan, polyethyleneimine, carboxymethyl cellulose, and/or polyethylene glycol terminated with a biorthogonal functional group (e.g., amine, thiol, maleimide, azide, activated ester). The second component is at least one of a water or buffer, water or buffer with divalent cations such as calcium, a solution of reduced hyaluronic acid, a solution of polystyrene sulfonate, a solution of gelatin, and/or polyethylene glycol terminated with a biorthogonal functional group (e.g., amine, thiol, maleimide, azide, activated ester). In some embodiments, polyvinyl alcohol, alginate, chitosan, polyethyleneimine, carboxymethyl cellulose, polyethylene glycol terminated with functional groups, divalent cations, reduced hyaluronic acid, polystyrene sulfonate, or gelatin have a weight percent ranging from about 1 to 30% in solvent, such as about 2 to 10%, about 3 to 12%, about 4 to 15%, about 5 to 20%, about 6 to 25%, or about 7 to 28%, or any range in between any of these endpoints. In some embodiments the polysaccharides may be modified with one or more functional groups, such as the same or different functional groups. For example, the functions groups may include one or more of alcohols, amines, thiols, carboxylic acid, carboxylic acid derivatives, carbonates, carbamates, carbamides, alkanes (n=2 to n=12), alkenes, maleimides, sulfones, vinyl sulfones, and activated carboxylic acids. In some embodiments the polysaccharides and proteins may range in molecular weight from about 10,000 to about 1,000,000 grams/mole, such as about 15,000 to about 900,000 grams/mole, about 20,000 to about 850,000, about 25,000 to about 800,000, about 30,000 to about 700,000, about 50,000 to about 600,000, about 75,000 to about 500,000, about 100,000 to about 400,000, about 200,000 to about 300,000, or about 225,000 to about 275,000. In some embodiments, the polyvinyl alcohol, polystyrene sulfonate, polyethyleneimine, and polyethylene glycol may be linear, Y-shaped, 3-arm, 4-arm, 6-arm, or 8-arm and range in molecular weight from about 1,000 to about 1,000,000 grams/mole such as about 1,500 to about 900,000 grams/mole, about 2,000 to about 850,000, about 2,500 to about 800,000, about 3,000 to about 700,000, about 5,000 to about 600,000, about 7,500 to about 500,000, about 10,000 to about 450,000, about 15,000 to about 50,000, about 100,000 to about 400,000, about 200,000 to about 300,000, or about 225,000 to about 275,000, or any range in between any of these endpoints.

Devices and Delivery Systems

The methods described herein and any of the hydrogel formulations or systems described herein can be performed any suitable delivery device, such as any of the delivery devices shown and described herein or in U.S. patent application Ser. Nos. 16/681,572 and 16/681,577, each entitled "Systems and Methods for Delivering of Biomaterials," each filed on Nov. 12, 2019, and each of which is incorporated herein by reference in its entirety.

Figures 6, 7:
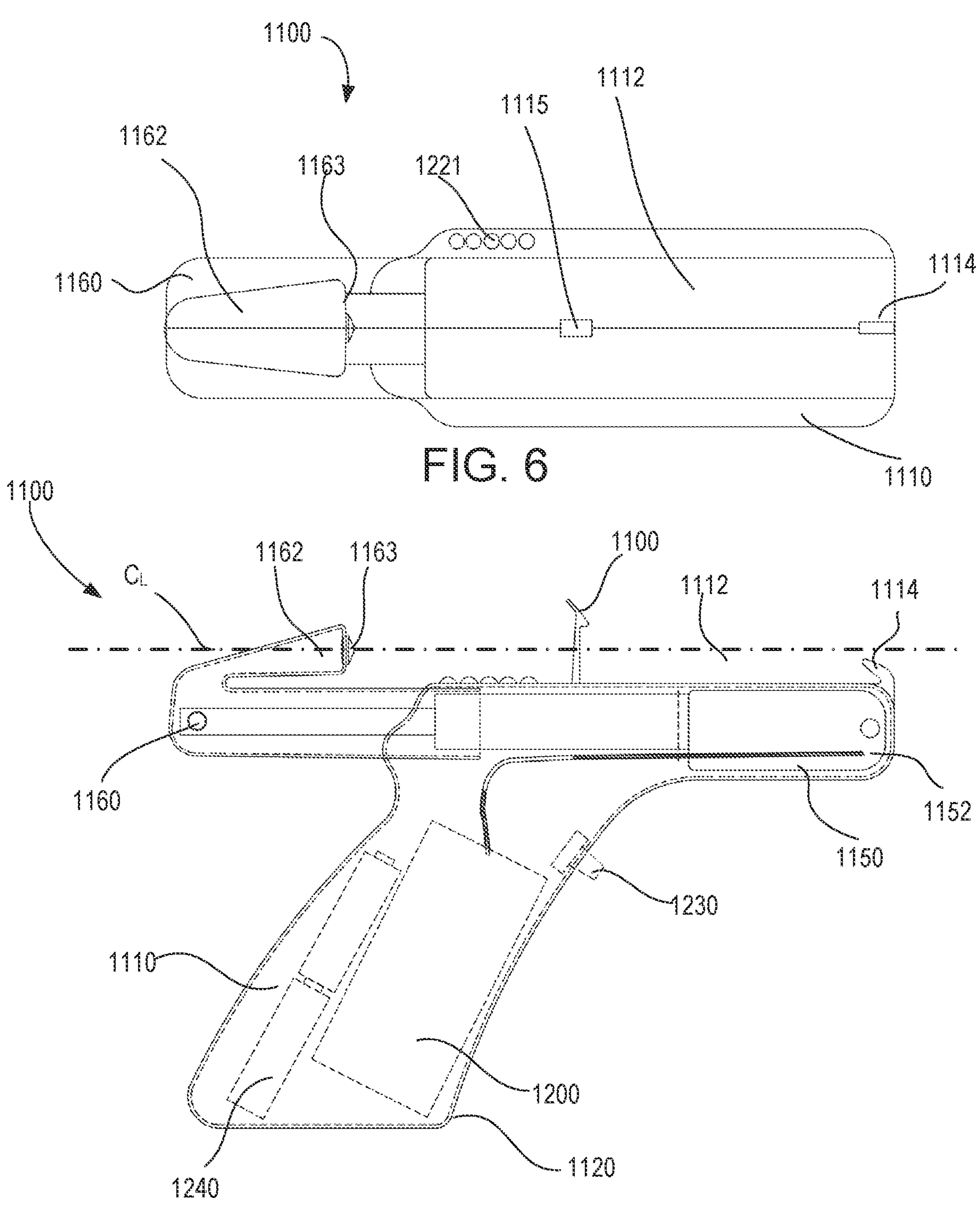
FIG. 6 is a top view of a portion of a delivery system according to an embodiment.
FIG. 7 is a side cross-sectional view of the delivery system of FIG. 6.
Figure 8:
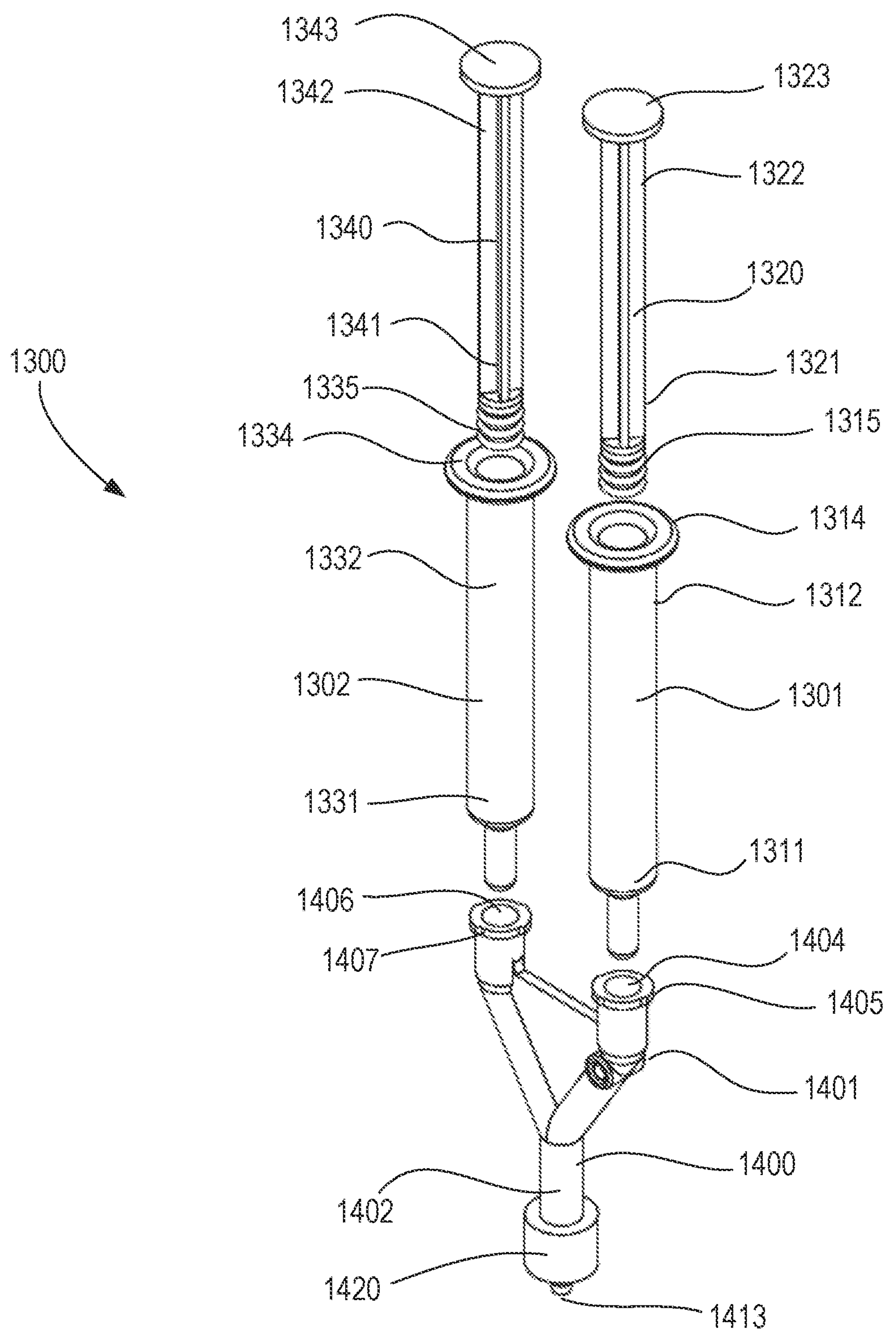
FIG. 8 is an exploded view of a container assembly and a connector according to an embodiment.
Figure 9:
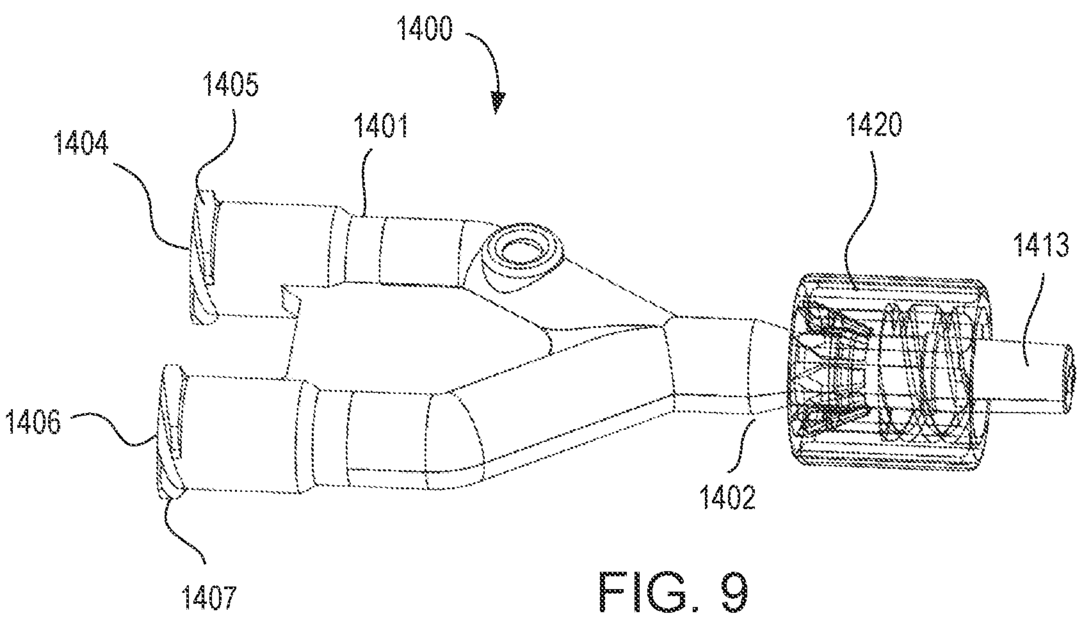
FIG. 9 is a perspective view of the connector of FIG. 8 showing a coupler for removably coupling to a delivery member.
Figure 10:
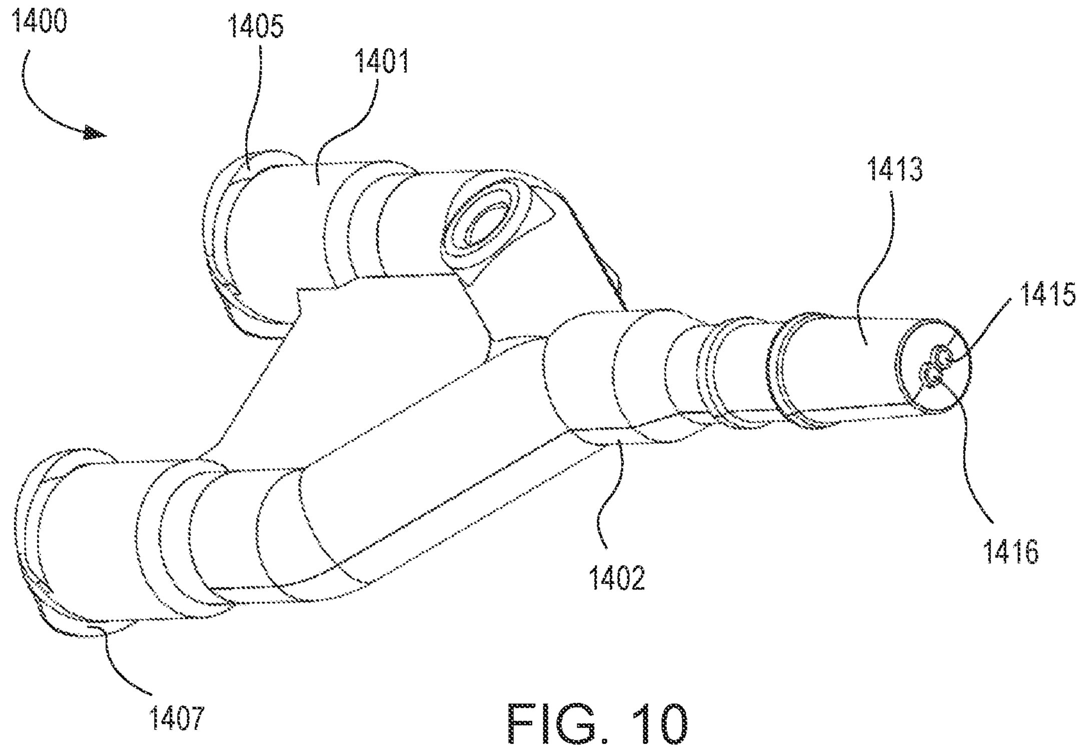
FIG. 10 is a perspective view of the connector of FIG. 9 with the coupler removed.

For example, FIGS. 6-21 are various views of a delivery system 1000 according to an embodiment, that includes, among other things, a cartridge for positioning of the container assembly. The delivery system 1000 includes the delivery device 1100 (e.g., FIGS. 6 and 7), a container assembly 1300 (e.g., FIGS. 8 and 12), a connector 1400 (e.g., FIGS. 8-10), and a delivery member 1500 (e.g., FIGS. 17 and 18). The delivery device 1100 includes a housing 1110, a drive assembly 1150, and an electronic control system 1200.

The housing 1110 includes a container receiving portion 1112 configured to receive at least a portion of the container assembly 1300. The container receiving portion 1112 is an opened portion of the housing 1110 that is bounded by a bottom surface against which the container assembly 1300 and/or the cartridge 1350 can be placed. The container receiving portion 1112 includes a first retainer 1114 and a second retainer 1115. As described in more detail below, the first retainer 1114 engages the first engagement portion 1361 of the cartridge 1350 (see FIG. 11) to retain the cartridge 1350 within the housing 1110 in a fixed position. The second retainer 1115 engages the second engagement portion 1363 of the cartridge 1350 (see FIG. 11) to retain the cartridge 1350 within the housing 1110 in the fixed position. The fixed position can be fixed relative to a home position of the drive assembly 1150 and/or the drive member 1160. Additionally, as shown, the second retainer 1115 includes a lock protrusion that can releasably retain the cartridge 1350 within the housing 1110. The second retainer 1115 is deformable and can be deformed to move the lock protrusion from the second engagement portion 1363 to allow the cartridge 1350 to be removed.

The housing 1110 also contains the drive assembly 1150 and the electronic control system 1200. As shown, the housing 1110 includes a handle 1120 that can be gripped and/or manipulated by a user during operation of the device 1100. The housing 1110 can be made from any suitable material or materials and can provide any suitable structural components to receive and/or retain the portion of the container assembly 1300 and perform any of the functions described herein.

The container assembly 1300 includes a first container 1301 and a second container 1302. The first container 1301 has a first end portion 1311, a second end portion 1312, and includes an elastomeric member (or stopper) 1315 therein. The second end portion 1312 includes a flange 1314 that can be coupled within the cartridge 1350, as described below. The first container 1301 defines a volume that is bounded on one side by the elastomeric member 1315 and that contains a first component. The first container 1301 includes a first plunger 1320 having a first end portion 1321 and a second end portion 1322. The first end portion 1321 is movably disposed within the first container 1301 such that movement of the first plunger 1320 will cause movement of the elastomeric member 1315 to convey the first component from the first container 1301. The second end portion 1322 of the first plunger 1320 terminates in a flange 1323 that is operably coupled to (e.g., is configured to engage) the drive member 1160. The second container 1302 has a first end portion 1331, a second end portion 1332, and includes an elastomeric member (or stopper) 1335 therein. The second end portion 1332 includes a flange 1334 that can be coupled within the cartridge 1350, as described below. The second container 1302 defines a volume that is bounded on one side by the elastomeric member 1335 and that contains a second component. The second container 1302 includes a second plunger 1340 having a first end portion 1341 and a second end portion 1342. The first end portion 1341 is movably disposed within the second container 1302 such that movement of the second plunger 1340 will cause movement of the elastomeric member 1335 to convey the second component from the second container 1302. The second end portion 1342 terminates in a flange 1343 that is operably coupled to (e.g., is configured to engage) the drive member 1160.

Figures 11, 12:
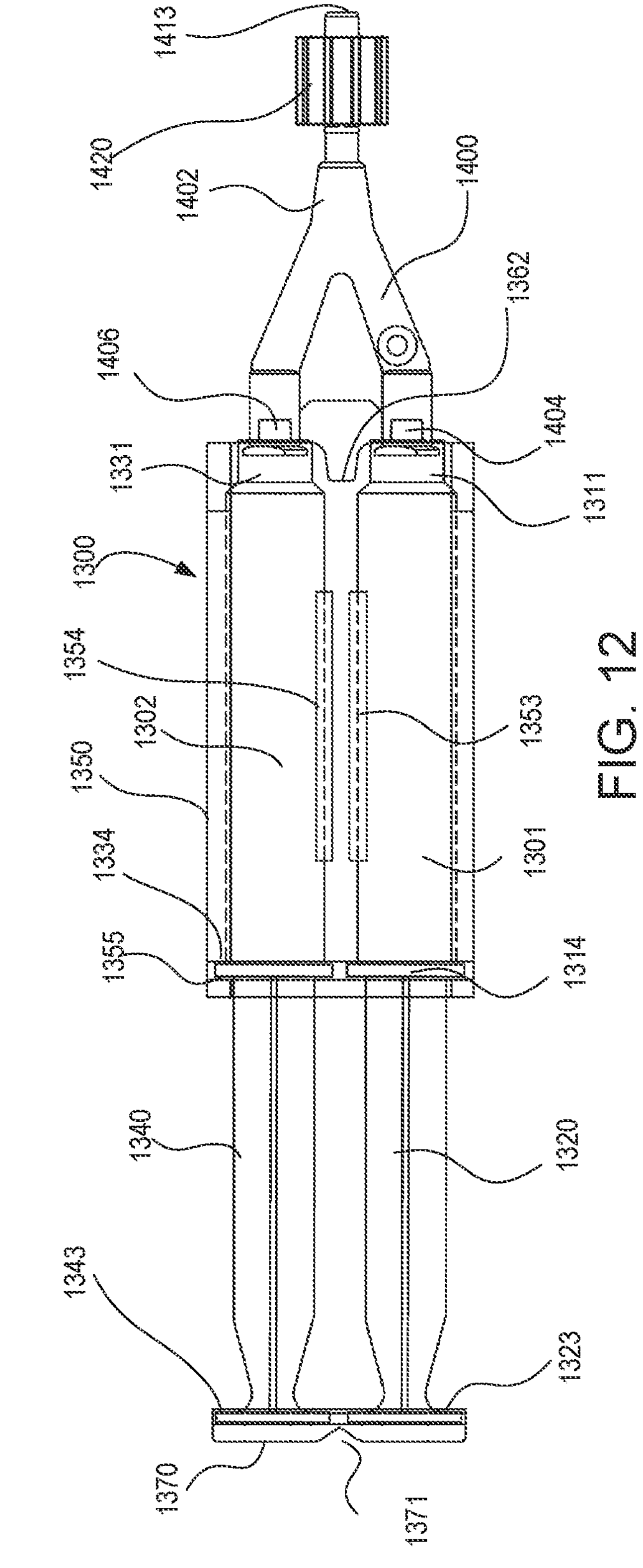
FIG. 11 is a top view of portion of a cartridge for holding the container assembly of the delivery system shown in FIG. 8.
FIG. 12 is a top view of the container assembly and connector of FIG. 8 installed on the cartridge of FIG. 11.
Figure 13:
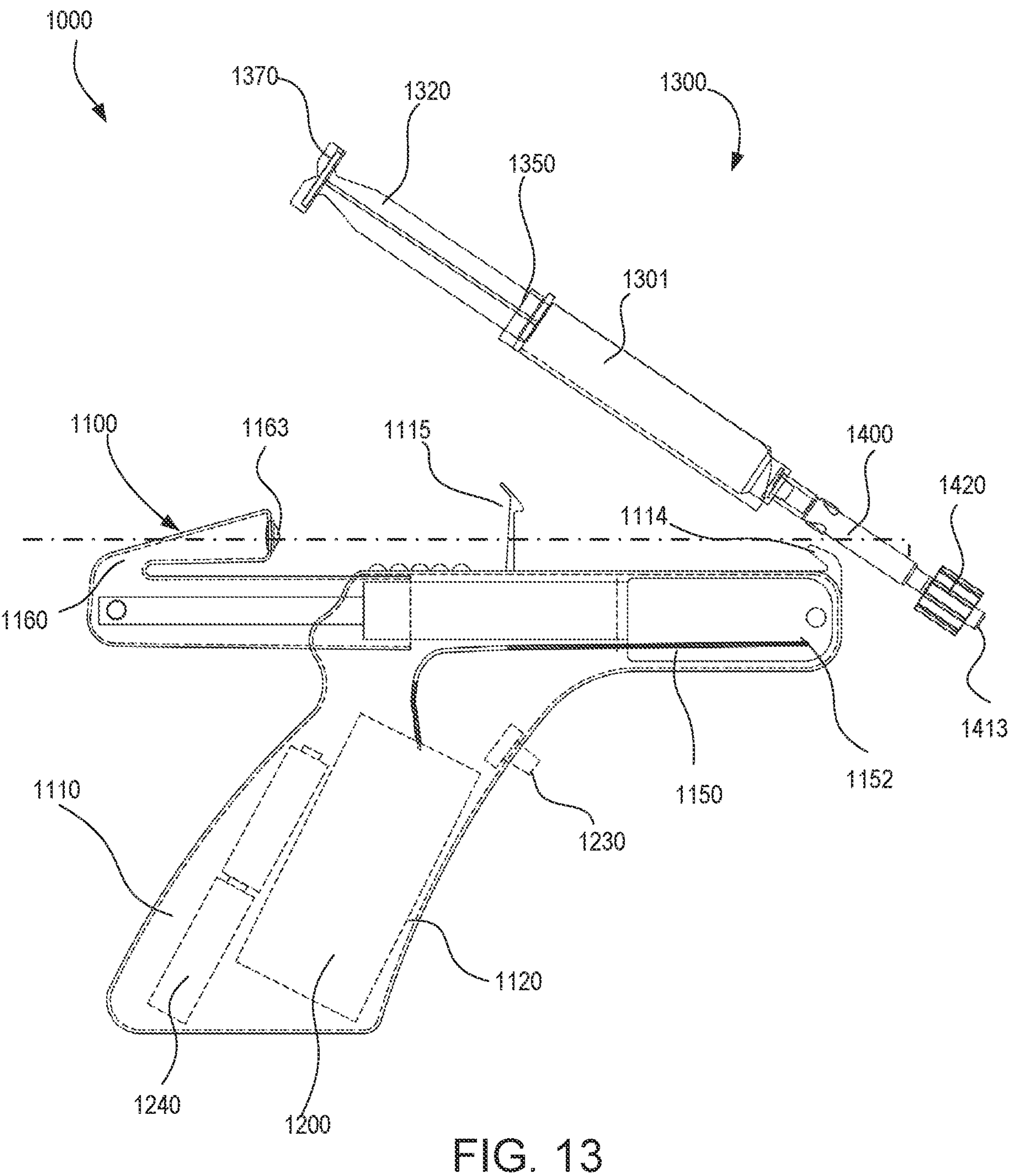
FIGS. 13 and 14 are side cross-sectional views of the cartridge, container assembly, and connector of FIG. 12 being installed onto the delivery system of FIG. 7.
Figures 14, 15:
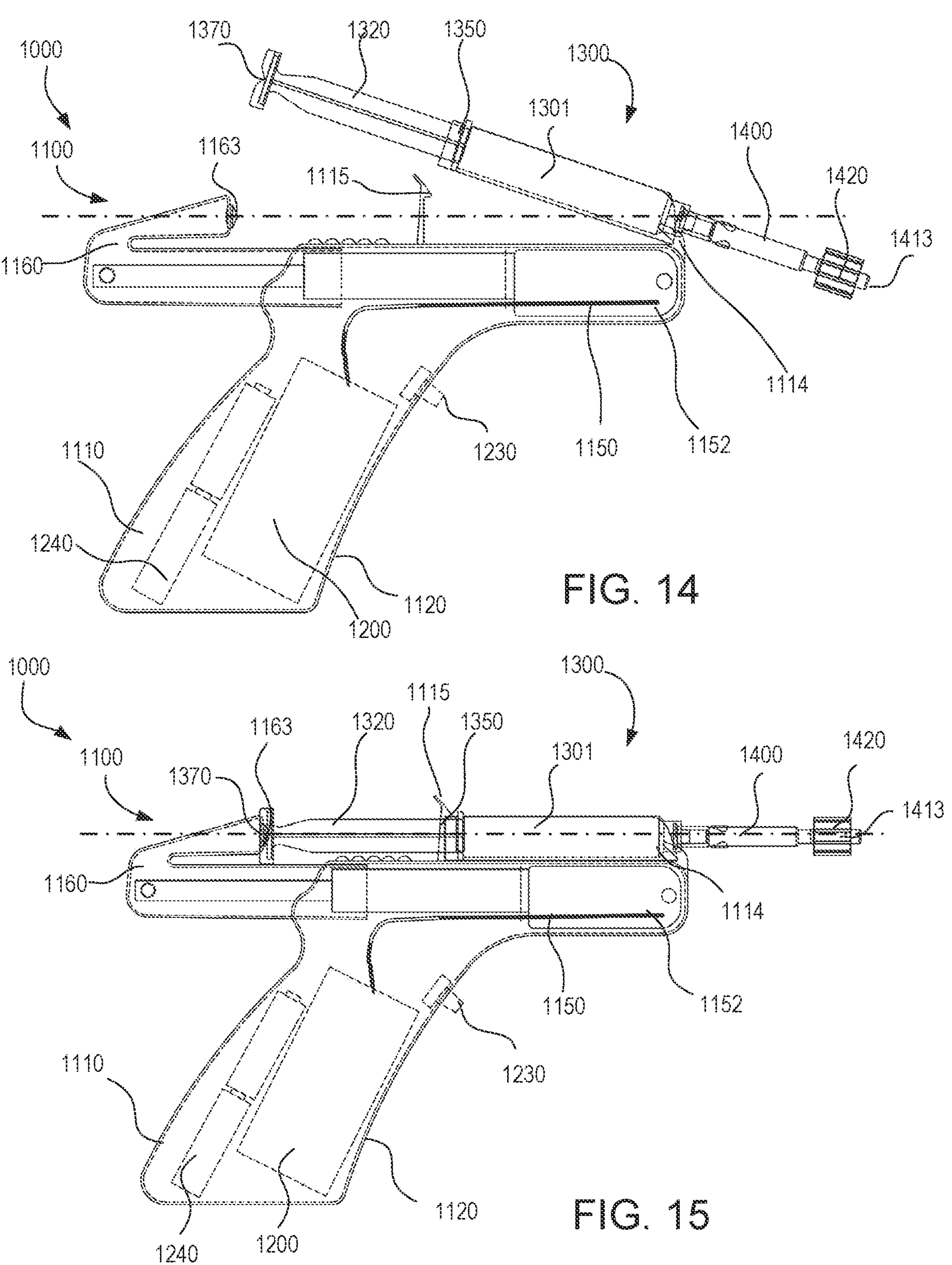
FIG. 15 is a side cross-sectional view of the cartridge, container assembly, and connector installed onto the delivery system of FIG. 7.
Figure 16:
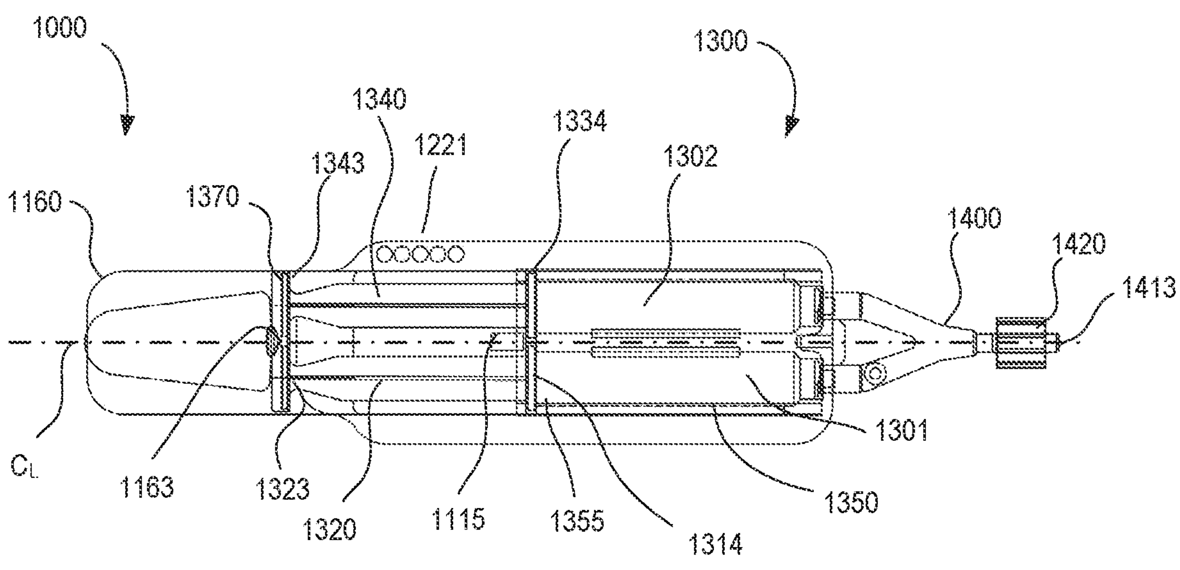
FIG. 16 is a top view of the cartridge, container assembly, and connector installed onto the delivery system of FIG. 7.

Referring to FIGS. 11 and 12, the cartridge 1350 defines a first recess or opening 1351 that receives a portion of the first container 1301 (i.e., the container body) and a second recess or opening 1352 that receives a portion of the second container 1302 (i.e., the container body). The cartridge 1350 includes a first retainer (or clip) 1353, a second retainer (or clip) 1354, a first engagement portion 1361, and a second engagement portion 1363. The first retainer 1353 forms a boundary of the first recess 1351 and engages the container body of the first container 1301 to retain the first container 1301 within the cartridge. The second retainer 1354 forms a boundary of the second recess 1352 and engages the container body of the second container 1302 to retain the second container 1302 within the cartridge. Either or both of the first retainer 1353 and the second retainer 1354 can be deformable to form an interference fit with the respective container body. In this manner, the containers can be securely and removably fastened within the cartridge 1350. The first retainer 1353 and the second retainer 1354 can position the containers in a fixed position in a first direction, i.e., normal to the longitudinal center line CL of the container assembly 1300 and/or the delivery device 1100. The cartridge 1350 define a flange slot 1355 within which the flange 1314 (of the first container 1301) and the flange 1334 (of the second container 1302) are received. In this manner, the position of the containers along the center line CL can be fixed.

The first engagement portion 1361 of the cartridge define a notch 1362 that receives and/or matingly engages the first retainer 1114 of the housing 1110. The second engagement portion 1363 includes a surface against which the lock protrusion of the second retainer 1115 can engage to removably retain the cartridge 1350 (and therefore, the container assembly 1300) within the housing 1110 (see e.g., FIGS. 14 and 15). This arrangement allows the cartridge 1350 to be coupled to the delivery device 1100 in a fixed position relative to a home position associated with the drive assembly 1150. In other embodiments, the housing can define one or more recesses or notches and the cartridge can include one or more protrusions to securely (and removably) couple the cartridge 1350 to the housing 1110.

The plunger link 1370 is configured to be coupled to the flange 1323 of the first plunger 1320 and the flange 1343 of the second plunger 1340. Specifically, the plunger link 1370 defines a retention slot 1371 and includes a surface against which the drive member 1160 can exert a drive force. In some embodiments, the drive force exerted can be in the range of about 0.1 N to about 10 N, such as 0.5 N to about 5 N, about 0.7 N to about 2.5 N, or about 1 N to about 2 N, or any range in between. The retention slot 1371 receives the flange 1323 and the flange 1343. The plunger link 1370 facilitates the use of a single drive assembly 1150 to produce the drive force to repeatably move both the first plunger 1320 and the second plunger 1340. In other embodiments, however, a plunger link is not included. In some embodiments, the first plunger 1320 and the second plunger 1340 can include an engagement portion to couple or attach to the pistons (or stoppers) within each container.

The first component and the second component can be any of the biomaterial components described herein.

The container assembly 1300 is configured to be coupled to the connector 1400, which is, in turn, coupled to a delivery member 1500. By having the containers as separate articles from the connector 1400 and delivery member 1500, the first component and the second component can each be prepared within the container assembly 1300 (e.g. via mixing, dilution, etc.) separately from when connector 1400 is attached. In other embodiments, however, the container assembly 1300 can be provided as a prefilled assembly and include prefilled syringes or prefilled cartridges. In some embodiments, the prefilled assembly can be provided with premixed components, or the prefilled assembly can be provided with separate powder(s) and solvent(s) that can be combined prior to use with the delivery device 1100.

The connector 1400 includes a first (or input) end portion 1401 and a second (or output) end portion 1402. The first end portion includes a first inlet 1404 that is coupled to a tip (or connector) of the first container 1301 (e.g., via the flange 1405, which can be coupled to a luer connector, not shown, of the first container 1301). The first end portion includes a second inlet 1406 that is coupled to a tip (or connector) of the second container 1302 (e.g., via the flange 1407, which can be coupled to a luer connector, not shown, of the second container 1302). The second end portion 1402 is configured to be coupled to the delivery member 1500 (see FIG. 17). The second end portion 1402 includes a fitting 1420, which can rotate relative to the connector 1400 to couple to a mating flange of the hub 1520 of the delivery member 1500. In some embodiments, the fitting 1420 and the connector 1400 can include one or more indicators to provide a visual cue to a user to confirm that a secure connection has been made. In some embodiments, the connector 1400 and the delivery member 1500 can include one or more indicators to provide a visual cue to a user to confirm that a secure connection has been made. In some embodiments, a sensor can be provided in (or associated with) the connector 1400 and/or the delivery member 1500 to detect a secure connection. For example, the sensor can communicate with the electronic control system 1200 to provide an audible or visual cue to the user that a secure connection has been made, or a warning if a secure connection has not been made. In some embodiments, the sensor can communicate with the electronic control system 1200 to prohibit the drive assembly 1150 from operating in the event of an incomplete or improper connection.

The connector 1400 defines a first passageway placing the first inlet 1404 in fluid communication with a first outlet 1415 (see FIG. 10) and a second passageway placing the second inlet 1406 in fluid communication with a second outlet 1416. In this manner, the first component can be conveyed from the first container 1301, into the first end portion of the connector 1400, and out of the first outlet 1415 into a mixing volume 1521 of the delivery member 1500. Similarly, the second component can be conveyed from the second container 1302, into the first end portion of the connector 1400, and out of the second outlet 1416 into the mixing volume 1521 of the delivery member 1500. Thus, the connector 1400 maintains the first component separate from the second component, and the two components are conveyed into and mixed within the hub 1520 of the delivery member 1500. By maintaining separate flow paths within the connector 1400, the reaction (e.g., crosslinking) between the first component and the second component can be performed outside of the connector 1400 (i.e., within the delivery member 1500), thereby limiting the likelihood of clogging with the connector 1400. In this manner, the connector 1400 can be used for multiple injections.

Figure 17:
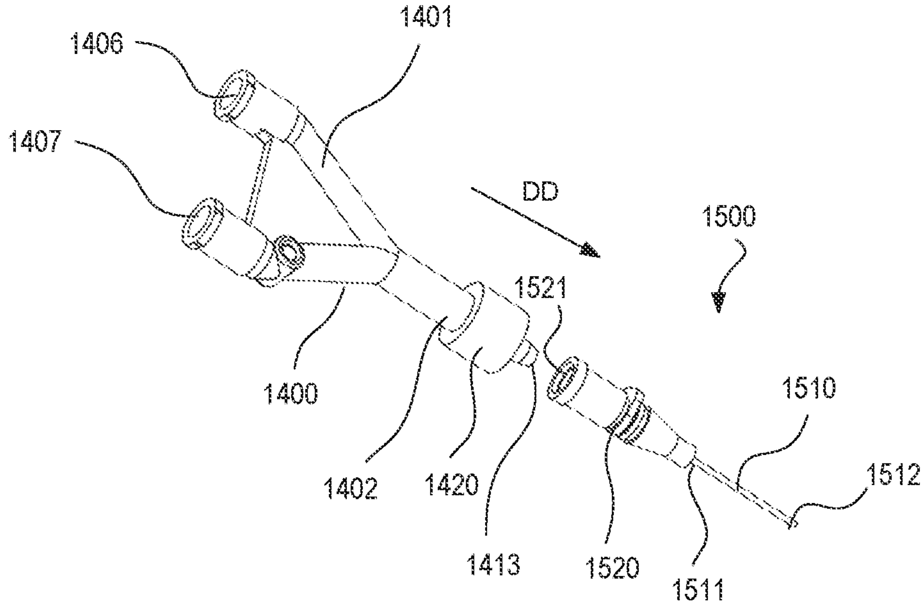
FIG. 17 is a perspective view of a connector and a delivery member according to an embodiment.
Figures 18, 19:
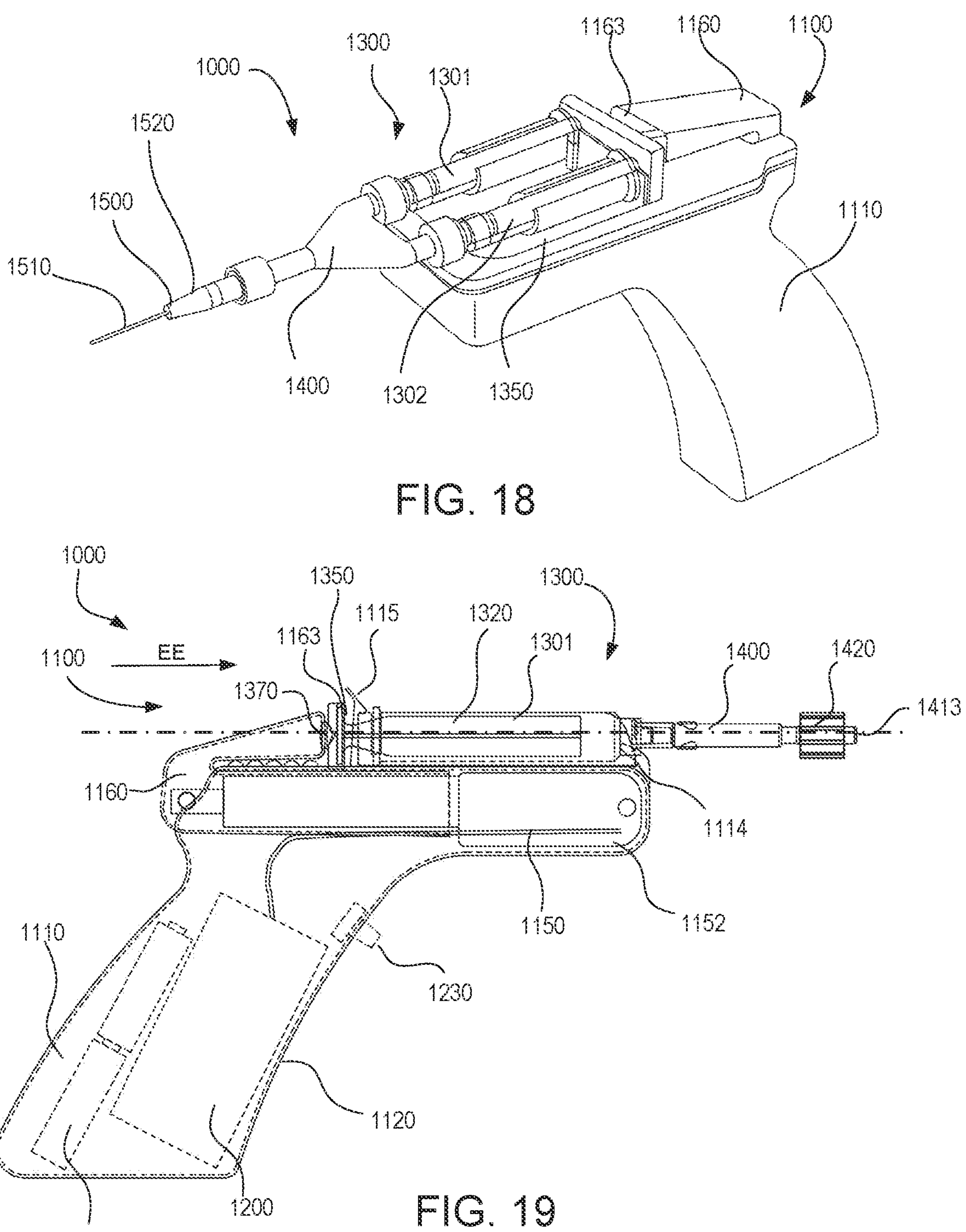
FIG. 18 is a perspective view of a delivery member mounted onto connector of the delivery system of FIG. 17 according to an embodiment.
FIG. 19 is a side cross-sectional view of the delivery system of FIG. 18, after delivery of the components from the container assembly.
Figure 20:
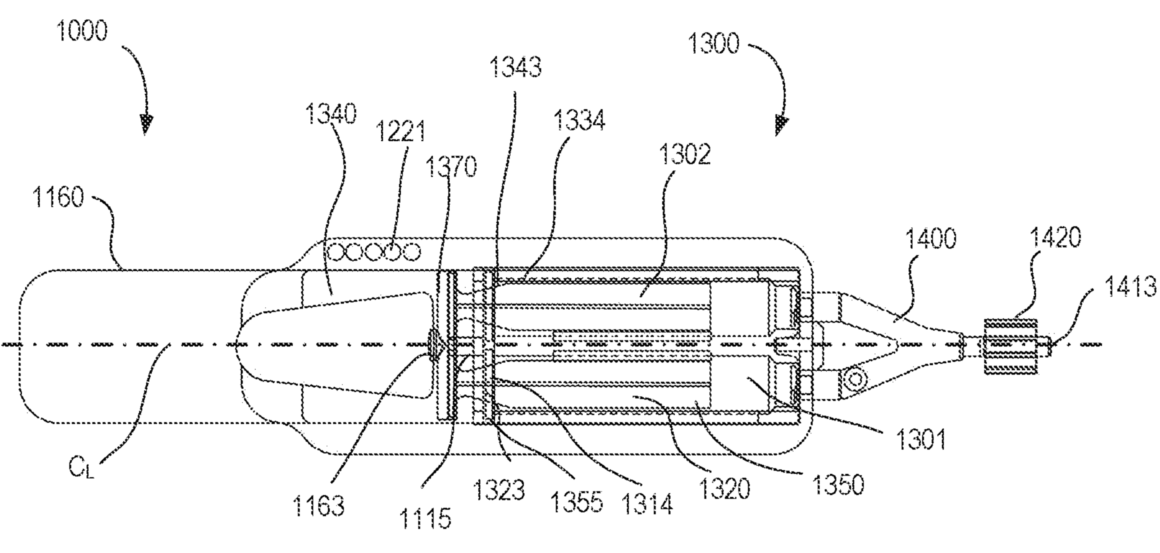
FIG. 20 is a top view of the delivery system of FIG. 18, after delivery of the components from the container assembly.
Figure 21:
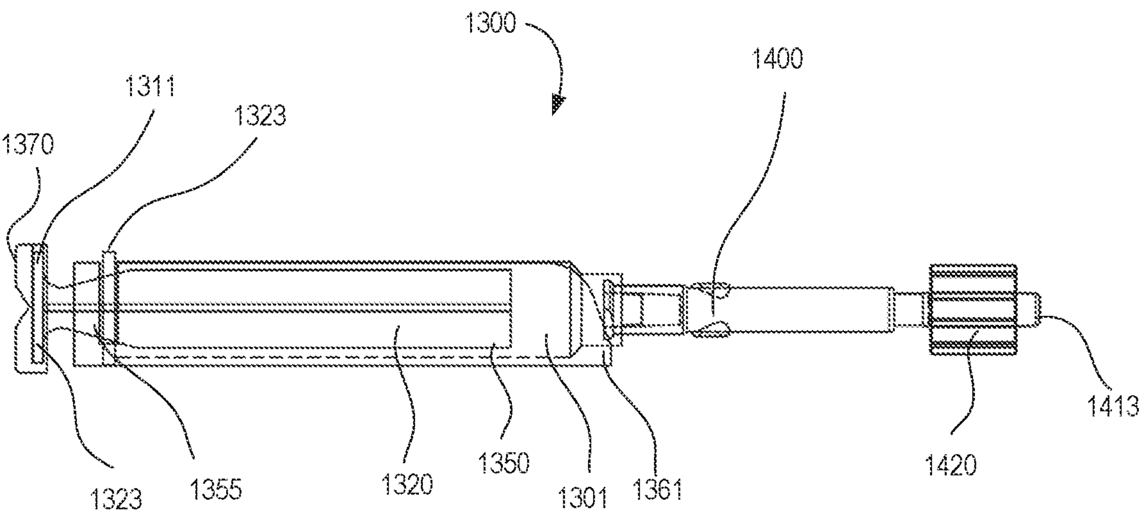
FIG. 21 is a partial side cross-sectional view of the cartridge, container assembly, and connector in the delivery system of FIG. 18 after having been removed from the delivery device.

The delivery member 1500 includes a catheter 1510 coupled to a hub 1520. The hub 1520 includes a flange or other suitable fastening mechanisms by which the hub 1520 can be coupled to the fitting 1420 of the connector 1400. As shown in FIG. 17, the hub 1520 defines a mixing volume 1521 within which the first component and the second component can be conveyed and mixed together. The catheter 1510 includes a first end 1511 coupled to the hub 1520 and a second end 1512 that can be inserted into a body lumen, cavity, tissue, organ, or other target location.

The drive assembly 1150 can be any suitable assembly or mechanism that produces a drive force to convey the first biomaterial component and the second biomaterial component from the container assembly 1300. As shown, the drive assembly 1150 includes an electromechanical driver 1152 and a drive member 1160. The electromechanical driver 1152 can be any of the electromechanical drivers described herein, and in this embodiment, is a linear actuator powered by a stepper motor that produces the drive force. The drive member 1160 has an end portion 1162 that is operably coupled to the container assembly 1300 by a contact surface 1163. Specifically, the contact surface 1163 can engage the corresponding surface of the plunger link 1370 such that, upon actuation, the drive assembly 1150 can move the first plunger 1320 and the second plunger 1340 along the longitudinal center line CL. In some embodiments, the drive assembly 1150 can include one or more springs and dampers in addition to, or in lieu of, the electromechanical driver 1152 to provide controlled actuation of the first plunger 1320 and the second plunger 1340 along the longitudinal center line CL.

The electronic control system 1200 controls the electromechanical driver 1152 and other aspects of the drive assembly 1150 to control the delivery characteristics of the first component, the second component, and/or the delivered product, as described herein. Moreover, the electronic control system 1200 can cause the drive assembly 1150 to produce separate movement associated with a priming operation and an injection operation. In some embodiments, any of the delivery devices described herein can be configured to prime the biomaterial product and/or perform the injection. "Priming" is defined as any steps that prepare the material prior to injection, for example, mixing or merging solutions within the device, removing dead volume (e.g., from the connector), and/or setting/adjusting the injection volume. "Injection" is defined as delivering the biomaterial product into the body. In one aspect, the priming and injection steps are pre-defined and not adjustable by the user (e.g. physician). In one aspect, both the priming and injection steps are adjustable by the user. In one aspect, the priming and injection steps can be a combination of adjustable and not adjustable.

Although not shown, the electronic control system 1200 can include one or more sensors, one or more processors, one or more memory components, and various modules, such as a drive module and a user interface module. As shown, the electronic control system 1200 includes an actuator (or trigger) 1230 and a set of output devices 1221. Although not shown, the electronic control system 1200 can include various user input switches, such as a prime switch and/or an injection switch, to control the priming operation and/or the injection operation. The electronic control system 1200 is powered by a power supply 1240. The power supply 1240 can be any suitable power supply, such as a battery (including a rechargeable battery), an AC to DC converter (e.g., to facilitate an AC powered device). The actuator 1230 can provide input to the electronic control system 1200 via a user interface module (not shown). In some embodiments, the user interface module can be a hardware and/or software module. The user interface module can be configured to receive input from and/or produce output to the user. For example, the user can depress the actuator button 1230, which is operatively coupled to the electronic control system 1200. The user interface module can receive the input and produce one or more signals based on the user input. For example, in some embodiments, the user interface module can produce a signal to the drive assembly 1150 to "prime" the system by moving the drive member 1160 a predetermined distance. In other embodiments, the user interface module can produce a signal to the drive assembly 1150 to stop movement of the drive member 1160 (e.g., in an error state or "stop" state). The user interface module can also produce a signal to cause the electronic control system 1200 to produce one or more outputs. For example, in some embodiments, the electronic control system 1200 (and any of the electronic control systems described herein) includes an output device, such a light output device (e.g., LED's), an audible output device (e.g., speaker), or a tactile output device (e.g., vibration device). In such embodiments, the user interface module can produce a signal to cause the output device to produce an output (e.g., a visual, audible, or tactile output) to indicate a change in state (e.g., priming completed, mixing completed, injection complete) or error condition associated with the delivery device 1100. In some embodiments, the user interface module includes a graphical user interface to display information relating to the system 1000 and to receive inputs from a user.

In use, the electronic control system 1200 can control the drive assembly 1150 based on the user input received to produce any of a prime signal, an injection signal, and a drive signal, as described above. For example, the electronic control system 1200 (and/or the drive module) can produce, control, and/or adjust a drive signal to control the electromechanical driver to maintain an exit force of the biomaterial product (e.g., hydrogel) being conveyed out of the delivery member 1500 below an exit force threshold. In some embodiments, the electronic control system 1200 (and/or the drive module) can produce, control, and/or adjust a drive signal to control the electromechanical driver to maintain a velocity of the first component, the second component, and/or the delivered biomaterial product within a desired velocity range or delivery time range.

FIG. 22 is a flow chart illustrating a method 100 of delivering a biomaterial product, according to an embodiment. The method can be performed using the delivery system 1000 or any other suitable system. The method includes coupling a container assembly to a delivery member at 110. The container assembly defines a first chamber and a second chamber. The first chamber is fluidically isolated from the second chamber and contains a first component. The second chamber contains a second component, and the first component is formulated to be crosslinked with the second component to form a hydrogel. The first component and the second component are formulated such that the hydrogel has a gelation time. The method includes conveying a portion of the first component and a portion of the second component into a mixing volume of the delivery member and through the delivery member withing a delivery time that is less than the gelation time, at 120. The first component crosslinks with the second component to at least partially form the hydrogel within the delivery member such that the conveying causes the hydrogel to be conveyed out of an exit opening of the delivery member.

In some embodiments, the conveying of the hydrogel out of the delivery member includes conveying the hydrogel to a body lumen, cavity, tissue, or organ. In some embodiments, the body lumen, cavity, tissue or organ is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space. In some embodiments, the hydrogel conveyed to the body lumen, cavity, tissue or organ at least partially occludes the body lumen, cavity, tissue, organ, or a portion thereof.

In some embodiments, the first component and the second component are formulated such that a viscoelastic substance is conveyed out of the exit opening of the delivery member. In some embodiments, the first component and the second component are formulated to have an initial storage modulus (initial G') and an initial loss modulus (initial G") when the first component and the second component are initially combined, a ratio of the initial G" to the initial G' being between about 5 and about 100. The first component and the second component are formulated to have a delivered storage modulus (delivered G') and a delivered loss modulus (delivered G") when the first component and the second component are conveyed out of the delivery member, a ratio of the delivered G" to the delivered G' being between about ⅓ and about 3. In some embodiments, the ratio of the initial G" to the initial G' is between about 30 and about 50, and the ratio of the delivered G" to the delivered G' is between about ⅓ and about 1.

In some embodiments, the first component and the second component are formulated to have a gelation storage modulus (gelation G') and a gelation loss modulus (gelation G") after the gelation time. A ratio of the gelation G" to the gelation G' being less than about 0.2. In some embodiments, the ratio of the gelation G" to the gelation G' is about 0.1.

In some embodiments, the conveying of the first component and the second component is performed by an electromechanical driver of a drive assembly of a delivery device, the delivery device including an electronic control system. The conveying of the first component and the second component includes producing, via the electronic control system, a drive signal that controls the electromechanical driver to maintain a velocity of the hydrogel within the delivery member within a predetermined velocity range.

In some embodiments, the first component comprises a multi-arm polyethylene glycol terminated with thiol, and the second component comprises a multi-arm polyethylene glycol terminated with a maleimide. In some embodiments, the multi-arm polyethylene glycol terminated with thiol and/or the multi-arm polyethylene glycol terminated with a maleimide have a weight percent ranging from about 1 to 30% in solvent. In some embodiments, the multi-arm polyethylene glycol may be linear, Y-shaped, 3-arm, 4-arm, 6-arm, or 8-arm. In some embodiments, the first component and the second component are formulated to have a pH less than about 5.25.

Figure 23:
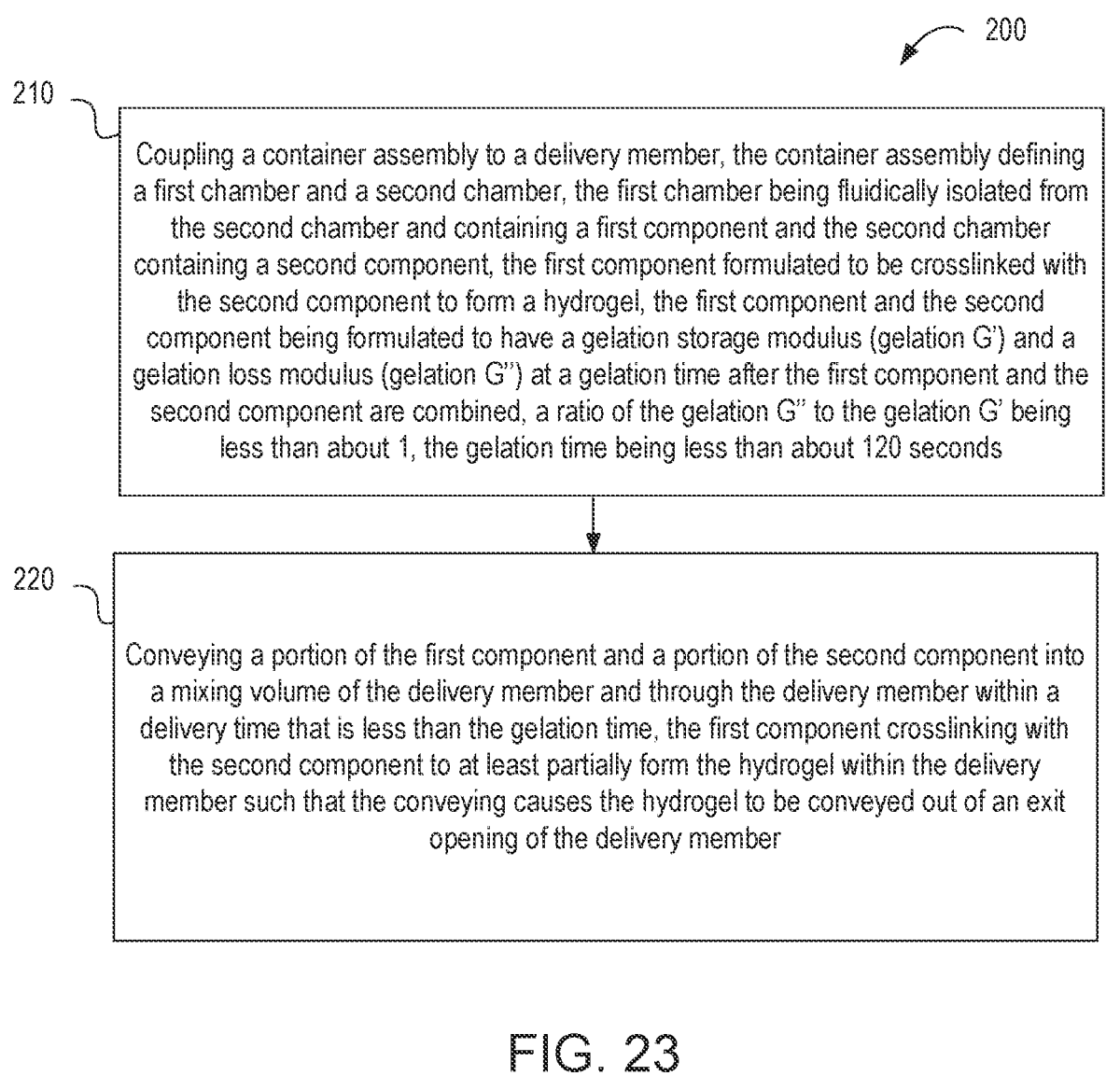

FIG. 23 a flow chart illustrating a method 200 of delivering a biomaterial product, according to an embodiment. The method can be performed using the delivery system 1000 or any other suitable system. The method includes coupling a container assembly to a delivery member at 210. The container assembly defines a first chamber and a second chamber. The first chamber is fluidically isolated from the second chamber and contains a first component and the second chamber contains a second component. The first component is formulated to be crosslinked with the second component to form a hydrogel. The first component and the second component is formulated to have a gelation storage modulus (gelation G') and a gelation loss modulus (gelation G") at a gelation time after the first component and the second component are combined. A ratio of the gelation G" to the gelation G' is less than about 1, and the gelation time is less than about 120 seconds. The method includes conveying a portion of the first component and a portion of the second component into a mixing volume of the delivery member and through the delivery member within a delivery time that is less than the gelation time, at 220. The first component crosslinks with the second component to at least partially form the hydrogel within the delivery member such that the conveying causes the hydrogel to be conveyed out of an exit opening of the delivery member.

In some embodiments, the conveying of the hydrogel out of the delivery member includes conveying the hydrogel to a body lumen, cavity, tissue, or organ. In some embodiments, the body lumen, cavity, tissue or organ is one of an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space. In some embodiments, the hydrogel conveyed to the body lumen, cavity, tissue or organ at least partially occludes the body lumen, cavity, tissue or organ.

In some embodiments, the first component and the second component are formulated such that a viscoelastic substance is conveyed out of the exit opening of the delivery member. In some embodiments, the first component and the second component are formulated to have an initial storage modulus (initial G') and an initial loss modulus (initial G") when the first component and the second component are initially combined, a ratio of the initial G" to the initial G' being between about 5 and about 100. In some embodiments, the ratio of the initial G" to the initial G' is between about 30 and about 50. In some embodiments, the first component and the second component are formulated to have a gelation storage modulus (gelation G') and a gelation loss modulus (gelation G") after the gelation time, a ratio of the gelation G" to the gelation G' being less than about 0.2. In some embodiments, the ratio of the gelation G" to the gelation G' is about 0.1.

In some embodiments, the conveying of the first component and the second component is performed by an electromechanical driver of a drive assembly of a delivery device. In some embodiments, the delivery device includes an electronic control system. The conveying of the first component and the second component includes producing, via the electronic control system, a drive signal that controls the electromechanical driver to maintain a velocity of the hydrogel within the delivery member within a predetermined velocity range.

In some embodiments, the first component comprises a multi-arm polyethylene glycol terminated with thiol, and the second component comprises a multi-arm polyethylene glycol terminated with a maleimide. In some embodiments, the multi-arm polyethylene glycol terminated with thiol and/or the multi-arm polyethylene glycol terminated with a maleimide have a weight percent ranging from about 1 to 30% in solvent. In some embodiments, the multi-arm polyethylene glycol may be linear, Y-shaped, 3-arm, 4-arm, 6-arm, or 8-arm. In some embodiments, the first component and the second component are formulated to have a pH less than about 5.25.

Any of the delivery members described herein can be any suitable delivery member, such as a needle, a catheter, or any other device through which the first component, the second component, and/or the biomaterial product (e.g., delivered product) can be delivered to the target location. In some embodiments, a connector and a delivery member can be monolithically constructed or otherwise pre-assembled prior to use. In other embodiments, a system can include a connector that is separate from the delivery member and is later coupled to the delivery member as a part of the delivery procedure.

In some embodiments, any of the systems and methods described herein can deliver the biomaterial product at any suitable velocity range. In some embodiments, the predetermined velocity range is bounded by an upper velocity threshold and a lower velocity threshold. By maintaining the velocity below the upper velocity threshold, the biomaterial can be delivered in a manner that limits the likelihood of tissue damage (e.g., due to excessive velocity causing potential tissue damage). Moreover, maintaining the velocity below the upper velocity threshold can ensure that the delivered biomaterial product is formed to the desired extent within the system before exiting the delivery member. For example, in some embodiments, the components that produce the biomaterial product are formulated such that they have an initial storage modulus (initial G') and an initial loss modulus (initial G") when the first component and the second component are initially combined. Initially, the G" is greater than the G' and the components are in a liquid state when initially combined. For example, certain formulations can produce a ratio of the initial G" to the initial G' of between about 5 and about 100. The first component and the second component are further formulated such that after being combined, crosslinking of the components will cause the G' will increase and will eventually become greater than the G". In this manner, the components form a viscoelastic (nonliquid) substance. Similarly stated, the crosslinking of the components produces the biomaterial product (e.g., the hydrogel). The time period during which the ratio of G" to G' is reduced to a target ratio (e.g., between ⅓ and 3) is dependent on the formulation of the components. Accordingly, by controlling the delivery velocity the system can ensure that the delivered hydrogel is sufficiently formed within the delivery member. For example, in some embodiment, the components are formulated such that the ratio of G" to G' reaches a value of less than one in a formation time (e.g., between 6 seconds and 30 second). In such embodiments, the desired residence time (i.e., the delivery time) of the first component and the second component within the delivery member is at least as great as the formation time. Additionally, as described herein, the components can also have a gelation time that is greater than the delivery time. Thus, the predetermined velocity range can be any suitable range to accommodate the desired delivery characteristics. For example, in some embodiments, the velocity range can be between about 0.1 mm/sec to 10 mm/sec. In other embodiments, the velocity range can be between about 0.1 mm/sec to 5 mm/sec. In other embodiments, the velocity range can be between about 0.01 mm/sec and 1 mm/sec.

Moreover, by maintaining the velocity within the predetermined range and for the predetermined delivery time, the system can deliver a volume of the biomaterial product that is within a desired volume range. In this manner, the amount of biomaterial can be accurately controlled. In some embodiments, the volume range is between about 5 microliters and about 1000 microliters. In other embodiments, the volume range is between about 50 microliters and 500 microliters. In yet other embodiments, the volume range is between about 50 microliters and 250 microliters. In still other embodiments, the volume range is between about 75 microliters and 150 microliters.

In some embodiments, any of the hydrogels described herein can be conveyed out of the exit opening of the delivery member into a body lumen, cavity, tissue, or organ to at least partially occlude the body lumen, cavity, tissue or organ. The body lumen, cavity, tissue or organ can be any suitable body lumen, cavity, tissue or organ, such as for example, an artery, vein, capillary, vessel, tissue, intra-organ space, lymphatic vessel, vas deferens, epididymis, fallopian tube, duct, bile duct, hepatic duct, cystic duct, pancreatic duct, parotid duct, organ, uterus, prostate, organ of a gastrointestinal tract or circulatory system or respiratory system or nervous system, subcutaneous space, intramuscular space, or interstitial space.

The present disclosure also relates to an apparatus for performing the operations herein. This apparatus may be specially constructed for the intended purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, Universal Serial Bus (USB) flash drives, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general-purpose systems may be used with programs in accordance with the teachings herein, or it may prove convenient to construct a more specialized apparatus to perform the method. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), Universal Serial Bus (USB) flash drives, and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

In some embodiments, the apparatus is used to inject a biomaterial that is formed from one or more precursors. For example, two macromer solutions are injected that cross-link with each other to form a hydrogel material. The apparatus injects solutions into the body, such that the solutions form a hydrogel in situ. In some embodiments, the apparatus is used to inject the formed biomaterial into the body, e.g. cross-linked hydrogel. The hydrogel may continue to gel and/or cross-link in situ once injected or can be completely gelled or cross-linked by the time it exits the apparatus. In this regard, the apparatus facilitates the merging or mixing of the two or more different solutions into a single stream.

In some embodiments, the type and size of syringe selected for the apparatus impacts the injection parameters and biomaterial extruded. In some embodiments, a material of the syringe is glass, plastic, or a combination of both. The syringe can be lubricated or non-lubricated. In some embodiments, the syringe contains from about 0.1 mL to 100 mL in volume. For example, the syringes can be 0.5 cc, 1 cc, 2 cc, 5 cc, 10 cc, 20 cc, 50 cc, and/or 100 cc syringes. An inner diameter of the syringes can range from about 0.2 mm to 50 mm. For example, 1 cc plastic BD syringes may be 4.64 mm in diameter. The cylindrical cross-sectional area may range from 0.168 to 967.7 $mm^2$ (0.000026 to 1.5 $in^2$). In some embodiments, the plunger can be selected for a particular application based on different attributes including, for example, manufacturer, volume, length, inner diameter and lubrication chosen. The plunger may be lubricated or non-lubricated, and be made of synthetic rubber, natural rubber, thermoplastic, and/or an elastomer. In some embodiments, the syringes may be locked into a holder, also referred to as a chassis. In one aspect, the syringes can be loaded or included within a cassette-style syringe holder, which may be disposed after use.

In one embodiment, the apparatus contains a Y-connector (also known as blending connector) which contains channels for solutions to flow through. For example, manufacturers of Y-connectors include, but are not limited to, Nordson Medical (Micromedics), Medmix, and Sulzer. In one embodiment, the channels of the Y-connector do not facilitate mixing of the precursor solutions. Therefore, the solutions may merge or mix in the needle and/or catheter hub. In some embodiments, the dual lumen catheter or needle is attached to the Y-connector to prevent any mixing or merging of the solutions within the apparatus. In some embodiments, the Y-connector is attached to the syringe(s) on one end.

In some embodiments, the apparatus includes tubing to extend the distance from the syringes within the apparatus to the Y-connector and/or angiocath/needle. For example, manufacturers of such tubing include, but are not limited to, Zeus, Medline and Cook Medical. In some embodiments, mixing of the two solutions occurs in the extension tubing. In some embodiments, mixing does not occur in the tubing. In some embodiments, a mixing chamber is attached to the Y-connector, such that the solutions merge or mix within the mixing chamber after exiting the Y-connector. In some embodiments, the mixing chamber includes a number of mixing elements, which determine the degree of mixing, such as 1 to 20 mixing elements. In some embodiments, a needle and/or catheter is attached to the mixing chamber.

In some embodiments, the apparatus includes a catheter or needle or combination of both, by which the biomaterial can be extruded from. The catheter or needle or combination is chosen based on a desired application, location of implantation, chemical properties of the biomaterial (e.g. viscosity), and desired injection volume, speed, and force. The needle and/or catheter is configured to deliver the biomaterial subdermally, percutaneously, or intraluminally. In some embodiments, the apparatus includes a needle-sheathed catheter or a catheter-sheathed needle. The maximum needle size/gauge is determined by the lumen of the vessel, duct, or organ which will receive the external stimulus and as a result the exact size of catheter, needle, or instrument is not critical so long as it is shaped and sized appropriately for a particular application. The gauged needle and/or catheter can have a diameter ranging for example between about 100 μm and 5 mm, including 0.1 mm, 0.2 mm, 0.3 mm, 0.4 mm, 0.5 mm, 0.6 mm, 0.7 mm, 0.8 mm, 0.9 mm, 1.0 mm, 1 mm, 2 mm, 3 mm, 4 mm, or 5 mm. In some embodiments, the needle diameter is preferably between 0.3 mm to 1 mm. In some embodiments, the size of the needle and/or catheter is from about 6 gauge to 34 gauge, such as from about 10 gauge to 34 gauge, or about from 15 gauge to 32 gauge, or about from 20 gauge to 26 gauge, or about from 22 gauge to 26 gauge, and so on. In some embodiments, the size of the needle is between about 21 gauge and 31 gauge. In some embodiments, the needle can be extra thin walled (XXTW), extra thin walled (XTW), thin walled (TW), or regular walled (RW). For example, standard needle sizes are readily available such as at http://www.sigmaaldrich.com/chemistry/stockroom-reagents/learning-center/technical-library/needle-gauge-chart.html, listing needle sizes from 6 gauge to 34 gauge. In some embodiments, the needle is used to introduce a secondary catheter within the lumen of the vessel. In one aspect, the needle or catheter can have a length between about 0.1 inch and 15 inches, preferably from about 0.5 inch to 10 inches, such as from about 0.8 to 5 inches, or from about 0.4 to 1 or 2 or 3 inches. In some embodiments, the needle is echogenic, or visible on ultrasound.

In some embodiments, operating parameters of the apparatus is optimized to perform consistent and/or controlled injection. These parameters include, but are not limited to, the injection rate, volume injected, peak extrusion force, peak pressure in syringes, distance plungers move, plunger speed, and plunger acceleration. As operating parameters are altered for particular applications, the resulting injection and delivery of the biomaterial is altered. For example, the chemical, mechanical, and/or biological properties of the biomaterial (e.g. hydrogel or implant), including, but not limited to, the length, width, and volume of the implant, the gelation time of the implant, the shape of the implant, and how the implant interacts with the surrounding tissue can be altered based on the operating parameters. The length of the implant may directly impact the efficacy of the device, such as for occlusion of the vas deferens for male contraception.

In some embodiments, the apparatus is configured to add a solvent (e.g. dissolving solution) to a powder (e.g. polymer) within the device prior to performing a priming or injection step. For example, a container such as syringe, vial, or ampule containing the polymer powder is loaded into a slot within the apparatus, where upon pressing a button and/or trigger, the apparatus fills the container with a solution to dissolve the powder. In some embodiments, a carrier solution is added to solids or dehydrated materials prior to delivery. In some embodiments, the dissolution or hydration of the dehydrated materials with the carrier solution is initiated via the user pressing a button, switch, or trigger, after which the user will be able to perform priming and injection steps. In some embodiments, after mixing of solids and the carrier solvent, the apparatus is configured to de-gas or remove air generated from the mixing of the liquids and the solids, prior to performing priming and/or injection steps.

In some embodiments, the biomaterial includes one or more of natural or synthetic monomers, polymers or copolymers, biocompatible monomers, polymers or copolymers, such as polystyrene, neoprene, polyetherether ketone (PEEK), carbon reinforced PEEK, polyphenylene, polyetherketoneketone (PEKK), polyaryletherketone (PAEK), polyphenylsulphone, polysulphone, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, fluoropolymers such as polytetrafluoroethylene (PTFE or TEFLON®), TEFLON® TFE (tetrafluoroethylene), polyethylene terephthalate (PET or PETE), TEFLON® FEP (fluorinated ethylene propylene), TEFLON® PFA (perfluoroalkoxy alkane), and/or polymethylpentene (PMP) styrene maleic anhydride, styrene maleic acid (SMA), polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaxonone, polyanhydride, trimethylene carbonate, poly(β-hydroxybutyrate), poly(g-ethyl glutamate), poly(DTH-iminocarbonate), poly (bisphenol A iminocarbonate), poly(orthoester) (POE), polycyanoacrylate (PCA), polyphosphazene, polyethyleneoxide (PEO), polyethylene glycol (PEG) or any of its derivatives, polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), polyoxazoline (POx), poly(vinyl alcohol) poly(acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, keratin, pectin, elastin, ethylene vinyl acetate, ethylene vinyl alcohol (EVOH), polyethylene oxide, PLLA or PLA (poly(L-lactide) or poly (L-lactic acid)), poly(D,L-lactic acid), poly(D,L-lactide), polydimethylsiloxane or dimethicone (PDMS), poly(isopropyl acrylate) (PIPA), polyethylene vinyl acetate (PEVA), PEG styrene, polytetrafluoroethylene RFE such as TEFLON® RFE or KRYTOX® RFE, fluorinated polyethylene (FLPE or NALGENE®), methyl palmitate, temperature responsive polymers such as poly(N-isopropylacrylamide) (NIPA), polycarbonate, polyethersulfone, polycaprolactone, polymethyl methacrylate, polyisobutylene, nitrocellulose, medical grade silicone, cellulose acetate, cellulose acetate butyrate, polyacrylonitrile, poly(lactide-co-caprolactone (PLCL), and/or chitosan.

In some embodiments, the dissolving solution for the polymer component(s) may be aqueous buffers (pH range 1-14): phosphate, citrate, acetate, histidine, lactate, tromethamine, gluconate, aspartate, glutamate, tartrate, succinate, malic acid, fumaric acid, alpha-ketoglutaric, and/or carbonate. Non-aqueous solvents include: dimethyl isosorbide, glycofurol 75, PEG 200, diglyme, tetrhydrofurfuryl alcohol, ethanol, acetone, solketal, glycerol formal, dimethyl sulfoxide, propylene glycol, ethyl lactate, N-methyl-2-pyrrolidone, dimethylacetamide, methanol, isopropanol, 1,4-butanediol, ethyl acetate, toluene, acetonitrile. In some embodiments, when the polymer component is dissolved, the viscosity of the solution(s) that make up the biomaterial may range from about 0.1 to about 250,000 cP, such as about 0.5 to about 200,000 cP, about 1 to about 150,000 cP, about 5 to about 100,000 cP, about 10 to about 75,000 cP, about 20 to about 50,000 cP, about 50 to about 25,000 cP, about 100 to about 10,000 cP, about 500 to about 7,500 cP, or about 1,000 to about 5,000 cP, or any viscosity in between. The density of the solution may range from about 0.1 to about 20,000 $kg/m^3$, such as about 1 to about 15,000 $kg/m^3$, about 5 to about 12,500 $kg/m^3$, about 10 to about 10,000 $kg/m^3$, about 100 to about 5,000 $kg/m^3$, about 500 to about 2,5000 $kg/m^3$, or about 1,000 to about 1,500 $kg/m^3$, or any density in between. The temperature during extrusion may range from about 2 to about 45° C., such as about 5 to about 40° C., about 10 to about 38° C., about 15 to about 37° C., about 20 to about 36° C., about 25 to about 35° C., about 30 to about 34° C., or about 31 to about 33° C., or any temperature in between. The pH of the solution(s) may range from 1-14. The ionic strength of the solution(s) may range from about 1 nM to about 70 M, such as about 5 nM to about 60 M, about 10 nM to about 50 M, about 20 nM to about 25 M, about 50 nM to about 15 M, about 75 nM to about 10 M, 100 nM to about 5 M, or about 500 nM to about 2.5 M, or any molarity in between.

In some embodiments, if two components are injected to form the biomaterial, then the ratio of the components may be varied such as 1:1, 2:1, 1:2, 3:1, 1:3, 4:1, 1:4, and up to 10:1 or 1:10. The gelation time of the biomaterial may range from about 0.001 seconds to about 60 minutes, such as about 1 second to about 45 minutes, about 5 seconds to about 30 minutes, about 10 seconds to about 15 minutes, about 20 seconds to about 10 minutes, about 30 seconds to about 8 minutes, about 45 seconds to about 5 minutes, about 1 minute to about 3 minutes, or about 1.5 minutes to about 2.5 minutes, or any range in between. The length of the formed biomaterial may range from about 0.1 to about 60 cm, such as about 0.2 to about 50 cm, about 0.3 to about 40 cm, about 0.4 to about 30 cm, about 0.5 to about 20 cm, about 0.6 to about 15 cm, about 0.8 to about 10 cm, about 0.9 to about 5 cm, about 1.2 to about 4 cm, about 1.4 to about 3 cm, about 1.6 to about 2.5 cm, or about 1.8 to about 2.2 cm, or any range in between. The volume of the formed biomaterial may range from about 0.001 to about 100 mL, such as about 0.005 to about 90 mL, about 0.01 to about 80 mL, about 0.05 to about 70 mL, about 0.1 to about 60 mL, about 0.2 mL to about 50 mL, about 0.25 to about 40 mL, about 0.4 to about 30 mL, about 0.5 to about 20 mL, about 0.7 to about 10 mL, about 0.9 to about 5 mL, about 1.1 to about 4 mL, about 1.4 to about 3 mL, or about 2 mL to about 2.5 mL, or any range in between.

In some embodiments, the biomaterial swells within the implantation space to lock or secure its placement. For example, a biomaterial in the form of a hydrogel may swell from about 1.5× to about 10× its initial volume, such as about 2× to about 8×, about 2.5× to about 7×, about 3× to about 6×, or about 4× to about 5×, or any range in between. In some embodiments, the extruded biomaterial conforms to the space it is injected into. In some embodiments, the swelling of the biomaterial does not change volume within the implantation space, or shrinks to conform to a volume of the implantation space. In some embodiments, the apparatus injects a pre-formed biomaterial (does not cross-link, form, or gel in situ). Once injected, the biomaterial may or may not react with the implantation space. If a reaction does occur, it may be covalent or non-covalent. In some embodiments, the biomaterial adhesively interacts within the implantation space.

A number of embodiments have been described. Nevertheless, it will be understood that various modifications may be made without departing from the spirit and scope of the invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above. Any of the components and sub-components described herein can be included in any of the embodiments unless mutually exclusive.

What is claimed is:

1. A composition, comprising:

a first component and a second component, the first component formulated to be crosslinked with the second component to form a hydrogel;

the first component and the second component being formulated to have an initial storage modulus (initial G') and an initial loss modulus (initial G") when the first component and the second component are initially combined, a ratio of the initial G" to the initial G' being between about 5 and about 100; and the first component and the second component being formulated to have a gelation storage modulus (gelation G') and a gelation loss modulus (gelation G") at a gelation time after the first component and the second component are combined, a ratio of the gelation G" to the gelation G' being less than about 0.1, the gelation time being less than about 120 seconds.

2. The composition of claim 1, wherein the gelation time is less than about 60 seconds.

3. The composition of claim 1, wherein:

the first component comprises a multi-arm polyethylene glycol terminated with one or more thiol; and the second component comprises a multi-arm polyethylene glycol terminated with one or more maleimide.

4. The composition of claim 1, wherein at least one of the first component or the second component is dissolved in a solvent and has a weight percentage within the solvent of between about 1% and 30%.

5. The composition of claim 1, wherein at least one of the first component or the second component is dissolved in a solvent having a pH of between about 4.5 and 8.

6. The composition of claim 1, wherein the gelation time is less than about 30 seconds.

7. The composition of claim 1, wherein the gelation time is between about 1 second and 60 seconds.

8. The composition of claim 4, wherein the weight percentage is between about 1% and 20%.

9. The composition of claim 8, wherein the weight percentage is about 20%.

10. The composition of claim 5, wherein the pH is between about 4.5 and 5.25.

11. The composition of claim 1, wherein the first component and the second component are capable of crosslinking and forming an implantable network by way of a bio-orthogonal reaction.

12. The composition of claim 1, wherein the first component and the second component are formulated such that the hydrogel is substantially formed before being conveyed out of a delivery member.

13. The composition of claim 1, wherein the first component and the second component are formulated such that a viscoelastic substance is conveyed out of a delivery member.

14. A composition, comprising:

a first component and a second component, the first component formulated to be crosslinked with the second component to form a hydrogel;

the first component and the second component being formulated to have an initial storage modulus (initial G') and an initial loss modulus (initial G") when the first component and the second component are initially combined, a ratio of the initial G" to the initial G' being between about 5 and about 100; and the first component and the second component being formulated to have a gelation storage modulus (gelation G') and a gelation loss modulus (gelation G") at a gelation time after the first component and the second component are combined, a ratio of the gelation G" to the gelation G' being less than about 0.2, the gelation time being between about 1 second and 60 seconds.

15. The composition of claim 14, wherein the ratio of the gelation G" to the gelation G' is about 0.1.

16. The composition of claim 14, wherein the gelation time is less than about 30 seconds.

17. The composition of claim 14, wherein at least one of the first component or the second component is dissolved in a solvent having a pH of between about 4.5 and 8.

18. The composition of claim 14, wherein at least one of the first component or the second component is dissolved in a solvent and has a weight percentage within the solvent of between about 1% and 20%.

19. The composition of claim 14, wherein:

the first component comprises a multi-arm polyethylene glycol terminated with one or more amine; and the second component comprises a multi-arm polyethylene glycol terminated with one or more activated ester.

20. The composition of claim 1, wherein:

the first component comprises a multi-arm polyethylene glycol terminated with one or more amine; and the second component comprises a multi-arm polyethylene glycol terminated with one or more activated ester.

* * * * *